United States Patent
Orengo et al.

(10) Patent No.: US 11,542,326 B2
(45) Date of Patent: *Jan. 3, 2023

(54) ANTI-IL-25 ANTIBODIES AND USES THEREOF

(71) Applicant: Regeneron Pharmaceuticals, Inc., Tarrytown, NY (US)

(72) Inventors: Jamie M. Orengo, Cortlandt Manor, NY (US); Jeanne Allinne, Paris (FR)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 162 days.

This patent is subject to a terminal disclaimer.

(21) Appl. No.: 16/803,582

(22) Filed: Feb. 27, 2020

(65) Prior Publication Data

US 2020/0262912 A1 Aug. 20, 2020

Related U.S. Application Data

(60) Continuation of application No. 15/805,584, filed on Nov. 7, 2017, now Pat. No. 10,640,558, which is a division of application No. 14/861,320, filed on Sep. 22, 2015, now Pat. No. 9,840,557.

(60) Provisional application No. 62/054,167, filed on Sep. 23, 2014.

(51) Int. Cl.
| | |
|---|---|
| C07K 16/24 | (2006.01) |
| A61K 39/395 | (2006.01) |
| C12N 15/09 | (2006.01) |
| C12N 15/11 | (2006.01) |
| A61K 45/06 | (2006.01) |
| A61K 39/00 | (2006.01) |

(52) U.S. Cl.
CPC ........ *C07K 16/244* (2013.01); *A61K 39/3955* (2013.01); *A61K 45/06* (2013.01); *A61K 2039/505* (2013.01); *C07K 2317/21* (2013.01); *C07K 2317/51* (2013.01); *C07K 2317/515* (2013.01); *C07K 2317/76* (2013.01); *C07K 2317/92* (2013.01)

(58) Field of Classification Search
CPC .................. C07K 16/244; C07K 16/24; A61K 39/3955; A61K 39/395; C12N 15/11; C12N 15/09
See application file for complete search history.

(56) References Cited

U.S. PATENT DOCUMENTS

| | | | |
|---|---|---|---|
| 5,015,573 A * | 5/1991 | Yarranton | C12N 9/6481 |
| | | | 435/488 |
| 5,500,362 A | 3/1996 | Robinson et al. | |
| 5,821,337 A | 10/1998 | Carter et al. | |
| 6,596,541 B2 | 7/2003 | Murphy et al. | |
| 7,582,298 B2 | 9/2009 | Stevens et al. | |
| 8,206,717 B2 | 6/2012 | Neil et al. | |
| 8,658,169 B2 | 2/2014 | Matthews et al. | |
| 8,785,605 B2 | 7/2014 | Almagro et al. | |
| 2006/0292644 A1 | 12/2006 | Trakht et al. | |
| 2007/0280945 A1 | 12/2007 | Stevens et al. | |
| 2010/0129380 A1* | 5/2010 | McKenzie | C07K 16/244 |
| | | | 435/69.6 |
| 2011/0318353 A1* | 12/2011 | Almagro | A61P 11/06 |
| | | | 435/69.6 |
| 2014/0037578 A1 | 2/2014 | Zhao et al. | |
| 2016/0083466 A1 | 3/2016 | Orengo et al. | |
| 2018/0057583 A1 | 3/2018 | Orengo et al. | |

FOREIGN PATENT DOCUMENTS

| | | |
|---|---|---|
| WO | 2008/129263 A1 | 10/2008 |
| WO | 2010/038155 A3 | 5/2010 |
| WO | 2011/123507 A1 | 10/2011 |
| WO | 2013/186236 A1 | 12/2013 |

OTHER PUBLICATIONS

Abbott, et al. (2014) "Current approaches to fine mappings of antigen-antibody interactions," Immunology 142 (4):526-35.
Al-Lazikani, et al. (1997) "Standard conformations for the canonical structures of immunoglobulins," J. Mol. Biol., 273:927-948.
Altschul, et al. (1990) "Basic local alignment search tool," J. Mol. Biol., 215(3):403-410.
Altschul, et al. (1997) "Gapped BLAST and PSI-BLAST: a new generation of protein database search programs," Nucleic Acids Res., 25:3389-3402.
Angal, et al. (1993) "A single amino acid substitution abolishes the heterogeneity of chimeric mouse/human (IgG4) antibody," Molecular Immunology, 30:105-108.
Ballantyne, et al. (2007) "Blocking IL-25 prevents airway hyperresponsiveness in allergic asthma" J. Allergy Clin Immunol 120(6): 1324-1331.
Boder, et al. (2000) "Directed evolution of anitbody fragments with monovalent femtomolar antigen-binding affinity," Proc. Natl. Acad. Sci. 97(20):10701-10705.

(Continued)

*Primary Examiner* — Xiaozhen Xie
(74) *Attorney, Agent, or Firm* — FisherBroyles, LLP; Cara L. Crowley-Weber; Lisa Dornbach Flanagan

(57) ABSTRACT

The present invention provides antibodies that bind to human interleukin-25 (IL-25) and methods of using the same. According to certain embodiments, the antibodies of the invention bind human IL-25 with high affinity. In certain embodiments, the invention includes antibodies that bind human IL-25 and block IL-25-mediated cell signaling. The antibodies of the invention may be fully human, non-naturally occurring antibodies. The antibodies of the invention are useful for the treatment of various disorders associated with IL-25 activity or expression, including asthma, allergy, chronic obstructive pulmonary disease (COPD), inflammatory bowel disease (IBD), including ulcerative colitis and Crohn's disease, atopic dermatitis (AD), and Eosinophilic Granulomatosis with Polyangiitis (EGPA), also know as Churg-Strauss Syndrome.

12 Claims, 1 Drawing Sheet

Specification includes a Sequence Listing.

(56) References Cited

OTHER PUBLICATIONS

Büning, et.al. (2003) "The interleukin-25 gene located in the inflammatory bowel disease (IBD) 4 region: No associaiton with inflammatory bowel disease," Eur. J. Immunogenet., 30(5): 329-333.
Camelo, et al. (2012) "Blocking IL-25 signalling protects against gut inflammation in a type-2 model of colitis by suppressing nuocyte and NKT derived IL-13" J. Gastroenterol. 47:1198-1211.
Clynes, et al. (1998) "Fc receptors are required in passive and active immunity to melanoma," PNAS, 95:652-656.
Ehring (1999) "Hydrogen Exchange/Electrospray Ionization Mass Spectrometry Studies of Structural Features of Proteins and Protein/Protein Interactions," Analytical Biochemistry, 267(2):252-259.
Engen and Smith (2001) "Peer Reviewed: Investigating Protein Structure and Dynamics by Hydrogen Exchange MS," Anal. Chem. 73:256A-265A.
Fort, et.al. (2001) "IL-25 Induces IL-4, IL-5, and IL-13 and Th2-Associated Pathologies In Vivo," Immunity 15 (6):985-995.
Gonnet, et al. (1992) "Exhaustive Matching of the Entire Protein Sequence Database," Science 256: 1443-1445.
Harding, et al. (2010) "The immunogenicity of humanized and fully human antibodies," mAbs, Landes Bioscience, 2 (3):256-265.
Hochleitner, et al. (2000) "Characterization of a discontinuous epitope of the human immunodeficiency virus (HIV) core protein p24 by epitope excision and differential chemical modification followed by mass spectrometric peptide mapping analysis," Protein Science, 9:487-496.
Igawa, et al. (2011) "Engineering the variable region of therapeutic IgG antibodies," mAbs, Landes Bioscience 3 (3):243-252.
Iwakura, et.al. (2010) "Functional specialization of interleukin-17 family members," Immunity, 34:149-162.
Junghans, et al. (1990) "Anti-Tac-H, a Humanized Antibody to the Interleukin 2 Receptor with New Features for mmunotherapy in Malignant and Immune Disorderss," Cancer Res., 50:1495-1502.
Kazane, et al., (2013) "Self-assembled antibody multimers through peptide nucleic acid conjugation," J. Am. Chem. Soc. 135(1):340-6, (Epub: Dec. 4, 2012).
Kufer, et al. (2004) "A revival of bispecific antibodies," Trends Biotechnol., 22(5):238-244.
Kim, et.al. (2002) "Transgenic overexpression of human IL-17E results in eosinophilia, B-lymphocyte hyperplasia, and altered antibody production," Blood. 100:2330-2340.
Klein, et al. (2012) "Progress in overcoming the chain association issue in bispecific heterodimeric IgG antibodies," mAbs 4:(6):653-663.
Knappik, et al. (2000) "Fully synthetic human combinatorial antibody libraries (HuCAL) based on modular consensus frameworks and CDRs randomized with trinucleotides," J Mol Biol., 296(1):57-86.
Langer (1990) "New Methods of Drug Delivery," Science 249:1527-1533.
Martin, et al. (1989) "Modeling antibody hypervariable loops: A combined algorithm," PNAS, 86:9268-9272.
Mordenti, et al. (1991) "Interspecies scaling of clearance and volume of distribution data for five therapeutic proteins," Pharmaceut. Res. 8:1351-1359.
Pan, et.al. (2001) "Forced expression of murine IL-17 E induces growth retardation, jaundice, a Th2-biased response, and multiorgan inflammation in mice," J. Immunol. 167:6559-6567.
Pearson (1994) "Using the FASTA program to scratch protein and DNA sequence databases," Methods Mol. Biol., 24: 307-331.
Powell, et al. (1998) "Compendium of excipients for parenteral formulations" PDA, J Pharm Sci Technol, 52:238-311.
Reddy, et al. (2000) "Elimination of Fc Receptor-Dependent Effector Functions of a Modified IgG4 Monoclonal Antibody to Human CD4," J. Immunol., 164:1925-1933.
Reineke (2004) "Antibody epitope mapping using arrays of synthetic peptides," Methods Mol. Biol., 248:443-463.
Rickel, et al. (2008) "Identification of functional roles for both IL-17RB and IL-17RA in mediating IL-25 induced activities," J. Immunol.,181:(6) 4299-4310.
Rouvier, et.al. (1993) "CTLA-8 cloned from an activated T cell, bearing AU-rich messenger RNA instability sequences, and homologous to a herpesvirus saimiri gene," J. Immunol. 150:5445-5456.
Sefton (1987) "Implantable pumps," CRC Crit. Ref. Biomed. Eng., 14:201.
Sherkat, et.al. (2014) "Innate lymphoid cells and cytokines of the novel subtypes of helper T cells in asthma," Asia Pac. Allergy, 4(4):212-221.
Taylor, et al. (1992) "A transgenic mouse that expresses a diversity of human sequence heavy and light chain mmunoglobulins," Nucl. Acids Res., 20:6287-6295.
Tutt, et al. (1991) "Trispecific F(ab')3 derivatives that use cooperative signaling via the TCR/CD3 complex and CD2 to activate and redirect resting cytotoxic T cells," J. Immunol., 147:60-69.
Wang, et al. (2011) "Advances in the production of human monoclonal antibodies," Antibody Technology Journal, (1):1-3.
Wu, et al. (1987) "Receptor-mediated in vitro gene transformation by a soluble DNA carrier system," J. Biol. Chem., 262(10):4429-4432.
International Search Report and Written Opinion, received for PCT/US2015/051407 dated Mar. 30, 2016, 23 pages.

* cited by examiner

| | Binding of mAb-2 to IL-25 which is Pre-Complexed with mAb-1 | | | | | | | | | | | | | | | | | |
|---|---|---|---|---|---|---|---|---|---|---|---|---|---|---|---|---|---|---|
| mAb-1 | 1 | 2 | 3 | 4 | 5 | 6 | 7 | 8 | 9 | 10 | 11 | 12 | 13 | 14 | 15 | 16 | 17 | 18 |
| 1 | 0.00 | 0.04 | 0.03 | 0.04 | 0.04 | 0.04 | 0.01 | 0.05 | 0.05 | 0.00 | 0.85 | 0.91 | 0.60 | 0.59 | 0.66 | 0.64 | 0.80 | 0.97 |
| 2 | 0.00 | 0.00 | 0.00 | 0.01 | 0.00 | 0.01 | 0.00 | 0.01 | 0.02 | 0.00 | 0.67 | 0.86 | 0.59 | 0.58 | 0.62 | 0.59 | 0.74 | 0.91 |
| 3 | 0.00 | 0.00 | 0.00 | 0.01 | 0.00 | 0.01 | 0.00 | 0.01 | 0.02 | 0.00 | 0.72 | 0.83 | 0.58 | 0.57 | 0.61 | 0.56 | 0.73 | 0.87 |
| 4 | 0.00 | 0.02 | 0.00 | 0.00 | 0.02 | 0.00 | 0.00 | 0.03 | 0.02 | 0.00 | 1.12 | 1.13 | 0.89 | 0.83 | 0.94 | 0.92 | 1.11 | 1.30 |
| 5 | 0.00 | 0.19 | 0.00 | 0.01 | 0.00 | 0.00 | 0.00 | 0.01 | 0.01 | 0.00 | 1.08 | 0.99 | 0.74 | 0.73 | 0.82 | 0.77 | 0.97 | 1.22 |
| 6 | 0.00 | 0.00 | 0.00 | 0.00 | 0.00 | 0.00 | 0.00 | 0.01 | 0.01 | 0.00 | 1.00 | 0.98 | 0.72 | 0.71 | 0.80 | 0.73 | 0.93 | 1.21 |
| 7 | 0.00 | 0.04 | 0.03 | 0.01 | 0.03 | 0.02 | 0.00 | 0.05 | 0.03 | 0.00 | 1.02 | 0.99 | 0.76 | 0.73 | 0.83 | 0.81 | 0.99 | 1.25 |
| 8 | 0.00 | 0.00 | 0.00 | 0.00 | 0.00 | 0.00 | 0.00 | 0.00 | 0.00 | 0.00 | 0.94 | 0.97 | 0.72 | 0.71 | 0.81 | 0.79 | 0.93 | 1.13 |
| 9 | 0.00 | 0.00 | 0.00 | 0.00 | 0.00 | 0.00 | 0.00 | 0.00 | 0.00 | 0.00 | 0.85 | 0.99 | 0.77 | 0.68 | 0.79 | 0.71 | 0.92 | 1.19 |
| 10 | 0.00 | 0.03 | 0.02 | 0.03 | 0.04 | 0.02 | 0.00 | 0.08 | 0.05 | 0.00 | 0.19 | 0.77 | 0.48 | 0.50 | 0.56 | 0.51 | 0.66 | 0.85 |
| 11 | 0.53 | 0.63 | 0.64 | 0.57 | 0.68 | 0.64 | 0.47 | 0.77 | 0.62 | 0.11 | 0.00 | 0.69 | 0.54 | 0.45 | 0.52 | 0.61 | 0.74 | 0.52 |
| 12 | 0.51 | 0.63 | 0.64 | 0.56 | 0.67 | 0.61 | 0.48 | 0.67 | 0.58 | 0.70 | 0.78 | 0.00 | 0.42 | 0.48 | 0.47 | 0.50 | 0.68 | 0.88 |
| 13 | 0.58 | 0.72 | 0.76 | 0.65 | 0.75 | 0.75 | 0.55 | 0.77 | 0.66 | 0.82 | 1.03 | 0.88 | 0.00 | 0.02 | 0.11 | 0.09 | 0.20 | 0.30 |
| 14 | 0.63 | 0.73 | 0.74 | 0.71 | 0.77 | 0.64 | 0.60 | 0.82 | 0.72 | 0.82 | 0.90 | 0.87 | 0.03 | 0.00 | 0.08 | 0.06 | 0.13 | 0.28 |
| 15 | 0.59 | 0.70 | 0.68 | 0.67 | 0.73 | 0.60 | 0.57 | 0.77 | 0.68 | 0.77 | 0.79 | 0.68 | 0.00 | 0.00 | 0.00 | 0.00 | 0.05 | 0.17 |
| 16 | 0.57 | 0.68 | 0.66 | 0.63 | 0.70 | 0.56 | 0.55 | 0.75 | 0.66 | 0.74 | 0.90 | 0.73 | 0.00 | 0.00 | 0.00 | 0.00 | 0.05 | 0.16 |
| 17 | 0.62 | 0.74 | 0.74 | 0.70 | 0.78 | 0.72 | 0.56 | 0.86 | 0.72 | 0.79 | 0.99 | 0.87 | 0.00 | 0.00 | 0.00 | 0.00 | 0.00 | 0.13 |
| 18 | 0.55 | 0.67 | 0.66 | 0.63 | 0.69 | 0.63 | 0.50 | 0.76 | 0.64 | 0.68 | 0.50 | 0.76 | 0.00 | 0.00 | 0.00 | 0.00 | 0.00 | 0.00 |

```
                        SEQUENCE LISTING

<160> NUMBER OF SEQ ID NOS: 278

<210> SEQ ID NO 1
<211> LENGTH: 363
<212> TYPE: DNA
<213> ORGANISM: Artificial Sequence
<220> FEATURE:
<223> OTHER INFORMATION: synthetic

<400> SEQUENCE: 1
gaggtgcagc tggtggagtc tgggggaggc ttggtagagc ctgggggtc ccttagactc      60 tcctgtgtag cctctggatt cactttcagt aacgcctgga tgaactgggt ccgccaggct    120
ccagggaagg ggctggagtg ggttggccat attgaaagga aaactgatgg tgggacaaca    180
gacttcgctg cacccgtgaa aggcagattc accatctcaa gagatgattc aaaaaacacg    240
ctgtatctgc aaatgaacag cctgaaaacc gaggacacag ccgtgtatta ctgtaccaca    300
gtgggcccct acagtgtccc ttttgactac tggggccagg gaaccctggt caccgtctcc    360
tca                                                                  363

<210> SEQ ID NO 2
<211> LENGTH: 121
<212> TYPE: PRT
<213> ORGANISM: Artificial Sequence
<220> FEATURE:
<223> OTHER INFORMATION: synthetic

<400> SEQUENCE: 2

Glu Val Gln Leu Val Glu Ser Gly Gly Gly Leu Val Glu Pro Gly Gly
1               5                   10                  15

Ser Leu Arg Leu Ser Cys Val Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly His Ile Glu Arg Lys Thr Asp Gly Gly Thr Thr Asp Phe Ala Ala
    50                  55                  60

Pro Val Lys Gly Arg Phe Thr Ile Ser Arg Asp Asp Ser Lys Asn Thr
65                  70                  75                  80
```

Leu Tyr Leu Gln Met Asn Ser Leu Lys Thr Glu Asp Thr Ala Val Tyr
                85                  90                  95

Tyr Cys Thr Thr Val Gly Pro Tyr Ser Val Pro Phe Asp Tyr Trp Gly
            100                 105                 110

Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcactt tcagtaacgc ctgg                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Asn Ala Trp
1               5

<210> SEQ ID NO 5
<211> LENGTH: 30
<212> TYPE: DNA
<213> ORGANISM: Artificial Sequence
<220> FEATURE:
<223> OTHER INFORMATION: synthetic

<400> SEQUENCE: 5
attgaaagga aaactgatgg tgggacaaca                                    30

<210> SEQ ID NO 6
<211> LENGTH: 10
<212> TYPE: PRT
<213> ORGANISM: Artificial Sequence
<220> FEATURE:
<223> OTHER INFORMATION: synthetic

<400> SEQUENCE: 6

Ile Glu Arg Lys Thr Asp Gly Gly Thr Thr
1               5                   10

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
accacagtgg gcccctacag tgtccctttt gactac                             36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Thr Thr Val Gly Pro Tyr Ser Val Pro Phe Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccatcctcc ctgtctgcat ctgtaggaga cagagtcacc      60
atcacttgcc gggcaagtca gagcattggc agctatttaa attggtatca gcagaaacca     120
gggaaagccc ctaagctcct gatctatgct gcatccagtt tgcaaagtgg ggtcccatca     180
aggttcagtg gcagtggatc tgggacagat tcactctca ccatcagcag tctgcaacct      240
gaagattttg caacttacta ctgtcaacag acttacagta cccccatcac cttcggccaa     300
gggacacgac tggagattaa a                                               321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Ile
                85                  90                  95

Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11

```
cagagcattg gcagctat                                                    18
```

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Gly Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                          9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagactt acagtacccc catcacc                                     27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Thr Tyr Ser Thr Pro Ile Thr
1               5

<210> SEQ ID NO 17
<211> LENGTH: 360
<212> TYPE: DNA
<213> ORGANISM: Artificial Sequence
<220> FEATURE:
<223> OTHER INFORMATION: synthetic

<400> SEQUENCE: 17
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagttccc   300
ataactggaa ctacctggtt cgaccccctg ggccagggaa ccctggtcac cgtctcctca   360

<210> SEQ ID NO 18

```
<211> LENGTH: 120
<212> TYPE: PRT
<213> ORGANISM: Artificial Sequence
<220> FEATURE:
<223> OTHER INFORMATION: synthetic

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Pro Ile Thr Gly Thr Thr Trp Phe Asp Pro Trp Gly Gln
            100                 105                 110

Gly Thr Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggttacacct ttaccagcta tggt                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Tyr Thr Phe Thr Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atcagcgctt acaatggtaa caca                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic
```

<400> SEQUENCE: 22

Ile Ser Ala Tyr Asn Gly Asn Thr
1               5

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
gcgagagttc ccataactgg aactacctgg ttcgacccc                              39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Ala Arg Val Pro Ile Thr Gly Thr Thr Trp Phe Asp Pro
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag acttacagta cccccatcac cttcggccaa      300
gggacacgac tggagattaa a                                                321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Ile
            85                  90                  95

Thr Phe Gly Gln Gly Thr Arg Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta gcagctat                                                18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Ile Ser Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                           9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacagactt acagtacccc catcacc                                      27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Thr Tyr Ser Thr Pro Ile Thr
1               5

<210> SEQ ID NO 33
<211> LENGTH: 363
<212> TYPE: DNA
<213> ORGANISM: Artificial Sequence
<220> FEATURE:
<223> OTHER INFORMATION: synthetic

<400> SEQUENCE: 33

```
caggtgcagc tgcaggagtc gggcccagga ctggtgaagc cttcggagac cctgtccctc    60
acctgcactg tctctggtgg ctccatcagt agtcactact ggagctggat ccggcagccc   120
ccagggaagg gactggaatg gattggtttt atctattaca gtgggagcac caacttcaac   180
ccctccctca gagtcgagt caccatttca atagacacgt ccaagaacca gttctccctg    240
aagctgagct ctgtgaccgc cgcagacacg gccgtgtatt actgtgcgag acatgactac   300
aatgactacg agctcaacta cttcgatctc tggggccgtg gcaccctggc tctgtctcc   360
tca                                                                  363
```

<210> SEQ ID NO 34
<211> LENGTH: 121
<212> TYPE: PRT
<213> ORGANISM: Artificial Sequence
<220> FEATURE:
<223> OTHER INFORMATION: synthetic

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Ile Arg Gln Pro Pro Gly Lys Gly Leu Glu Trp Ile
        35                  40                  45

Gly Phe Ile Tyr Tyr Ser Gly Ser Thr Asn Phe Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Asp Tyr Asn Asp Tyr Glu Leu Asn Tyr Phe Asp Leu Trp Gly
            100                 105                 110

Arg Gly Thr Leu Ala Ser Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggtggctcca tcagtagtca ctac                                           24

<210> SEQ ID NO 36
<211> LENGTH: 8

```
<212> TYPE: PRT
<213> ORGANISM: Artificial Sequence
<220> FEATURE:
<223> OTHER INFORMATION: synthetic

<400> SEQUENCE: 36

Gly Gly Ser Ile Ser Ser His Tyr
1               5

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
atctattaca gtgggagcac c                                              21

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Ile Tyr Tyr Ser Gly Ser Thr
1               5

<210> SEQ ID NO 39
<211> LENGTH: 45
<212> TYPE: DNA
<213> ORGANISM: Artificial Sequence
<220> FEATURE:
<223> OTHER INFORMATION: synthetic

<400> SEQUENCE: 39
gcgagacatg actacaatga ctacgagctc aactacttcg atctc                    45

<210> SEQ ID NO 40
<211> LENGTH: 15
<212> TYPE: PRT
<213> ORGANISM: Artificial Sequence
<220> FEATURE:
<223> OTHER INFORMATION: synthetic

<400> SEQUENCE: 40

Ala Arg His Asp Tyr Asn Asp Tyr Glu Leu Asn Tyr Phe Asp Leu
1               5                   10                  15

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
```

```
aggttcagtg gcagtggatc tgggacagat ttcactctca ccatcagcag tctgcaacct    240
gaagattttg caacttacta ctgtcaacag acttacagta cccccatcac cttcggccaa    300
gggacacgac tggagattaa a                                              321
```

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Ile
                85                  90                  95

Thr Phe Gly Gln Gly Thr Arg Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43

```
cagagcatta gcagctat                                                   18
```

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

```
Gln Ser Ile Ser Ser Tyr
1               5
```

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45

```
gctgcatcc                                                              9
```

<210> SEQ ID NO 46
<211> LENGTH: 3
<212> TYPE: PRT

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacagactt acagtacccc catcacc                                           27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Thr Tyr Ser Thr Pro Ile Thr
1               5

<210> SEQ ID NO 49
<211> LENGTH: 363
<212> TYPE: DNA
<213> ORGANISM: Artificial Sequence
<220> FEATURE:
<223> OTHER INFORMATION: synthetic

<400> SEQUENCE: 49
caggtgcagc tgcaggagtc gggcccaggt ctggtgaagc cttcggagac cctgtccctc        60
acctgcactg tctctggtgc ctccatcagt aattactact ggagttggat ccggcagccc       120
ccagggaagg gactggagtg gattggatat atctttttaca gtgggaacac caactacaac      180
ccctccctca agagtcgagt caccatttca gtagacacgt ccaagaacca gttctccctg       240
aagctgagct ctgtgaccgc cgcagacacg gccgtgtatt actgtgcgag agtcaggttc       300
agtgactacg aactaaactg gttcgacccc tggggccagg ggaccctggt caccgtctcc       360
tca                                                                    363

<210> SEQ ID NO 50
<211> LENGTH: 121
<212> TYPE: PRT
<213> ORGANISM: Artificial Sequence
<220> FEATURE:
<223> OTHER INFORMATION: synthetic

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Phe Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Arg Phe Ser Asp Tyr Glu Leu Asn Trp Phe Asp Pro Trp Gly
            100                 105                 110

Gln Gly Thr Leu Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggtgcctcca tcagtaatta ctac                                    24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Ala Ser Ile Ser Asn Tyr Tyr
1               5

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
atcttttaca gtgggaacac c                                       21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Ile Phe Tyr Ser Gly Asn Thr
1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcgagagtca ggttcagtga ctacgaacta aactggttcg acccc              45

<210> SEQ ID NO 56
<211> LENGTH: 15
<212> TYPE: PRT

<210> SEQ ID NO 57
<211> LENGTH: 339
<212> TYPE: DNA
<213> ORGANISM: Artificial Sequence
<220> FEATURE:
<223> OTHER INFORMATION: synthetic

<400> SEQUENCE: 56

Ala Arg Val Arg Phe Ser Asp Tyr Glu Leu Asn Trp Phe Asp Pro
1               5                   10                  15

<210> SEQ ID NO 57
<211> LENGTH: 339
<212> TYPE: DNA
<213> ORGANISM: Artificial Sequence
<220> FEATURE:
<223> OTHER INFORMATION: synthetic

<400> SEQUENCE: 57

```
gacatcgtga tgacccagtc tccagactcc ctggctgtat ttctgggcga gcgggccacc    60
atcaactgca ggtccagcca gagtgttttt ctcggctcca acaataagaa ctacttagct   120
tggtaccagc agaaacctgg acagcctcct aaactactca tttactgggc gtcttcccgg   180
gaatccgggg tccctgaccg attcagtggc agcgggtcag ggacagattt cactctcact   240
atcaacagcc tgcaggctga agatgtggca gtttattact gtcagcaata tttcattact   300
ccgctcactt tcggcggagg gaccaaggtg gagatcaaa                          339
```

<210> SEQ ID NO 58
<211> LENGTH: 113
<212> TYPE: PRT
<213> ORGANISM: Artificial Sequence
<220> FEATURE:
<223> OTHER INFORMATION: synthetic

<400> SEQUENCE: 58

Asp Ile Val Met Thr Gln Ser Pro Asp Ser Leu Ala Val Phe Leu Gly
1               5                   10                  15

Glu Arg Ala Thr Ile Asn Cys Arg Ser Ser Gln Ser Val Phe Leu Gly
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Phe Ile Thr Pro Leu Thr Phe Gly Gly Gly Thr Lys Val Glu Ile
            100                 105                 110

Lys

<210> SEQ ID NO 59
<211> LENGTH: 36
<212> TYPE: DNA
<213> ORGANISM: Artificial Sequence
<220> FEATURE:
<223> OTHER INFORMATION: synthetic

<400> SEQUENCE: 59

```
cagagtgttt ttctcggctc aacaataag aactac                               36
```

<210> SEQ ID NO 60
<211> LENGTH: 12

<212> TYPE: PRT
<213> ORGANISM: Artificial Sequence
<220> FEATURE:
<223> OTHER INFORMATION: synthetic

<400> SEQUENCE: 60

Gln Ser Val Phe Leu Gly Ser Asn Asn Lys Asn Tyr
1               5                   10

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 tgggcgtct                                                                9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Trp Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
cagcaatatt tcattactcc gctcact                                           27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Tyr Phe Ile Thr Pro Leu Thr
1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65
caggtgcagc tgcaggagtc gggcccagga ctggtgaagc cttcggagac cctgtccctc      60
acctgcactg tctctggtgg ctccatcagt agttacttct ggagctggat ccggcaggcc     120
ccaggaaagg gactggagtg gattggattt atcgattaca gtgggagcac caactacaac     180
ccctccctca agagtcgagt caccatatca gtagacacgt ccaagaacca gttctccctg     240

```
aagttgaact ctgtgaccgc cgcagacacg gccgtctatt actgtgcgag acaagagatc    300
attaacttcg agctgaactg gttcgacccc tggggccagg gaaccctggt cactgtctcc    360
tca                                                                  363
```

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Phe Trp Ser Trp Ile Arg Gln Ala Pro Gly Lys Gly Leu Glu Trp Ile
        35                  40                  45

Gly Phe Ile Asp Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gln Glu Ile Ile Asn Phe Glu Leu Asn Trp Phe Asp Pro Trp Gly
            100                 105                 110

Gln Gly Thr Leu Val Thr Val Ser Ser
        115                 120
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

```
ggtggctcca tcagtagtta cttc                                            24
```

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Gly Ser Ile Ser Ser Tyr Phe
1               5
```

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69

```
atcgattaca gtgggagcac c                                               21
```

```
<210> SEQ ID NO 70
<211> LENGTH: 7
<212> TYPE: PRT
<213> ORGANISM: Artificial Sequence
<220> FEATURE:
<223> OTHER INFORMATION: synthetic

<400> SEQUENCE: 70

Ile Asp Tyr Ser Gly Ser Thr
1               5

<210> SEQ ID NO 71
<211> LENGTH: 45
<212> TYPE: DNA
<213> ORGANISM: Artificial Sequence
<220> FEATURE:
<223> OTHER INFORMATION: synthetic

<400> SEQUENCE: 71
gcgagacaag agatcattaa cttcgagctg aactggttcg acccc          45

<210> SEQ ID NO 72
<211> LENGTH: 15
<212> TYPE: PRT
<213> ORGANISM: Artificial Sequence
<220> FEATURE:
<223> OTHER INFORMATION: synthetic

<400> SEQUENCE: 72

Ala Arg Gln Glu Ile Ile Asn Phe Glu Leu Asn Trp Phe Asp Pro
1               5                   10                  15

<210> SEQ ID NO 73
<211> LENGTH: 339
<212> TYPE: DNA
<213> ORGANISM: Artificial Sequence
<220> FEATURE:
<223> OTHER INFORMATION: synthetic

<400> SEQUENCE: 73
gacatcgtga tgacccagtc tccagcctcc ctggctgtgt ctctgggcga gagggccacc     60
atcaactgca agtccagcca gagtgtttta tacagttcca acaataagaa ctacttagct    120
tggtaccagc agaaaccagg acagcctcct aacctgctca tttactggtc atctacccgg    180
gactccgggg tccctgaccg attcagtggc agcggttctg ggcagatttt cactctcacc    240
atcagcagcc tgcaggctga agatgtggca gtttattact gtcagcaata ttttagtact    300
ccgtggacgt tcggccaagg gaccaaggtg gaaatcaaa                           339

<210> SEQ ID NO 74
<211> LENGTH: 113
<212> TYPE: PRT
<213> ORGANISM: Artificial Sequence
<220> FEATURE:
<223> OTHER INFORMATION: synthetic

<400> SEQUENCE: 74

Asp Ile Val Met Thr Gln Ser Pro Ala Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45
```

```
Pro Pro Asn Leu Leu Ile Tyr Trp Ser Ser Thr Arg Asp Ser Gly Val
    50                  55                  60

Pro Asp Arg Phe Ser Gly Ser Gly Ser Gly Ala Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Thr Pro Trp Thr Phe Gly Gln Gly Thr Lys Val Glu Ile
            100                 105                 110

Lys

<210> SEQ ID NO 75
<211> LENGTH: 36
<212> TYPE: DNA
<213> ORGANISM: Artificial Sequence
<220> FEATURE:
<223> OTHER INFORMATION: synthetic

<400> SEQUENCE: 75
cagagtgttt tatacagttc aacaataag aactac                          36

<210> SEQ ID NO 76
<211> LENGTH: 12
<212> TYPE: PRT
<213> ORGANISM: Artificial Sequence
<220> FEATURE:
<223> OTHER INFORMATION: synthetic

<400> SEQUENCE: 76

Gln Ser Val Leu Tyr Ser Ser Asn Asn Lys Asn Tyr
1               5                   10

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 tggtcatct                                                        9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Trp Ser Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
cagcaatatt ttagtactcc gtggacg                                   27

<210> SEQ ID NO 80
```

```
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Phe Ser Thr Pro Trp Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81
caggttcagc tggtgcagtc cggagctgag gtgaagaagc tggggcctc  agtgaaggtc    60 tcctgtaagg cttctggtta cacctttagt agttatggta ttagctgggt gcgacaggcc   120
cctggacaag gcttgagtg  gatgggatgg atcagcgctt acaatgataa cacacagtat   180
gcacagaaat tccagggcag agtcaccatg accacagaca catccacgag cacagcctac   240
atggagctga ggagcctgag atctgacgac acggccgtgt attactgtgc gagagtccca   300
ttacaatggt tcggggagtc ctttgaccac tggggccagg gaaccctggt caccgtctcc   360
tca                                                                 363

<210> SEQ ID NO 82
<211> LENGTH: 121
<212> TYPE: PRT
<213> ORGANISM: Artificial Sequence
<220> FEATURE:
<223> OTHER INFORMATION: synthetic

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asn Thr Gln Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Pro Leu Gln Trp Phe Gly Glu Ser Phe Asp His Trp Gly
            100                 105                 110

Gln Gly Thr Leu Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic
```

<400> SEQUENCE: 83
ggttacacct ttagtagtta tggt                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Tyr Thr Phe Ser Ser Tyr Gly
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
atcagcgctt acaatgataa caca                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Ser Ala Tyr Asn Asp Asn Thr
1               5

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87
gcgagagtcc cattacaatg gttcggggag tcctttgacc ac                      42

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Val Pro Leu Gln Trp Phe Gly Glu Ser Phe Asp His
1               5                   10

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89

```
gacatccaga tgacccagtc tccatcctcc ctgtctgcat ctgtggggga cagagtcacc      60
atcacttgcc gggcaagtca ggacattaac aactatttaa attggtttca gcagaaacca     120
gggaaagccc ctaagctcct gatctttttct acatccagtt tgcaaagtgg ggtcccatca    180
aggttcagtg gcagtggctc tggaacagat tcactctca ccatcagcag tctccaatct      240
gaagattttg caacttatta ctgtcaacag actttcatta ccccgctcac tttcggcggc     300
gggaccaagg tggagatcaa a                                               321
```

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Phe Gln Gln Lys Pro Gly Lys Ala Pro Lys Leu Leu Ile
        35                  40                  45

Phe Ser Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Thr Phe Ile Thr Pro Leu
                85                  90                  95

Thr Phe Gly Gly Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91

```
caggacatta acaactat                                                    18
```

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

```
Gln Asp Ile Asn Asn Tyr
1               5
```

<210> SEQ ID NO 93
<211> LENGTH: 9
<212> TYPE: DNA
<213> ORGANISM: Artificial Sequence
<220> FEATURE:
<223> OTHER INFORMATION: synthetic

```
<400> SEQUENCE: 93 tctacatcc                                                              9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ser Thr Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caacagactt tcattacccc gctcact                                         27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Thr Phe Ile Thr Pro Leu Thr
1               5

<210> SEQ ID NO 97
<211> LENGTH: 363
<212> TYPE: DNA
<213> ORGANISM: Artificial Sequence
<220> FEATURE:
<223> OTHER INFORMATION: synthetic

<400> SEQUENCE: 97
caggtgcagc tgcaggagtc gggcccagga ctggtgaagc cttcggagac cctgtccctc    60
acttgtactg tctctggtgg ctccatcagt aattacttct ggagctggat ccggcagccc   120
ccagggaagg gactggagtg gattgggttt aactataaca gtgggagcac caactataac   180
ccctccctca gagtcgagt caccatttca gtagacacgt ccaagaacca gttctccctg    240
aagctgagct ctgtgaccgc tgcggacacg gccgtgtatt actgtgcgag agggtataac   300
tggaactacg aaatagcttg gttcgacccc tggggccagg aaccctggt cactgtctcc    360 tca                                                                 363

<210> SEQ ID NO 98
<211> LENGTH: 121
<212> TYPE: PRT
<213> ORGANISM: Artificial Sequence
<220> FEATURE:
<223> OTHER INFORMATION: synthetic

<400> SEQUENCE: 98

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Asn Tyr
         20                  25                  30

Phe Trp Ser Trp Ile Arg Gln Pro Pro Gly Lys Gly Leu Glu Trp Ile
     35                  40                  45

Gly Phe Asn Tyr Asn Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Gly Tyr Asn Trp Asn Tyr Glu Ile Ala Trp Phe Asp Pro Trp Gly
             100                 105                 110

Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggtggctcca tcagtaatta cttc                                          24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Gly Ser Ile Ser Asn Tyr Phe
1               5
```

<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
aactataaca gtgggagcac c                                             21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

```
Asn Tyr Asn Ser Gly Ser Thr
1               5
```

<210> SEQ ID NO 103
<211> LENGTH: 45
<212> TYPE: DNA
<213> ORGANISM: Artificial Sequence
<220> FEATURE:
<223> OTHER INFORMATION: synthetic

<400> SEQUENCE: 103
gcgagagggt ataactggaa ctacgaaata gcttggttcg acccc    45

<210> SEQ ID NO 104
<211> LENGTH: 15
<212> TYPE: PRT
<213> ORGANISM: Artificial Sequence
<220> FEATURE:
<223> OTHER INFORMATION: synthetic

<400> SEQUENCE: 104

Ala Arg Gly Tyr Asn Trp Asn Tyr Glu Ile Ala Trp Phe Asp Pro
1               5                   10                  15

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccatcctcc ctgtctgcat ctgtaggaga cagagtcacc    60
atcacttgcc gggcaagtca gagcataagc agttatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ttgtcaacag agttacctta ccccgctcac tttcggcgga   300
gggaccaagg tggagatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Leu Thr Pro Leu
                85                  90                  95

Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagcataa gcagttat                                                18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctgcatcc                                                          9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacagagtt accttacccc gctcact                                      27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Ser Tyr Leu Thr Pro Leu Thr
1               5

<210> SEQ ID NO 113
<211> LENGTH: 375
<212> TYPE: DNA
<213> ORGANISM: Artificial Sequence
<220> FEATURE:
<223> OTHER INFORMATION: synthetic

<400> SEQUENCE: 113

```
caggttcagc tggtgcagtc tggagctgag gtgatgaagc ctggggcctc agtgaaggtc      60
tcctgcaagt cttctgactt cgcctttacc acctatggca tcagctgggt gcgacaggcc     120
cctggacaag gcttgagtg gatgggatgg atcagcgctt acaatggtaa cacaaactat     180
gaacagaggt tccagggcag aatcaccatg accacagaca catccacgac cacagtttat     240
atggagttga ggagcctgag atctgacgac acggccgtgt attactgtgc gagagatccc     300
gactattgta gtagtaacac tgttctgat gcttttgatt tgtggggcca agggacaatg     360
gtcaccgtct cttca                                                      375
```

<210> SEQ ID NO 114
<211> LENGTH: 125
<212> TYPE: PRT
<213> ORGANISM: Artificial Sequence
<220> FEATURE:
<223> OTHER INFORMATION: synthetic

<400> SEQUENCE: 114

```
Gln Val Gln Leu Val Gln Ser Gly Ala Glu Val Met Lys Pro Gly Ala
1               5                   10                  15

Ser Val Lys Val Ser Cys Lys Ser Ser Asp Phe Ala Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Glu Gln Arg Phe
    50                  55                  60

Gln Gly Arg Ile Thr Met Thr Thr Asp Thr Ser Thr Thr Val Tyr
65                  70                  75                  80

Met Glu Leu Arg Ser Leu Arg Ser Asp Asp Thr Ala Val Tyr Tyr Cys
                85                  90                  95

Ala Arg Asp Pro Asp Tyr Cys Ser Ser Asn Thr Cys Ser Asp Ala Phe
            100                 105                 110

Asp Leu Trp Gly Gln Gly Thr Met Val Thr Val Ser Ser
        115                 120                 125
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115

```
gacttcgcct ttaccaccta tggc                                             24
```

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

```
Asp Phe Ala Phe Thr Thr Tyr Gly
1               5
```

<210> SEQ ID NO 117
<211> LENGTH: 24

```
<212> TYPE: DNA
<213> ORGANISM: Artificial Sequence
<220> FEATURE:
<223> OTHER INFORMATION: synthetic

<400> SEQUENCE: 117
atcagcgctt acaatggtaa caca                                            24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Ala Tyr Asn Gly Asn Thr
1               5

<210> SEQ ID NO 119
<211> LENGTH: 54
<212> TYPE: DNA
<213> ORGANISM: Artificial Sequence
<220> FEATURE:
<223> OTHER INFORMATION: synthetic

<400> SEQUENCE: 119
gcgagagatc ccgactattg tagtagtaac acctgttctg atgcttttga tttg          54

<210> SEQ ID NO 120
<211> LENGTH: 18
<212> TYPE: PRT
<213> ORGANISM: Artificial Sequence
<220> FEATURE:
<223> OTHER INFORMATION: synthetic

<400> SEQUENCE: 120

Ala Arg Asp Pro Asp Tyr Cys Ser Ser Asn Thr Cys Ser Asp Ala Phe
1               5                   10                  15
Asp Leu

<210> SEQ ID NO 121
<211> LENGTH: 321
<212> TYPE: DNA
<213> ORGANISM: Artificial Sequence
<220> FEATURE:
<223> OTHER INFORMATION: synthetic

<400> SEQUENCE: 121
gacatccaga tgacccagtc tccatcctcc ctgtctgcat ctgtacgaga cagagtcacc     60
atcacttgcc gggcgagtca gggcattacc aattatttag cctggtatca gcagaaacca    120
gggaaagttc ctaaggtcct gatctatgct gcatccactt tgcaatcagg ggtcccatct    180
cggttcagtg gcagtggctc tgggacagaa ttcactctcg ccatcagcag cctgcagcct    240
gaggatgttg caacttattt ctgtcaacag tatggcagtg ccccttggac gttcggccaa    300
gggaccaagg tggaaatcaa a                                              321

<210> SEQ ID NO 122
<211> LENGTH: 107
<212> TYPE: PRT
<213> ORGANISM: Artificial Sequence
<220> FEATURE:
<223> OTHER INFORMATION: synthetic
```

<400> SEQUENCE: 122

Asp Ile Gln Met Thr Gln Ser Pro Ser Ser Leu Ser Ala Ser Val Arg
1               5                   10                  15

Asp Arg Val Thr Ile Thr Cys Arg Ala Ser Gln Gly Ile Thr Asn Tyr
            20                  25                  30

Leu Ala Trp Tyr Gln Gln Lys Pro Gly Lys Val Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Ala Ile Ser Ser Leu Gln Pro
65                  70                  75                  80

Glu Asp Val Ala Thr Tyr Phe Cys Gln Gln Tyr Gly Ser Ala Pro Trp
                85                  90                  95

Thr Phe Gly Gln Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123
cagggcatta ccaattat                                                        18

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

Gln Gly Ile Thr Asn Tyr
1               5

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 gctgcatcc                                                                   9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:

<223> OTHER INFORMATION: synthetic

<400> SEQUENCE: 127
caacagtatg gcagtgcccc ttggacg                                              27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Tyr Gly Ser Ala Pro Trp Thr
1               5

<210> SEQ ID NO 129
<211> LENGTH: 360
<212> TYPE: DNA
<213> ORGANISM: Artificial Sequence
<220> FEATURE:
<223> OTHER INFORMATION: synthetic

<400> SEQUENCE: 129
caggttcagc tggtgcagtc tggagctgag gtgaagaaac ctggggcctc agtgaaggtc        60
tcctgcaagg cttctgagta cacctttagc aactatggca tcagctgggt gcgacaggcc      120
cctggacaag gtcttgagtg gttggggtgg atcggcgctt atagtggttt cacaaaatat      180
gcacagaagg tccaggacag aatcaccatg accacagacg catccacgac cacagcctac      240
atggagctga gaaacctgag atctgacgac acggccgtgt attattgtgc gagagtggga      300
actggaactg actcttactt tgacttctgg ggccagggaa ccctggtcac cgtctcctca      360

<210> SEQ ID NO 130
<211> LENGTH: 120
<212> TYPE: PRT
<213> ORGANISM: Artificial Sequence
<220> FEATURE:
<223> OTHER INFORMATION: synthetic

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Glu Tyr Thr Phe Ser Asn Tyr
                20                  25                  30

Gly Ile Ser Trp Val Arg Gln Ala Pro Gly Gln Gly Leu Glu Trp Leu
            35                  40                  45

Gly Trp Ile Gly Ala Tyr Ser Gly Phe Thr Lys Tyr Ala Gln Lys Val
        50                  55                  60

Gln Asp Arg Ile Thr Met Thr Thr Asp Ala Ser Thr Thr Thr Ala Tyr
65                  70                  75                  80

Met Glu Leu Arg Asn Leu Arg Ser Asp Asp Thr Ala Val Tyr Tyr Cys
                85                  90                  95

Ala Arg Val Gly Thr Gly Thr Asp Ser Tyr Phe Asp Phe Trp Gly Gln
            100                 105                 110

Gly Thr Leu Val Thr Val Ser Ser
        115                 120

<210> SEQ ID NO 131
<211> LENGTH: 24
<212> TYPE: DNA

```
<213> ORGANISM: Artificial Sequence
<220> FEATURE:
<223> OTHER INFORMATION: synthetic

<400> SEQUENCE: 131
gagtacacct ttagcaacta tggc                                              24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Glu Tyr Thr Phe Ser Asn Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atcggcgctt atagtggttt caca                                              24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Gly Ala Tyr Ser Gly Phe Thr
1               5

<210> SEQ ID NO 135
<211> LENGTH: 39
<212> TYPE: DNA
<213> ORGANISM: Artificial Sequence
<220> FEATURE:
<223> OTHER INFORMATION: synthetic

<400> SEQUENCE: 135
gcgagagtgg gaactggaac tgactcttac tttgacttc                              39

<210> SEQ ID NO 136
<211> LENGTH: 13
<212> TYPE: PRT
<213> ORGANISM: Artificial Sequence
<220> FEATURE:
<223> OTHER INFORMATION: synthetic

<400> SEQUENCE: 136

Ala Arg Val Gly Thr Gly Thr Asp Ser Tyr Phe Asp Phe
1               5                   10

<210> SEQ ID NO 137
<211> LENGTH: 321
<212> TYPE: DNA
<213> ORGANISM: Artificial Sequence
<220> FEATURE:
<223> OTHER INFORMATION: synthetic
```

<400> SEQUENCE: 137

```
gacatccaga tgacccagtc tccatcctcc ctgtctgcat ctgtaggaga cagagtcacc        60
atcacttgcc gggcaagtca gaacattaac agtcatttaa attggtatca gcagaaacca       120
gggaaagccc ctaaactcct gatttatact gcatccagtt tgcaaagtgg ggtcccatta       180
agattcagtg gcagtggatc tgggacagat ttcactctca ccatcagcag tctgcaacct       240
gaagattttg gaatttacat ctgtcaacag acttacataa cccctctcac tttcggcggt       300
gggaccaagg tggagatcaa a                                                 321
```

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Ser His
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Ile Tyr Ile Cys Gln Gln Thr Tyr Ile Thr Pro Leu
                85                  90                  95

Thr Phe Gly Gly Gly Thr Lys Val Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139

```
cagaacatta acagtcat                                                      18
```

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

```
Gln Asn Ile Asn Ser His
1               5
```

<210> SEQ ID NO 141
<211> LENGTH: 9
<212> TYPE: DNA
<213> ORGANISM: Artificial Sequence
<220> FEATURE:
<223> OTHER INFORMATION: synthetic

```
<400> SEQUENCE: 141 actgcatcc                                                             9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Thr Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagactt acataacccc tctcact                                        27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Thr Tyr Ile Thr Pro Leu Thr
1               5

<210> SEQ ID NO 145
<211> LENGTH: 369
<212> TYPE: DNA
<213> ORGANISM: Artificial Sequence
<220> FEATURE:
<223> OTHER INFORMATION: synthetic

<400> SEQUENCE: 145
caggtgcagc tgcaggagtc gggcccagga cttgtgaagt cttcggagac cctgtccctc    60
acctgcactg tctctggtgg ctccatcagt agttactact ggagctggat ccggcagccc   120
ccagggaagg gcctggaatg gattggattt atctattaca gtgggagcac caactacaac   180 ccctcccctca agagtcgagt cacctttttca gtagacactt ccaaaaacca cttctccctg   240
aagctgaact ctgtgaccgc cacagacacg gccgtgtatt actgtgcgcg acattacttt   300
gattcgggga cttatgaact ggggcctttt gactactggg gccagggaac cctggtcacc   360
gtctcctca                                                           369

<210> SEQ ID NO 146
<211> LENGTH: 123
<212> TYPE: PRT
<213> ORGANISM: Artificial Sequence
<220> FEATURE:
<223> OTHER INFORMATION: synthetic

<400> SEQUENCE: 146

Gln Val Gln Leu Gln Glu Ser Gly Pro Gly Leu Val Lys Ser Ser Glu
1               5                   10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Ser Gly Ser Thr Asn Tyr Asn Pro Ser Leu Lys
    50                  55                  60

Ser Arg Val Thr Phe Ser Val Asp Thr Ser Lys Asn His Phe Ser Leu
65                  70                  75                  80

Lys Leu Asn Ser Val Thr Ala Thr Asp Thr Ala Val Tyr Tyr Cys Ala
                85                  90                  95

Arg His Tyr Phe Asp Ser Gly Tyr Glu Leu Gly Pro Phe Asp Tyr
            100                 105                 110

Trp Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggtggctcca tcagtagtta ctac                                    24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Gly Ser Ile Ser Ser Tyr Tyr
1               5

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149
atctattaca gtgggagcac c                                       21

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Tyr Tyr Ser Gly Ser Thr
1               5

<210> SEQ ID NO 151
<211> LENGTH: 51
<212> TYPE: DNA
<213> ORGANISM: Artificial Sequence
<220> FEATURE:
<223> OTHER INFORMATION: synthetic
```

<400> SEQUENCE: 151
gcgcgacatt actttgattc ggggacttat gaactggggc cttttgacta c         51

<210> SEQ ID NO 152
<211> LENGTH: 17
<212> TYPE: PRT
<213> ORGANISM: Artificial Sequence
<220> FEATURE:
<223> OTHER INFORMATION: synthetic

<400> SEQUENCE: 152

Ala Arg His Tyr Phe Asp Ser Gly Thr Tyr Glu Leu Gly Pro Phe Asp
1               5                   10                  15

Tyr

<210> SEQ ID NO 153
<211> LENGTH: 339
<212> TYPE: DNA
<213> ORGANISM: Artificial Sequence
<220> FEATURE:
<223> OTHER INFORMATION: synthetic

<400> SEQUENCE: 153
gacatcgtga tgacccagtc tccagactcc ctggctgtgt ctctgggcga gagggccacc    60
atcaactgca gtccagcca gaatatttta ttaacttcca gtaataagaa ctacttaact   120
tggtaccagc agaaaccagg acagcctcct aagctgctca tttactgggc atctattcgg   180
gaatccgggg tccctgaccg attcagtggc agcgggtctg ggacagattt cactctcacc   240
atcagcagcc tgcaggctga agatgtggca ctttatttct gtcagcaata ttatattact   300
ccattcactt tcggccctgg gaccaaagtg gatatcaaa                         339

<210> SEQ ID NO 154
<211> LENGTH: 113
<212> TYPE: PRT
<213> ORGANISM: Artificial Sequence
<220> FEATURE:
<223> OTHER INFORMATION: synthetic

<400> SEQUENCE: 154

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Leu Thr
            20                  25                  30

Ser Ser Asn Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Phe Cys Gln Gln
                85                  90                  95

Tyr Tyr Ile Thr Pro Phe Thr Phe Gly Pro Gly Thr Lys Val Asp Ile
            100                 105                 110

Lys

<210> SEQ ID NO 155
<211> LENGTH: 36
<212> TYPE: DNA

```
<213> ORGANISM: Artificial Sequence
<220> FEATURE:
<223> OTHER INFORMATION: synthetic

<400> SEQUENCE: 155
cagaatattt tattaacttc cagtaataag aactac                                    36

<210> SEQ ID NO 156
<211> LENGTH: 12
<212> TYPE: PRT
<213> ORGANISM: Artificial Sequence
<220> FEATURE:
<223> OTHER INFORMATION: synthetic

<400> SEQUENCE: 156

Gln Asn Ile Leu Leu Thr Ser Ser Asn Lys Asn Tyr
1               5                   10

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 tgggcatct                                                                  9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Trp Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
cagcaatatt atattactcc attcact                                              27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Tyr Tyr Ile Thr Pro Phe Thr
1               5

<210> SEQ ID NO 161
<211> LENGTH: 372
<212> TYPE: DNA
<213> ORGANISM: Artificial Sequence
<220> FEATURE:
<223> OTHER INFORMATION: synthetic
```

<400> SEQUENCE: 161

```
caggtgcagc tgcaggagtc gggcccagga ctggtgaagc cttcggagac cctgtccctc    60
acctgcactg tctctggtgg ctccatcagt gattactact ggagctggat ccggcagccc   120
ccagggaagg gactggagtg gattggccat atctattaca gtgggagcac caaccacaac   180
ccctccctca agagtcgagt cgccatatca gtcgacacgt ccaagaacca gttctccctg   240
aggctgtact ctgtgaccgc tgcggacacg gccgtgtatt actgtgcgag agacgggtat   300
agtagctcgt ccggcttcta ctacttcggt atggacgtct ggggccaagg gaccacggtc   360
accgtctcct ca                                                       372
```

<210> SEQ ID NO 162
<211> LENGTH: 124
<212> TYPE: PRT
<213> ORGANISM: Artificial Sequence
<220> FEATURE:
<223> OTHER INFORMATION: synthetic

<400> SEQUENCE: 162

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Asp Tyr
            20                  25                  30
Tyr Trp Ser Trp Ile Arg Gln Pro Pro Gly Lys Gly Leu Glu Trp Ile
        35                  40                  45
Gly His Ile Tyr Tyr Ser Gly Ser Thr Asn His Asn Pro Ser Leu Lys
    50                  55                  60
Ser Arg Val Ala Ile Ser Val Asp Thr Ser Lys Asn Gln Phe Ser Leu
65                  70                  75                  80
Arg Leu Tyr Ser Val Thr Ala Ala Asp Thr Ala Val Tyr Tyr Cys Ala
                85                  90                  95
Arg Asp Gly Tyr Ser Ser Ser Gly Phe Tyr Tyr Phe Gly Met Asp
            100                 105                 110
Val Trp Gly Gln Gly Thr Thr Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163

```
ggtggctcca tcagtgatta ctac                                           24
```

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

```
Gly Gly Ser Ile Ser Asp Tyr Tyr
1               5
```

<210> SEQ ID NO 165
<211> LENGTH: 21
<212> TYPE: DNA

```
<213> ORGANISM: Artificial Sequence
<220> FEATURE:
<223> OTHER INFORMATION: synthetic

<400> SEQUENCE: 165
atctattaca gtgggagcac c                                             21

<210> SEQ ID NO 166
<211> LENGTH: 7
<212> TYPE: PRT
<213> ORGANISM: Artificial Sequence
<220> FEATURE:
<223> OTHER INFORMATION: synthetic

<400> SEQUENCE: 166

Ile Tyr Tyr Ser Gly Ser Thr
1               5

<210> SEQ ID NO 167
<211> LENGTH: 54
<212> TYPE: DNA
<213> ORGANISM: Artificial Sequence
<220> FEATURE:
<223> OTHER INFORMATION: synthetic

<400> SEQUENCE: 167
gcgagagacg ggtatagtag ctcgtccggc ttctactact tcggtatgga cgtc         54

<210> SEQ ID NO 168
<211> LENGTH: 18
<212> TYPE: PRT
<213> ORGANISM: Artificial Sequence
<220> FEATURE:
<223> OTHER INFORMATION: synthetic

<400> SEQUENCE: 168

Ala Arg Asp Gly Tyr Ser Ser Ser Gly Phe Tyr Tyr Phe Gly Met
1               5                   10                  15

Asp Val

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gacatccagt tgacccagtc tccatccttc ctgtctgcat ctgtcggaga cagagtcacc   60
atcacttgct gggccagtca ggacattaac agttatttag cctggtatca gcaaaaacca  120
gggaaagccc ctaagctcct gatctttgct gcatccactt tgcaaggtgg ggtcccttct  180
aggttcagcg gcagtggatc tgggacagaa ttcactctca caatcagcag cctgcagcct  240
gaagattttg caacttatta ctgtcaacac cttagtagtt tccctcccac cttcggccaa  300
gggacacgac tggagattaa a                                            321

<210> SEQ ID NO 170
<211> LENGTH: 107
<212> TYPE: PRT
<213> ORGANISM: Artificial Sequence
<220> FEATURE:
<223> OTHER INFORMATION: synthetic
```

<400> SEQUENCE: 170

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Asn Ser Tyr
            20                  25                  30

Leu Ala Trp Tyr Gln Gln Lys Pro Gly Lys Ala Pro Lys Leu Leu Ile
        35                  40                  45

Phe Ala Ala Ser Thr Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Leu Ser Ser Phe Pro Pro
                85                  90                  95

Thr Phe Gly Gln Gly Thr Arg Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
caggacatta acagttat                                                 18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Asp Ile Asn Ser Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gctgcatcc                                                            9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
1

<210> SEQ ID NO 175
<211> LENGTH: 27
<212> TYPE: DNA
<213> ORGANISM: Artificial Sequence

```
<220> FEATURE:
<223> OTHER INFORMATION: synthetic

<400> SEQUENCE: 175
caacacctta gtagtttccc tcccacc                                             27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln His Leu Ser Ser Phe Pro Pro Thr
1               5

<210> SEQ ID NO 177
<211> LENGTH: 363
<212> TYPE: DNA
<213> ORGANISM: Artificial Sequence
<220> FEATURE:
<223> OTHER INFORMATION: synthetic

<400> SEQUENCE: 177
caggtgcagc tgcaggagtc gggcccagga ctggtgaggc cttcggagac cctatccctc          60
atctgcactg tctctggtgg ctccatcaat agttactact ggagctggat ccggcagccc         120
ccagggaagg gactggaatg gattggatat atctattaca gtgggagcac caactacaac         180
ccctccctca gagtcgagt caccatatca ggagacacgt ccaagaacca gttctccctg          240
aagctgagct ctgtgaccgc tgcggacacg gccgtgtatt actgcgcgag aggggtaatc         300
tggaactacg aactccgaga atttgactac tggggccagg gaaccctggt caccgtctcc         360
tca                                                                      363

<210> SEQ ID NO 178
<211> LENGTH: 121
<212> TYPE: PRT
<213> ORGANISM: Artificial Sequence
<220> FEATURE:
<223> OTHER INFORMATION: synthetic

<400> SEQUENCE: 178

Gln Val Gln Leu Gln Glu Ser Gly Pro Gly Leu Val Arg Pro Ser Glu
1               5                   10                  15

Thr Leu Ser Leu Ile Cys Thr Val Ser Gly Gly Ser Ile Asn Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Gly Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Ile Trp Asn Tyr Glu Leu Arg Glu Phe Asp Tyr Trp Gly
            100                 105                 110

Gln Gly Thr Leu Val Thr Val Ser Ser
        115                 120
```

```
<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggtggctcca tcaatagtta ctac                                          24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Gly Ser Ile Asn Ser Tyr Tyr
1               5

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
atctattaca gtgggagcac c                                             21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Ile Tyr Tyr Ser Gly Ser Thr
1               5

<210> SEQ ID NO 183
<211> LENGTH: 45
<212> TYPE: DNA
<213> ORGANISM: Artificial Sequence
<220> FEATURE:
<223> OTHER INFORMATION: synthetic

<400> SEQUENCE: 183
gcgagagggg taatctggaa ctacgaactc cgagaatttg actac                   45

<210> SEQ ID NO 184
<211> LENGTH: 15
<212> TYPE: PRT
<213> ORGANISM: Artificial Sequence
<220> FEATURE:
<223> OTHER INFORMATION: synthetic

<400> SEQUENCE: 184

Ala Arg Gly Val Ile Trp Asn Tyr Glu Leu Arg Glu Phe Asp Tyr
1               5                   10                  15

<210> SEQ ID NO 185
<211> LENGTH: 339
<212> TYPE: DNA
<213> ORGANISM: Artificial Sequence
```

-continued

```
<220> FEATURE:
<223> OTHER INFORMATION: synthetic

<400> SEQUENCE: 185
gacatcgtga tgacccagtc tccagactcc ctggctgtgt ctctgggcga gagggccacc    60
atcaactgca gtccagcca gagtgtttta gacagttcca acaataagaa ctacttagtt   120
tggtaccagc agaaaccagg acagcctcct gagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatttttact   300 ccgctcacct tcggcggagg gaccaaggtg gagatcaaa                          339

<210> SEQ ID NO 186
<211> LENGTH: 113
<212> TYPE: PRT
<213> ORGANISM: Artificial Sequence
<220> FEATURE:
<223> OTHER INFORMATION: synthetic

<400> SEQUENCE: 186

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asn Asn Lys Asn Tyr Leu Val Trp Tyr Gln Gln Lys Pro Gly Gln
        35                  40                  45

Pro Pro Glu Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Phe Thr Pro Leu Thr Phe Gly Gly Gly Thr Lys Val Glu Ile
            100                 105                 110

Lys

<210> SEQ ID NO 187
<211> LENGTH: 36
<212> TYPE: DNA
<213> ORGANISM: Artificial Sequence
<220> FEATURE:
<223> OTHER INFORMATION: synthetic

<400> SEQUENCE: 187
cagagtgttt tagacagttc aacaataag aactac                              36

<210> SEQ ID NO 188
<211> LENGTH: 12
<212> TYPE: PRT
<213> ORGANISM: Artificial Sequence
<220> FEATURE:
<223> OTHER INFORMATION: synthetic

<400> SEQUENCE: 188

Gln Ser Val Leu Asp Ser Ser Asn Asn Lys Asn Tyr
1               5                   10

<210> SEQ ID NO 189
<211> LENGTH: 9
<212> TYPE: DNA
```

```
<213> ORGANISM: Artificial Sequence
<220> FEATURE:
<223> OTHER INFORMATION: synthetic

<400> SEQUENCE: 189 tgggcatct                                                                    9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Trp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
cagcaatatt attttactcc gctcacc                                               27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Tyr Tyr Phe Thr Pro Leu Thr
1               5

<210> SEQ ID NO 193
<211> LENGTH: 369
<212> TYPE: DNA
<213> ORGANISM: Artificial Sequence
<220> FEATURE:
<223> OTHER INFORMATION: synthetic

<400> SEQUENCE: 193
cagctgcagc tgcaggagtc gggcccagga ctggtgaggc cttcggagac cctgtccctc          60
acctgcagtg tctcgagtgg ctccatcaga agtagtaatt actactgggg ctggatccgc         120
cagcccccag ggaagggact ggagtggatt gggaatatct attatagtgg gaacaccttc         180
tataacccgt ccctcaaggg tcgagtcacc atatccgtag acacgtccaa gaaccagttc         240
tccctgaagc tgagctctgt gaccgccaca gacacggctg tgtattactg tgcgagacaa         300
ggatatagtg actacgagtt gaactggttc gacccctggg gccagggaac cctggtcacc         360
gtctcctca                                                                369

<210> SEQ ID NO 194
<211> LENGTH: 123
<212> TYPE: PRT
<213> ORGANISM: Artificial Sequence
<220> FEATURE:
<223> OTHER INFORMATION: synthetic
```

<400> SEQUENCE: 194

Gln Leu Gln Leu Gln Glu Ser Gly Pro Gly Leu Val Arg Pro Ser Glu
1               5                   10                  15

Thr Leu Ser Leu Thr Cys Ser Val Ser Gly Ser Ile Arg Ser Ser
            20                  25                  30

Asn Tyr Tyr Trp Gly Trp Ile Arg Gln Pro Pro Gly Lys Gly Leu Glu
            35                  40                  45

Trp Ile Gly Asn Ile Tyr Tyr Ser Gly Asn Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Thr Asp Thr Ala Val Tyr Tyr
            85                  90                  95

Cys Ala Arg Gln Gly Tyr Ser Asp Tyr Glu Leu Asn Trp Phe Asp Pro
            100                 105                 110

Trp Gly Gln Gly Thr Leu Val Thr Val Ser Ser
        115                 120

<210> SEQ ID NO 195
<211> LENGTH: 30
<212> TYPE: DNA
<213> ORGANISM: Artificial Sequence
<220> FEATURE:
<223> OTHER INFORMATION: synthetic

<400> SEQUENCE: 195
agtggctcca tcagaagtag taattactac                                           30

<210> SEQ ID NO 196
<211> LENGTH: 10
<212> TYPE: PRT
<213> ORGANISM: Artificial Sequence
<220> FEATURE:
<223> OTHER INFORMATION: synthetic

<400> SEQUENCE: 196

Ser Gly Ser Ile Arg Ser Ser Asn Tyr Tyr
1               5                   10

<210> SEQ ID NO 197
<211> LENGTH: 21
<212> TYPE: DNA
<213> ORGANISM: Artificial Sequence
<220> FEATURE:
<223> OTHER INFORMATION: synthetic

<400> SEQUENCE: 197
atctattata gtgggaacac c                                                    21

<210> SEQ ID NO 198
<211> LENGTH: 7
<212> TYPE: PRT
<213> ORGANISM: Artificial Sequence
<220> FEATURE:
<223> OTHER INFORMATION: synthetic

<400> SEQUENCE: 198

Ile Tyr Tyr Ser Gly Asn Thr
1               5

<210> SEQ ID NO 199

<211> LENGTH: 45
<212> TYPE: DNA
<213> ORGANISM: Artificial Sequence
<220> FEATURE:
<223> OTHER INFORMATION: synthetic

<400> SEQUENCE: 199
gcgagacaag gatatagtga ctacgagttg aactggttcg acccc             45

<210> SEQ ID NO 200
<211> LENGTH: 15
<212> TYPE: PRT
<213> ORGANISM: Artificial Sequence
<220> FEATURE:
<223> OTHER INFORMATION: synthetic

<400> SEQUENCE: 200

Ala Arg Gln Gly Tyr Ser Asp Tyr Glu Leu Asn Trp Phe Asp Pro
1               5                   10                  15

<210> SEQ ID NO 201
<211> LENGTH: 339
<212> TYPE: DNA
<213> ORGANISM: Artificial Sequence
<220> FEATURE:
<223> OTHER INFORMATION: synthetic

<400> SEQUENCE: 201
gacatcgtga tgacccagtc tccagactcc ctggtgctgt ctctgggcga gagggccacc     60
ttcaactgca gtccagcca gagtgtttta gacagttcca acaataagaa ctacttagct    120
tggtaccagc agaaaccagg acagcctcct aagttgctca tttactgggc atctacccgg    180
gaatccgggg tccctgaccg attcagtggc agcgggtctg ggacagattt ctctctcacc    240
atcagcagcc tgcaggctga agatgtggca ctttattact gtcaacaatt ttataatagt    300
ccgtggacgt tcggccaagg gaccaaggtg gaaatcaaa                           339

<210> SEQ ID NO 202
<211> LENGTH: 113
<212> TYPE: PRT
<213> ORGANISM: Artificial Sequence
<220> FEATURE:
<223> OTHER INFORMATION: synthetic

<400> SEQUENCE: 202

Asp Ile Val Met Thr Gln Ser Pro Asp Ser Leu Val Leu Ser Leu Gly
1               5                   10                  15

Glu Arg Ala Thr Phe Asn Cys Lys Ser Ser Gln Ser Val Leu Asp Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Ser Leu Thr
65                  70                  75                  80

Ile Ser Ser Leu Gln Ala Glu Asp Val Ala Leu Tyr Tyr Cys Gln Gln
                85                  90                  95

Phe Tyr Asn Ser Pro Trp Thr Phe Gly Gln Gly Thr Lys Val Glu Ile
                100                 105                 110

Lys

<210> SEQ ID NO 203
<211> LENGTH: 36
<212> TYPE: DNA
<213> ORGANISM: Artificial Sequence
<220> FEATURE:
<223> OTHER INFORMATION: synthetic

<400> SEQUENCE: 203
cagagtgttt tagacagttc caacaataag aactac                36

<210> SEQ ID NO 204
<211> LENGTH: 12
<212> TYPE: PRT
<213> ORGANISM: Artificial Sequence
<220> FEATURE:
<223> OTHER INFORMATION: synthetic

<400> SEQUENCE: 204

Gln Ser Val Leu Asp Ser Ser Asn Asn Lys Asn Tyr
1               5                   10

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 tgggcatct                                              9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Trp Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
caacaatttt ataatagtcc gtggacg                          27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Phe Tyr Asn Ser Pro Trp Thr
1               5

<210> SEQ ID NO 209
<211> LENGTH: 363
<212> TYPE: DNA
<213> ORGANISM: Artificial Sequence
<220> FEATURE:
<223> OTHER INFORMATION: synthetic

<400> SEQUENCE: 209

```
caggtgcagc tgcaggagtc gggcccaggg ctggtgaagc cctcggagac cctgtccctc    60
acctgcactg tctctggtgg ctccatcaat agttattctt ggacctggat ccggcagccc   120
ccagggaagg gactggaatg gattggaaat atctataata gtgagaatac caactacaac   180
ccctccctca agagtcgagt caccatatca gttgacacgt ccaagagtca ggtttccctg   240
aaactgaact ctgtgaccgc tgcggacacg gccgtatatt actgtgcgag aacatataac   300
tggaactacg aaatagggc catgggcgtc tggggccagg ggaccacggt caccgtctcc   360
tca                                                                 363
```

<210> SEQ ID NO 210
<211> LENGTH: 121
<212> TYPE: PRT
<213> ORGANISM: Artificial Sequence
<220> FEATURE:
<223> OTHER INFORMATION: synthetic

<400> SEQUENCE: 210

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Ser Trp Thr Trp Ile Arg Gln Pro Pro Gly Lys Gly Leu Glu Trp Ile
        35                  40                  45

Gly Asn Ile Tyr Asn Ser Glu Asn Thr Asn Tyr Asn Pro Ser Leu Lys
    50                  55                  60

Ser Arg Val Thr Ile Ser Val Asp Thr Ser Lys Ser Gln Val Ser Leu
65                  70                  75                  80

Lys Leu Asn Ser Val Thr Ala Ala Asp Thr Ala Val Tyr Tyr Cys Ala
                85                  90                  95

Arg Thr Tyr Asn Trp Asn Tyr Glu Ile Gly Ala Met Gly Val Trp Gly
            100                 105                 110

Gln Gly Thr Thr Val Thr Val Ser Ser
        115                 120
```

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211

```
ggtggctcca tcaatagtta ttct                                           24
```

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

```
Gly Gly Ser Ile Asn Ser Tyr Ser
1               5
```

```
<210> SEQ ID NO 213
<211> LENGTH: 21
<212> TYPE: DNA
<213> ORGANISM: Artificial Sequence
<220> FEATURE:
<223> OTHER INFORMATION: synthetic

<400> SEQUENCE: 213
atctataata gtgagaatac c                                              21

<210> SEQ ID NO 214
<211> LENGTH: 7
<212> TYPE: PRT
<213> ORGANISM: Artificial Sequence
<220> FEATURE:
<223> OTHER INFORMATION: synthetic

<400> SEQUENCE: 214

Ile Tyr Asn Ser Glu Asn Thr
1               5

<210> SEQ ID NO 215
<211> LENGTH: 45
<212> TYPE: DNA
<213> ORGANISM: Artificial Sequence
<220> FEATURE:
<223> OTHER INFORMATION: synthetic

<400> SEQUENCE: 215
gcgagaacat ataactggaa ctacgaaata ggggccatgg gcgtc                    45

<210> SEQ ID NO 216
<211> LENGTH: 15
<212> TYPE: PRT
<213> ORGANISM: Artificial Sequence
<220> FEATURE:
<223> OTHER INFORMATION: synthetic

<400> SEQUENCE: 216

Ala Arg Thr Tyr Asn Trp Asn Tyr Glu Ile Gly Ala Met Gly Val
1               5                   10                  15

<210> SEQ ID NO 217
<211> LENGTH: 339
<212> TYPE: DNA
<213> ORGANISM: Artificial Sequence
<220> FEATURE:
<223> OTHER INFORMATION: synthetic

<400> SEQUENCE: 217
gacatcgtga tgacccagtt tccagactcc ctggctgtgt ctctgggcga gagggccacc    60
atcaactgca gtccagcca gaatgtttta atcacctcca acaataagaa ttatttagct   120
tggtaccagc agaaaccagg acagcctcct aagctgctca tttactgggc ttccacccgg   180
gaattcgggg tccctgcccg attcagtggc agcgggtctg ggacagattt cactctcacc   240
atcagcagcc tgcaggctga agatgtggca gtttattact gtcagcaata ttatagtact   300
ccattcactt tcggccctgg gaccaaagtg gatatcaaa                         339

<210> SEQ ID NO 218
<211> LENGTH: 113
<212> TYPE: PRT
<213> ORGANISM: Artificial Sequence
<220> FEATURE:
<223> OTHER INFORMATION: synthetic
```

-continued

<400> SEQUENCE: 218

Asp Ile Val Met Thr Gln Phe Pro Asp Ser Leu Ala Val Ser Leu Gly
1               5                   10                  15

Glu Arg Ala Thr Ile Asn Cys Lys Ser Ser Gln Asn Val Leu Ile Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Ala Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
                100                 105                 110

Lys

<210> SEQ ID NO 219
<211> LENGTH: 36
<212> TYPE: DNA
<213> ORGANISM: Artificial Sequence
<220> FEATURE:
<223> OTHER INFORMATION: synthetic

<400> SEQUENCE: 219
cagaatgttt taatcacctc caacaataag aattat                            36

<210> SEQ ID NO 220
<211> LENGTH: 12
<212> TYPE: PRT
<213> ORGANISM: Artificial Sequence
<220> FEATURE:
<223> OTHER INFORMATION: synthetic

<400> SEQUENCE: 220

Gln Asn Val Leu Ile Thr Ser Asn Asn Lys Asn Tyr
1               5                   10

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 tgggcttcc                                                           9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Trp Ala Ser
1

<210> SEQ ID NO 223
<211> LENGTH: 27
<212> TYPE: DNA

<213> ORGANISM: Artificial Sequence
<220> FEATURE:
<223> OTHER INFORMATION: synthetic

<400> SEQUENCE: 223
cagcaatatt atagtactcc attcact                                27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Tyr Tyr Ser Thr Pro Phe Thr
1               5

<210> SEQ ID NO 225
<211> LENGTH: 363
<212> TYPE: DNA
<213> ORGANISM: Artificial Sequence
<220> FEATURE:
<223> OTHER INFORMATION: synthetic

<400> SEQUENCE: 225
caggttcagc tggtgcagtc tggagctgag gtgaagaagc ctgggacctc agtgaaggtc    60
tcctgcaagg cttctggtta cacctttacc aactatggta tcagttgggt gcgacaggcc   120
cctggacaag gtcttgagtg gttgggatgg atcagcgctt ataatgataa cacagactat   180
gcacagaaac tccaggccag agtcaccatg accacagaca cattcacgag cacagcctac   240
atggacctga ggagcctgag atctgacgac acggccgtgt attactgtgc gagagttcct   300
ataactggaa ctacctcaag ttttgacttc tggggccagg gaaccctggt caccgtctcc   360
tca                                                                 363

<210> SEQ ID NO 226
<211> LENGTH: 121
<212> TYPE: PRT
<213> ORGANISM: Artificial Sequence
<220> FEATURE:
<223> OTHER INFORMATION: synthetic

<400> SEQUENCE: 226

Gln Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Leu
        35                  40                  45

Gly Trp Ile Ser Ala Tyr Asn Asp Asn Thr Asp Tyr Ala Gln Lys Leu
    50                  55                  60

Gln Ala Arg Val Thr Met Thr Thr Asp Thr Phe Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Val Pro Ile Thr Gly Thr Thr Ser Ser Phe Asp Phe Trp Gly
            100                 105                 110

Gln Gly Thr Leu Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggttacacct ttaccaacta tggt                                        24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gly Tyr Thr Phe Thr Asn Tyr Gly
1               5

<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
atcagcgctt ataatgataa caca                                        24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Ser Ala Tyr Asn Asp Asn Thr
1               5

<210> SEQ ID NO 231
<211> LENGTH: 42
<212> TYPE: DNA
<213> ORGANISM: Artificial Sequence
<220> FEATURE:
<223> OTHER INFORMATION: synthetic

<400> SEQUENCE: 231
gcgagagttc ctataactgg aactacctca gtttttgact tc                    42

<210> SEQ ID NO 232
<211> LENGTH: 14
<212> TYPE: PRT
<213> ORGANISM: Artificial Sequence
<220> FEATURE:
<223> OTHER INFORMATION: synthetic

<400> SEQUENCE: 232

Ala Arg Val Pro Ile Thr Gly Thr Thr Ser Ser Phe Asp Phe
1               5                   10

<210> SEQ ID NO 233
<211> LENGTH: 321
<212> TYPE: DNA

<210> SEQ ID NO 233 (continued)

<213> ORGANISM: Artificial Sequence
<220> FEATURE:
<223> OTHER INFORMATION: synthetic

<400> SEQUENCE: 233

```
gacatccaga tgacccagtc tccatcctcc ctgtctgcat ctgtaggaga cagagtcacc    60
atctcttgcc gggcaagtca gaccatttac agctatttaa attggtttca gcagaaacca   120
gggaaagccc ctaagctcct gatctatgat gcatccagtt tgcaaagtgg ggtcccatca   180
aggttcagtg gcagtggctc tgggacacat ttcactctca ccatcagcag tctgcaacct   240
gaggattttg caacttactt ctgccaacag acttacagta cccctctcac tttcggcgga   300
gggaccaagg tggagatcaa a                                             321
```

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

```
Asp Ile Gln Met Thr Gln Ser Pro Ser Ser Leu Ser Ala Ser Val Gly
1               5                   10                  15
Asp Arg Val Thr Ile Ser Cys Arg Ala Ser Gln Thr Ile Tyr Ser Tyr
            20                  25                  30
Leu Asn Trp Phe Gln Gln Lys Pro Gly Lys Ala Pro Lys Leu Leu Ile
        35                  40                  45
Tyr Asp Ala Ser Ser Leu Gln Ser Gly Val Pro Ser Arg Phe Ser Gly
    50                  55                  60
Ser Gly Ser Gly Thr His Phe Thr Leu Thr Ile Ser Ser Leu Gln Pro
65                  70                  75                  80
Glu Asp Phe Ala Thr Tyr Phe Cys Gln Gln Thr Tyr Ser Thr Pro Leu
                85                  90                  95
Thr Phe Gly Gly Gly Thr Lys Val Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235

```
cagaccattt acagctat                                                  18
```

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

```
Gln Thr Ile Tyr Ser Tyr
1               5
```

<210> SEQ ID NO 237
<211> LENGTH: 9
<212> TYPE: DNA
<213> ORGANISM: Artificial Sequence

```
<220> FEATURE:
<223> OTHER INFORMATION: synthetic

<400> SEQUENCE: 237 gatgcatcc                                                              9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Asp Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
caacagactt acagtacccc tctcact                                         27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Gln Gln Thr Tyr Ser Thr Pro Leu Thr
1               5

<210> SEQ ID NO 241
<211> LENGTH: 360
<212> TYPE: DNA
<213> ORGANISM: Artificial Sequence
<220> FEATURE:
<223> OTHER INFORMATION: synthetic

<400> SEQUENCE: 241
caggtgcagc tgcaggagtc gggcccagga ctggtgaaac cttcggagac cctgtccctc      60
acctgcactg tctctggtgg ctccatcagt agttactact ggagctggat ccggcagccc     120
ccagggaagg gactggagtg gattggcttt atctattaca gtgggagcac caactacaac     180
ccctccctca gagtcgagt caccatctca gtagacacgt ccaagaacca gttctccctg     240
aagctgagtt ctgtgaccgc cgcagacacg gccgtgtatt actgtgcgag acatgacagt     300
gactacgaac tctacggtat ggacgtctgg ggccaaggga ccacggtcac cgtctcctca     360

<210> SEQ ID NO 242
<211> LENGTH: 120
<212> TYPE: PRT
<213> ORGANISM: Artificial Sequence
<220> FEATURE:
<223> OTHER INFORMATION: synthetic

<400> SEQUENCE: 242

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Asp Ser Asp Tyr Glu Leu Tyr Gly Met Asp Val Trp Gly Gln
            100                 105                 110

Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggtggctcca tcagtagtta ctac                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Gly Ser Ile Ser Ser Tyr Tyr
1               5

<210> SEQ ID NO 245
<211> LENGTH: 21
<212> TYPE: DNA
<213> ORGANISM: Artificial Sequence
<220> FEATURE:
<223> OTHER INFORMATION: synthetic

<400> SEQUENCE: 245
atctattaca gtgggagcac c                                             21

<210> SEQ ID NO 246
<211> LENGTH: 7
<212> TYPE: PRT
<213> ORGANISM: Artificial Sequence
<220> FEATURE:
<223> OTHER INFORMATION: synthetic

<400> SEQUENCE: 246

Ile Tyr Tyr Ser Gly Ser Thr
1               5

<210> SEQ ID NO 247
<211> LENGTH: 42
<212> TYPE: DNA
<213> ORGANISM: Artificial Sequence
<220> FEATURE:
<223> OTHER INFORMATION: synthetic
```

```
<400> SEQUENCE: 247
gcgagacatg acagtgacta cgaactctac ggtatggacg tc                          42

<210> SEQ ID NO 248
<211> LENGTH: 14
<212> TYPE: PRT
<213> ORGANISM: Artificial Sequence
<220> FEATURE:
<223> OTHER INFORMATION: synthetic

<400> SEQUENCE: 248

Ala Arg His Asp Ser Asp Tyr Glu Leu Tyr Gly Met Asp Val
1               5                   10

<210> SEQ ID NO 249
<211> LENGTH: 339
<212> TYPE: DNA
<213> ORGANISM: Artificial Sequence
<220> FEATURE:
<223> OTHER INFORMATION: synthetic

<400> SEQUENCE: 249
gacatcgtga tgacccagtc tccagactcc ctggctgtgt ctctgggcga gagggccacc        60
atcacctgca gtccagcca gagtatttta tacaactccg acaataagaa ctacttagct       120
tggtaccagc agaaatcagg acagcctcct aagctgctca tttcctgggc atctacccgg      180
gaatccgggg tccctgaccg tttcagtggc agcgggtctg ggacagattt cactctcacc      240
atcagcagcc tgcaggctga agatgtggca gtttattact gtcaacaata ttttttttact      300 ccattcactt tcggccctgg gaccaaagtg gatatcaaa                             339

<210> SEQ ID NO 250
<211> LENGTH: 113
<212> TYPE: PRT
<213> ORGANISM: Artificial Sequence
<220> FEATURE:
<223> OTHER INFORMATION: synthetic

<400> SEQUENCE: 250

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Ile Leu Tyr Asn
            20                  25                  30

Ser Asp Asn Lys Asn Tyr Leu Ala Trp Tyr Gln Gln Lys Ser Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Phe Thr Pro Phe Thr Phe Gly Pro Gly Thr Lys Val Asp Ile
            100                 105                 110

Lys

<210> SEQ ID NO 251
<211> LENGTH: 36
<212> TYPE: DNA
<213> ORGANISM: Artificial Sequence
<220> FEATURE:
```

<223> OTHER INFORMATION: synthetic

<400> SEQUENCE: 251
cagagtattt tatacaactc cgacaataag aactac 36

<210> SEQ ID NO 252
<211> LENGTH: 12
<212> TYPE: PRT
<213> ORGANISM: Artificial Sequence
<220> FEATURE:
<223> OTHER INFORMATION: synthetic

<400> SEQUENCE: 252

Gln Ser Ile Leu Tyr Asn Ser Asp Asn Lys Asn Tyr
1               5                   10

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 tgggcatct 9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Trp Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
caacaatatt tttttactcc attcact 27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Tyr Phe Phe Thr Pro Phe Thr
1               5

<210> SEQ ID NO 257
<211> LENGTH: 363
<212> TYPE: DNA
<213> ORGANISM: Artificial Sequence
<220> FEATURE:
<223> OTHER INFORMATION: synthetic

<400> SEQUENCE: 257

```
gaggtgcagc tggtggagtc tgggggaggc ttggtacagc ctgggggtc cctgagactc       60 tcctgtgcag cctctggatt caccttcagt aactacgaca tacactgggt ccgccaagtt     120
ccaggaaaag gtctggagtg gatctcaact attggttctg ctggtgatac attctatcca     180
ggctccgtga agggccggtt caccatctcc agagaaaatg ccaagaactc cctgtatctt     240
caaatgaaca gcctgagagc cggggactcg gctgtatatt actgtgcaag agggataac      300 tggaactacg tttcatggtt cttcgatctc tggggccgtg gcaccctggt cactgtctcc     360
tca                                                                   363
```

<210> SEQ ID NO 258
<211> LENGTH: 121
<212> TYPE: PRT
<213> ORGANISM: Artificial Sequence
<220> FEATURE:
<223> OTHER INFORMATION: synthetic

<400> SEQUENCE: 258

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Ile His Trp Val Arg Gln Val Pro Gly Lys Gly Leu Glu Trp Ile
        35                  40                  45

Ser Thr Ile Gly Ser Ala Gly Asp Thr Phe Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Ser Ala Val Tyr Tyr Cys Ala
                85                  90                  95

Arg Gly Asp Asn Trp Asn Tyr Val Ser Trp Phe Phe Asp Leu Trp Gly
            100                 105                 110

Arg Gly Thr Leu Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259

```
ggattcacct tcagtaacta cgac                                             24
```

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

```
Gly Phe Thr Phe Ser Asn Tyr Asp
1               5
```

<210> SEQ ID NO 261
<211> LENGTH: 21

<212> TYPE: DNA
<213> ORGANISM: Artificial Sequence
<220> FEATURE:
<223> OTHER INFORMATION: synthetic

<400> SEQUENCE: 261
attggttctg ctggtgatac a                                              21

<210> SEQ ID NO 262
<211> LENGTH: 7
<212> TYPE: PRT
<213> ORGANISM: Artificial Sequence
<220> FEATURE:
<223> OTHER INFORMATION: synthetic

<400> SEQUENCE: 262

Ile Gly Ser Ala Gly Asp Thr
1               5

<210> SEQ ID NO 263
<211> LENGTH: 45
<212> TYPE: DNA
<213> ORGANISM: Artificial Sequence
<220> FEATURE:
<223> OTHER INFORMATION: synthetic

<400> SEQUENCE: 263
gcaagagggg ataactggaa ctacgtttca tggttcttcg atctc                    45

<210> SEQ ID NO 264
<211> LENGTH: 15
<212> TYPE: PRT
<213> ORGANISM: Artificial Sequence
<220> FEATURE:
<223> OTHER INFORMATION: synthetic

<400> SEQUENCE: 264

Ala Arg Gly Asp Asn Trp Asn Tyr Val Ser Trp Phe Phe Asp Leu
1               5                   10                  15

<210> SEQ ID NO 265
<211> LENGTH: 321
<212> TYPE: DNA
<213> ORGANISM: Artificial Sequence
<220> FEATURE:
<223> OTHER INFORMATION: synthetic

<400> SEQUENCE: 265
gacatccagt tgacccagtc tccatccttc ctgtctacat ctgtcggaga cagagtcacc    60
atcacgtgct gggccagtca ggacatcagc agttttttag cctggtatca gcagaaacca   120
gggaaagccc ctaaactcct gatctatgct gcgtccgttt tgcaaagtgg ggtcccatca   180
aggttcagcg gcagtggatc tgggacagaa ttcactctca caatcagcag tctgcagcct   240
gaagattttg caacttatta ctgtcagcag gttaatagtt acccgatcac cttcggccaa   300
gggacacgac tggagattaa a                                             321

<210> SEQ ID NO 266
<211> LENGTH: 107
<212> TYPE: PRT
<213> ORGANISM: Artificial Sequence
<220> FEATURE:
<223> OTHER INFORMATION: synthetic -continued

<400> SEQUENCE: 266

Asp Ile Gln Leu Thr Gln Ser Pro Ser Phe Leu Ser Thr Ser Val Gly
1               5                   10                  15

Asp Arg Val Thr Ile Thr Cys Trp Ala Ser Gln Asp Ile Ser Ser Phe
            20                  25                  30

Leu Ala Trp Tyr Gln Gln Lys Pro Gly Lys Ala Pro Lys Leu Leu Ile
        35                  40                  45

Tyr Ala Ala Ser Val Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val Asn Ser Tyr Pro Ile
                85                  90                  95

Thr Phe Gly Gln Gly Thr Arg Leu Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
caggacatca gcagtttt                                                 18

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

Gln Asp Ile Ser Ser Phe
1               5

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gctgcgtcc                                                            9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Ala Ala Ser
1

<210> SEQ ID NO 271
<211> LENGTH: 27
<212> TYPE: DNA
<213> ORGANISM: Artificial Sequence

```
<220> FEATURE:
<223> OTHER INFORMATION: synthetic

<400> SEQUENCE: 271
cagcaggtta atagttaccc gatcacc                                              27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Val Asn Ser Tyr Pro Ile Thr
1               5

<210> SEQ ID NO 273
<211> LENGTH: 173
<212> TYPE: PRT
<213> ORGANISM: Artificial Sequence
<220> FEATURE:
<223> OTHER INFORMATION: hIL-25-MMH
      aa 1-145: hIL-25 (aa 33-177 of NP_073626.1)
      aa 146-173: myc-myc-hexahistidine tag

<400> SEQUENCE: 273

Tyr Ser His Trp Pro Ser Cys Cys Pro Ser Lys Gly Gln Asp Thr Ser
1               5                   10                  15

Glu Glu Leu Leu Arg Trp Ser Thr Val Pro Val Pro Pro Leu Glu Pro
            20                  25                  30

Ala Arg Pro Asn Arg His Pro Glu Ser Cys Arg Ala Ser Glu Asp Gly
        35                  40                  45

Pro Leu Asn Ser Arg Ala Ile Ser Pro Trp Arg Tyr Glu Leu Asp Arg
    50                  55                  60

Asp Leu Asn Arg Leu Pro Gln Asp Leu Tyr His Ala Arg Cys Leu Cys
65                  70                  75                  80

Pro His Cys Val Ser Leu Gln Thr Gly Ser His Met Asp Pro Arg Gly
                85                  90                  95

Asn Ser Glu Leu Leu Tyr His Asn Gln Thr Val Phe Tyr Arg Arg Pro
            100                 105                 110

Cys His Gly Glu Lys Gly Thr His Lys Gly Tyr Cys Leu Glu Arg Arg
        115                 120                 125

Leu Tyr Arg Val Ser Leu Ala Cys Val Cys Val Arg Pro Arg Val Met
    130                 135                 140

Gly Glu Gln Lys Leu Ile Ser Glu Glu Asp Leu Gly Gly Glu Gln Lys
145                 150                 155                 160

Leu Ile Ser Glu Glu Asp Leu His His His His His His
                165                 170

<210> SEQ ID NO 274
<211> LENGTH: 172
<212> TYPE: PRT
<213> ORGANISM: Artificial Sequence
<220> FEATURE:
<223> OTHER INFORMATION: MfIL-25-MMH
      aa 1-144: M.fascicularis IL-25 (aa 33-176 of
      XP_001107906.2)
      aa 145-172: myc-myc-hexahistidine tag
```

<400> SEQUENCE: 274

| | | | | | | | | | | | | | | |
|---|---|---|---|---|---|---|---|---|---|---|---|---|---|---|
Tyr Ser His Trp Pro Ser Cys Cys Pro Ser Lys Gly Tyr Pro Ser Glu
1               5                   10                  15

Glu Leu Leu Arg Trp Ser Thr Val Pro Val Pro Pro Leu Lys Pro Ala
            20                  25                  30

Ser Leu Asp Phe His Ser Val Ser Cys Arg Ala Ser Glu Asp Gly Pro
                35                  40                  45

Leu Asn Ser Arg Ala Ile Ser Pro Trp Arg Tyr Glu Leu Asp Arg Asp
        50                  55                  60

Leu Asn Arg Leu Pro Gln Asp Leu Tyr His Ala Arg Cys Leu Cys Pro
65                  70                  75                  80

His Cys Val Ser Leu Gln Thr Gly Ser His Met Asp Pro Arg Gly Asn
                85                  90                  95

Ser Glu Leu Leu Tyr His Asn Gln Thr Val Phe Tyr Arg Arg Pro Cys
                100                 105                 110

His Gly Lys Lys Gly Asn His Lys Gly Tyr Cys Leu Glu Arg Arg Leu
            115                 120                 125

Tyr Arg Val Ser Leu Ala Cys Val Cys Val Arg Pro Arg Val Met Gly
130                 135                 140

Glu Gln Lys Leu Ile Ser Glu Glu Asp Leu Gly Gly Glu Gln Lys Leu
145                 150                 155                 160

Ile Ser Glu Glu Asp Leu His His His His His
                165                 170

<210> SEQ ID NO 275
<211> LENGTH: 181
<212> TYPE: PRT
<213> ORGANISM: Artificial Sequence
<220> FEATURE:
<223> OTHER INFORMATION: mouse IL-25-MMH
      aa 1-153: Mouse IL-25 (aa 17-169 of NP_542767.1)
      aa 154-181: myc-myc-hexahistidine tag

<400> SEQUENCE: 275

Val Ser Leu Arg Ile Gln Glu Gly Cys Ser His Leu Pro Ser Cys Cys
1               5                   10                  15

Pro Ser Lys Glu Gln Glu Pro Glu Glu Trp Leu Lys Trp Ser Ser
            20                  25                  30

Ala Ser Val Ser Pro Pro Glu Pro Leu Ser His Thr His Ala Glu
                35                  40                  45

Ser Cys Arg Ala Ser Lys Asp Gly Pro Leu Asn Ser Arg Ala Ile Ser
    50                  55                  60

Pro Trp Ser Tyr Glu Leu Asp Arg Asp Leu Asn Arg Val Pro Gln Asp
65                  70                  75                  80

Leu Tyr His Ala Arg Cys Leu Cys Pro His Cys Val Ser Leu Gln Thr
                85                  90                  95

Gly Ser His Met Asp Pro Leu Gly Asn Ser Val Pro Leu Tyr His Asn
                100                 105                 110

Gln Thr Val Phe Tyr Arg Arg Pro Cys His Gly Glu Glu Gly Thr His
            115                 120                 125

Arg Arg Tyr Cys Leu Glu Arg Leu Tyr Val Ser Leu Ala Cys
130                 135                 140

Val Cys Val Arg Pro Arg Val Met Ala Glu Gln Lys Leu Ile Ser Glu
145                 150                 155                 160

```
Glu Asp Leu Gly Gly Glu Gln Lys Leu Ile Ser Glu Asp Leu His
            165                 170                 175

His His His His His
            180

<210> SEQ ID NO 276
<211> LENGTH: 181
<212> TYPE: PRT
<213> ORGANISM: Artificial Sequence
<220> FEATURE:
<223> OTHER INFORMATION: rat IL-25-MMH
      aa 1-153: Rat IL-25 (aa 17-169 of NP_001178936.1)
      aa 154-181: myc-myc-hexahistidine tag

<400> SEQUENCE: 276

Val Ser Leu Arg Ile Gln Glu Asp Cys Ser His Leu Pro Arg Cys Cys
1               5                   10                  15

Pro Ser Lys Gln Gln Glu Phe Pro Glu Glu Trp Leu Lys Trp Asn Pro
            20                  25                  30

Ala Pro Val Ser Pro Glu Pro Leu Arg His Thr His Pro Glu
        35                  40                  45

Ser Cys Arg Ala Ser Lys Asp Gly Pro Leu Asn Ser Arg Ala Ile Ser
    50                  55                  60

Pro Trp Ser Tyr Glu Leu Asp Arg Asp Leu Asn Arg Val Pro Gln Asp
65                  70                  75                  80

Leu Tyr His Ala Arg Cys Leu Cys Pro His Cys Val Ser Leu Gln Thr
                85                  90                  95

Gly Ser His Met Asp Pro Met Gly Asn Ser Val Pro Leu Tyr His Asn
            100                 105                 110

Gln Thr Val Phe Tyr Arg Arg Pro Cys His Gly Glu Gln Gly Ala His
            115                 120                 125

Gly Arg Tyr Cys Leu Glu Arg Arg Leu Tyr Arg Val Ser Leu Ala Cys
        130                 135                 140

Val Cys Val Arg Pro Arg Met Met Ala Glu Gln Lys Leu Ile Ser Glu
145                 150                 155                 160

Glu Asp Leu Gly Gly Glu Gln Lys Leu Ile Ser Glu Asp Leu His
            165                 170                 175

His His His His His
            180

<210> SEQ ID NO 277
<211> LENGTH: 1335
<212> TYPE: DNA
<213> ORGANISM: Artificial Sequence
<220> FEATURE:
<223> OTHER INFORMATION: Human IL-25 (NM_022789.3)

<400> SEQUENCE: 277
ggcttgctga aaataaaatc aggactccta acctgctcca gtcagcctgc ttccacgagg     60
cctgtcagtc agtgccccac ttgtgactga gtgtgcagtg cccagcatgt accaggtcag    120
tgcagagggc tgcctgaggg ctgtgctgag agggagagga gcagagatgc tgctgagggt    180
ggagggaggc caagctgcca ggtttggggc tgggggccaa gtggagtgag aaactgggat    240 cccagggga gggtgcagat gagggagcga cccagattag gtgaggacag ttctctcatt    300
agccttttcc tacaggtggt tgcattcttg gcaatggtca tgggaaccca cacctacagc    360
cactggccca gctgctgccc cagcaaaggg caggacacct ctgaggagct gctgaggtgg    420
```

```
agcactgtgc ctgtgcctcc cctagagcct gctaggccca accgccaccc agagtcctgt    480
agggccagtg aagatggacc cctcaacagc agggccatct cccctggag atatgagttg     540 gacagagact tgaaccggct ccccaggac ctgtaccacg cccgttgcct gtgcccgcac     600
tgcgtcagcc tacagacagg ctcccacatg gaccccggg gcaactcgga gctgctctac     660
cacaaccaga ctgtcttcta ccggcggcca tgccatggcg agaagggcac ccacaagggc    720
tactgcctgg agcgcaggct gtaccgtgtt tccttagctt gtgtgtgtgt gcggccccgt    780
gtgatgggct agccggacct gctggaggct ggtcccttt tgggaaacct ggagccaggt     840
gtacaaccac ttgccatgaa gggccaggat cccagatgc ttggccctg tgaagtgctg      900 tctggagcag caggatcccg ggacaggatg ggggctttg gggaaagcct gcacttctgc     960
acattttgaa aagagcagct gctgcttagg gccgccggaa gctggtgtcc tgtcattttc   1020
tctcaggaaa ggttttcaaa gttctgccca tttctggagg ccaccactcc tgtctcttcc   1080
tcttttccca tccctgcta ccctggccca gcacaggcac tttctagata tttccccctt    1140
gctggagaag aaagagcccc tggttttatt tgtttgttta ctcatcactc agtgagcatc   1200
tactttgggt gcattctagt gtagttacta gtcttttgac atggatgatt ctgaggagga   1260
agctgttatt gaatgtatag agatttatcc aataaatat ctttatttaa aaatgaaaaa    1320
aaaaaaaaaa aaaaa                                                    1335
```

<210> SEQ ID NO 278
<211> LENGTH: 177
<212> TYPE: PRT
<213> ORGANISM: Artificial Sequence
<220> FEATURE:
<223> OTHER INFORMATION: Human IL-25

<400> SEQUENCE: 278

```
Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly
```

ANTI-IL-25 ANTIBODIES AND USES THEREOF

CROSS-REFERENCE TO RELATED APPLICATIONS

This application is a continuation of U.S. patent application Ser. No. 15/805,584, filed Nov. 7, 2017, now U.S. Pat. No. 10,640,558, which is a divisional of U.S. patent application Ser. No. 14/861,320 filed Sep. 22, 2015, now U.S. Pat. No. 9,840,557, which claims the benefit under 35 U.S.C § 119(e) of U.S. Provisional Application No. 62/054,167, filed Sep. 23, 2014, which is herein specifically incorporated by reference in its entirety.

FIELD OF THE INVENTION

The present invention relates to antibodies, and antigen-binding fragments thereof, which specifically bind Interleukin-25 (IL-25), pharmaceutical compositions comprising the antibodies and methods of use thereof.

BACKGROUND

Interleukin-25 (IL-25) is a cytokine that is structurally related to interleukin-17 (IL-17) and is sometimes referred to as IL-17E. It is a secreted, homodimeric glycoprotein that interacts with and signals through the heterodimeric IL-17RB/IL-17RA receptor (Iwakura, et. al., (2010), Immunity, 34:149). IL-25 is produced by Th2 cells, epithelial cells, endothelial cells, alveolar macrophages, mast cells, eosinophils and basophils (Rouvier, E. et. al., (1993), J. Immunol. 150:5445-5456; Pan, G. et. al., (2001), J. Immunol. 167:6559-6567; Kim, M. et. al., (2002), Blood 100: 2330-2340). Signaling through IL-25 is associated with eosinophil recruitment, initiation of Th2 and Th9 responses and suppression of Th1 and Th17 cell responses. IL-25 induces the production of other cytokines, including IL-4, IL-5 and IL-13, in multiple tissues (Fort, M M et. al., (2001), Immunity 15:985-995).

IL-25 has been implicated in chronic inflammation associated with the gastrointestinal tract and the IL-25 gene has been identified in a chromosomal region associated with autoimmune diseases of the gut, such as inflammatory bowel disease (IBD) (Buning, C. et. al., (2003), Eur. J. Immunogenet. October; 30(5): 329-333). IL-25 has also been shown to be upregulated in samples from patients with asthma (Sherkat, R. et. al., (2014), Asia Pac. Allergy October; 4(4):212-221). Accordingly, blockade of IL-25 signaling may be useful for the treatment of various disorders associated with IL-25 activity or expression.

Anti-IL-25 antibodies are mentioned, e.g., in U.S. Pat. Nos. 8,785,605; 8,658,169 and 8,206,717; and PCT publications WO2011/123507; WO2010/038155 and WO2008/129263. Nonetheless, there is a need in the art for novel IL-25 antagonists, such as the anti-IL-25 antibodies of the present invention, for the treatment of diseases or disorders associated with IL-25 expression and/or signaling, or other conditions associated with IL-25 expression and/or signaling.

BRIEF SUMMARY OF THE INVENTION

The present invention provides isolated antibodies and antigen-binding fragments thereof that specifically bind to human interleukin-25 (IL-25).

In a first aspect, the invention provides an isolated antibody or antigen-binding fragment thereof that specifically binds human interleukin-25 (IL-25), wherein the antibody or antigen-binding fragment thereof exhibits two or more of the following characteristics:

(a) is a fully human monoclonal antibody;
(b) binds human IL-25 with a $K_D$ of less than about 120 pM as measured by surface plasmon resonance at 25° C.;
(c) binds human IL-25 with a dissociative half life (t½) of greater than about 105 minutes as measured by surface plasmon resonance at 25° C.;
(d) blocks human IL-25 signaling in cells engineered to express an IL-25 receptor (IL-17RA/IL-17RB) with an $IC_{50}$ of less than about 2.0 nM;
(e) blocks human IL-25 signaling in human peripheral blood mononuclear cells (PBMCs) with an $IC_{50}$ of less than about 16 nM;
(f) reduces circulating and/or lung IgE levels in a mammal that overexpresses IL-25;
(g) reduces goblet cell metaplasia in a mammal that overexpresses IL-25;
(h) comprises three heavy chain complementarity determining regions (HCDRs) contained within a heavy chain variable region (HCVR) comprising an amino acid sequence as set forth in Table 1; or
(i) comprises three light chain complementarity determining regions (LCDRs) contained within a light chain variable region (LCVR) comprising an amino acid sequence as set forth in Table 1.

The isolated antibodies and antigen-binding fragments of the invention are useful, inter alia, for treating diseases and disorders associated with interleukin-25 (IL-25) activity or expression.

In one embodiment, the invention provides an anti-IL-25 antibody or antigen-binding fragment thereof that specifically binds human IL-25 with a $K_D$ of less than about 100 pM as measured by surface plasmon resonance at 25° C. or 37° C.

In one embodiment, the invention provides an anti-IL-25 antibody or antigen-binding fragment thereof that specifically binds human IL-25 with a $K_D$ of less than about 60 pM as measured by surface plasmon resonance at 25° C. or 37° C.

In one embodiment, the invention provides an anti-IL-25 antibody or antigen-binding fragment thereof that specifically binds human IL-25 with a $K_D$ of less than about 40 pM as measured by surface plasmon resonance at 25° C. or 37° C.

In one embodiment, the invention provides an anti-IL-25 antibody or antigen-binding fragment thereof that specifically binds human IL-25 with a $K_D$ of less than about 20 pM as measured by surface plasmon resonance at 25° C. or 37° C.

In one embodiment, the invention provides an anti-IL-25 antibody or antigen-binding fragment thereof that specifically binds human IL-25 with a t½ of greater than about 150 minutes as measured by surface plasmon resonance at 25° C.

In one embodiment, the invention provides an anti-IL-25 antibody or antigen-binding fragment thereof that specifically binds human IL-25 with a t½ of greater than about 200 minutes as measured by surface plasmon resonance at 25° C.

In one embodiment, the invention provides an anti-IL-25 antibody or antigen-binding fragment thereof that specifically binds human IL-25 with a t½ of greater than about 250 minutes as measured by surface plasmon resonance at 25° C.

In one embodiment, the invention provides an anti-IL-25 antibody or antigen-binding fragment thereof that specifically binds human IL-25 with a t½ of greater than about 400 minutes as measured by surface plasmon resonance at 25° C.

In one embodiment, the invention provides an anti-IL-25 antibody or antigen-binding fragment thereof that specifically binds human IL-25 and blocks human IL-25 signaling in cells engineered to express an IL-25 receptor (IL-17RA/IL-17RB) with an $IC_{50}$ of less than about 720 pM.

In one embodiment, the invention provides an anti-IL-25 antibody or antigen-binding fragment thereof that specifically binds human IL-25 and blocks human IL-25 signaling in cells engineered to express an IL-25 receptor (IL-17RA/IL-17RB) with an $IC_{50}$ of less than about 500 pM.

In one embodiment, the invention provides an anti-IL-25 antibody or antigen-binding fragment thereof that specifically binds human IL-25 and blocks human IL-25 signaling in cells engineered to express an IL-25 receptor (IL-17RA/IL-17RB) with an $IC_{50}$ of less than about 100 pM.

In one embodiment, the invention provides an anti-IL-25 antibody or antigen-binding fragment thereof that specifically binds human IL-25 and blocks human IL-25 signaling in human PBMCs with an $IC_{50}$ of less than about 2.0 nM.

In one embodiment, the invention provides an anti-IL-25 antibody or antigen-binding fragment thereof that specifically binds human IL-25 and blocks human IL-25 signaling in human PBMCs with an $IC_{50}$ of less than about 700 pM.

In one embodiment, the invention provides an anti-IL-25 antibody or antigen-binding fragment thereof that specifically binds human IL-25 and blocks human IL-25 signaling in human PBMCs with an $IC_{50}$ ranging from about 30 pM to about 150 pM.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Exemplary anti-IL-25 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-IL-25 antibodies. Table 2 sets forth the nucleic acid sequence identifiers of the HCVRs, LCVRs, HCDR1, HCDR2 HCDR3, LCDR1, LCDR2 and LCDR3 of the exemplary anti-IL-25 antibodies.

The present invention provides antibodies or antigen-binding fragments thereof that specifically bind IL-25, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind IL-25, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind IL-25, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-IL-25 antibodies listed in Table 1.

An isolated antibody or antigen-binding fragment thereof that specifically binds human interleukin-25 (IL-25), wherein the antibody or antigen-binding fragment thereof comprises: (a) the complementarity determining regions (CDRs) of a heavy chain variable region (HCVR) comprising an amino acid sequence as set forth in Table 1; and (b) the CDRs of a light chain variable region (LCVR) comprising an amino acid sequence as set forth in Table 1.

In one embodiment, the isolated antibody or antigen-binding fragment thereof that specifically binds IL-25 comprises: (a) the CDRs of an HCVR having an amino acid sequence selected from the group consisting of SEQ ID NOs: 2, 18, 34, 50, 66, 82, 98, 114, 130, 146, 162, 178, 194, 210, 226, 242 and 258; and (b) the CDRs of a LCVR having an amino acid sequence selected from the group consisting of SEQ ID NOs: 10, 26, 42, 58, 74, 90, 106, 122, 138, 154, 170, 186, 202, 218, 234, 250 and 266.

In one embodiment, the isolated antibody or antigen-binding fragment thereof that specifically binds IL-25 comprises: (a) the CDRs of an HCVR having an amino acid sequence selected from the group consisting of SEQ ID NOs: 98, 114, 130 and 178; and (b) the CDRs of a LCVR having an amino acid sequence selected from the group consisting of SEQ ID NOs: 106, 122, 138 and 186.

In one embodiment, the isolated antibody or antigen-binding fragment thereof that specifically binds IL-25 comprises an HCVR amino acid sequence selected from the group consisting of SEQ ID NOs: 2, 18, 34, 50, 66, 82, 98, 114, 130, 146, 162, 178, 194, 210, 226, 242 and 258.

In one embodiment, the isolated antibody or antigen-binding fragment thereof that specifically binds IL-25 comprises an LCVR amino acid sequence selected from the group consisting of SEQ ID NOs: 10, 26, 42, 58, 74, 90, 106, 122, 138, 154, 170, 186, 202, 218, 234, 250 and 266.

In one embodiment, the isolated antibody or antigen-binding fragment thereof that specifically binds IL-25 comprises an HCVR amino acid sequence selected from the group consisting of SEQ ID NOs: 2, 18, 34, 50, 66, 82, 98, 114, 130, 146, 162, 178, 194, 210, 226, 242 and 258; and an LCVR amino acid sequence selected from the group consisting of SEQ ID NOs: 10, 26, 42, 58, 74, 90, 106, 122, 138, 154, 170, 186, 202, 218, 234, 250 and 266.

In one embodiment, the isolated antibody or antigen-binding fragment thereof that specifically binds IL-25 comprises: the CDRs of a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250 and 258/266.

In one embodiment, the isolated antibody or antigen-binding fragment thereof that specifically binds IL-25 comprises: the CDRs of a HCVR/LCVR amino acid sequence pair selected from the group consisting of SEQ ID NOs: 98/106; 114/122; 130/138; and 178/186.

In one embodiment, the isolated antibody or antigen-binding fragment thereof that specifically binds IL-25 comprises an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250 and 258/266.

In one embodiment, the isolated antibody or antigen-binding fragment thereof that specifically binds IL-25 comprises an HCVR/LCVR amino acid sequence pair selected from the group consisting of SEQ ID NOs: 98/106; 114/122; 130/138; and 178/186.

The present invention also provides antibodies or antigen-binding fragments thereof that specifically bind IL-25, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind IL-25, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-IL-25 antibodies listed in Table 1. In certain embodiments, the HCDR3/LCDR3 amino acid sequence pair is selected from the group consisting of: 104/112; 120/128; 136/144; and 184/192.

The present invention also provides antibodies or antigen-binding fragments thereof that specifically bind IL-25, comprising a set of six CDRs (i.e., HCDR1, HCDR2, HCDR3, LCDR1, LCDR2, LCDR3) contained within any of the exemplary anti-IL-25 antibodies listed in Table 1. In certain embodiments, the HCDR1, HCDR2, HCDR3, LCDR1, LCDR2, LCDR3 amino acid sequence set is selected from the group consisting of: (a) SEQ ID NOs: 100, 102, 104, 108, 110, 112; (b) SEQ ID NOs: 116, 118, 120, 124, 126, 128; (c) SEQ ID NOs: 132, 134, 136, 140, 142, 144; and (d) SEQ ID NOs: 180, 182, 184, 188, 190, 192.

In a related embodiment, the present invention provides antibodies, or antigen-binding fragments thereof that specifically bind IL-25, comprising a set of six CDRs (i.e., HCDR1, HCDR2, HCDR3, LCDR1, LCDR2, LCDR3) contained within an HCVR/LCVR amino acid sequence pair as defined by any of the exemplary anti-IL-25 antibodies listed in Table 1. For example, the present invention includes antibodies or antigen-binding fragments thereof that specifically bind IL-25, comprising the HCDR1, HCDR2, HCDR3, LCDR1, LCDR2, LCDR3 amino acid sequences set contained within an HCVR/LCVR amino acid sequence pair selected from the group consisting of: 98/106; 114/122; 130/138; and 178/186. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In one embodiment, the invention provides an isolated antibody or antigen-binding fragment thereof that specifically binds IL-25 comprising:
  (a) a HCDR1 domain having an amino acid sequence selected from the group consisting of SEQ ID NOs: 4, 20, 36, 52, 68, 84, 100, 116, 132, 148, 164, 180, 196, 212, 228, 244 and 260;
  (b) a HCDR2 domain having an amino acid sequence selected from the group consisting of SEQ ID NOs: 6, 22, 38, 54, 70, 86, 102, 118, 134, 150, 166, 182, 198, 214, 230, 246 and 262;
  (c) a HCDR3 domain having an amino acid sequence selected from the group consisting of SEQ ID NOs: 8, 24, 40, 56, 72, 88, 104, 120, 136, 152, 168, 184, 200, 216, 232, 248 and 264;
  (d) a LCDR1 domain having an amino acid sequence selected from the group consisting of SEQ ID NOs: 12, 28, 44, 60, 76, 92, 108, 124, 140, 156, 172, 188, 204, 220, 236, 252 and 268;
  (e) a LCDR2 domain having an amino acid sequence selected from the group consisting of SEQ ID NOs: 14, 30, 46, 62, 78, 94, 110, 126, 142, 158, 174, 190, 206, 222, 238, 254 and 270; and
  (f) a LCDR3 domain having an amino acid sequence selected from the group consisting of SEQ ID NOs: 16, 32, 48, 64, 80, 96, 112, 128, 144, 160, 176, 192, 208, 224, 240, 256 and 272.

In one embodiment, the invention provides an isolated antibody or antigen-binding fragment thereof that specifically binds IL-25 comprising:
  (a) a HCDR1 domain having an amino acid sequence selected from the group consisting of SEQ ID NOs: 100, 116, 132, and 180;

(b) a HCDR2 domain having an amino acid sequence selected from the group consisting of SEQ ID NOs: 102, 118, 134, and 182;

(c) a HCDR3 domain having an amino acid sequence selected from the group consisting of SEQ ID NOs: 104, 120, 136, and 184;

(d) a LCDR1 domain having an amino acid sequence selected from the group consisting of SEQ ID NOs: 108, 124, 140, and 188;

(e) a LCDR2 domain having an amino acid sequence selected from the group consisting of SEQ ID NOs: 110, 126, 142, and 190; and (f) a LCDR3 domain having an amino acid sequence selected from the group consisting of SEQ ID NOs: 112, 128, 144, and 192.

In one embodiment, the invention provides an isolated antibody or antigen-binding fragment thereof that comprises a set of six CDRs selected from the group consisting of: (a) SEQ ID NOs: 100, 102, 104, 108, 110, 112; (b) SEQ ID NOs: 116, 118, 120, 124, 126, 128; (c) SEQ ID NOs: 132, 134, 136, 140, 142, 144; and (d) SEQ ID NOs: 180, 182, 184, 188, 190, 192.

In one embodiment, the invention provides an isolated antibody or antigen-binding fragment thereof that binds human interleukin-25 (IL-25), wherein the antibody or antigen-binding fragment thereof competes for binding to human IL-25 with a reference antibody comprising a heavy chain variable region/light chain variable region (HCVR/LCVR) amino acid sequence pair as set forth in Table 1. The reference antibody may comprise an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250 and 258/266.

In one embodiment, the invention provides an isolated antibody or antigen-binding fragment thereof that binds human interleukin-25 (IL-25), wherein the antibody or antigen-binding fragment thereof binds to the same epitope on human IL-25 as a reference antibody comprising a heavy chain variable region/light chain variable region (HCVR/LCVR) amino acid sequence pair as set forth in Table 1. The reference antibody may comprise an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250 and 258/266.

In a second aspect, the present invention provides nucleic acid molecules encoding anti-IL-25 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-IL-25 antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-IL-25 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-IL-25 antibody listed in Table 1.

In a third aspect, the present invention provides recombinant expression vectors capable of expressing a polypeptide comprising a heavy or light chain variable region of an anti-IL-25 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-IL-25 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention provides a pharmaceutical composition comprising at least one antibody of the invention, or an antigen binding fragment thereof, which specifically binds IL-25 and a pharmaceutically acceptable carrier.

In a related aspect, the invention features a composition, which is a combination of an anti-IL-25 antibody and a second therapeutic agent. In one embodiment, the second therapeutic agent is any agent that is advantageously combined with an anti-IL-25 antibody. The second therapeutic agent may be useful for alleviating the inflammatory disease or disorder, or at least one symptom of the inflammatory disease or disorder.

In certain embodiments, the second therapeutic agent may be selected from the group consisting of a non-steroidal anti-inflammatory (NSAID), a steroid, a corticosteroid (inhaled or topical), an immunosuppressant (e.g. cyclophosphamide), an anticholinergic agent (e.g. tiotropium), a muscarinic agent (e.g. glycopyrronium), a phosphodiesterase inhibitor (e.g. theophylline, roflumilast, cilomilast), a beta blocker, cyclosporine, tacrolimus, pimecrolimus, azathioprine, methotrexate, cromolyn sodium, a proteinase inhibitor, a bronchial dilator, a beta-2-agonist, an antihistamine, epinephrine, a decongestant, a leukotriene inhibitor, a mast cell inhibitor, a thymic stromal lymphopoietin (TSLP) antagonist, a TNF antagonist, an IgE antagonist, an IL-1 antagonist, an IL-4 or IL-4R antagonist, an IL-13 or IL-13R antagonist, an IL-4/IL-13 dual antagonist, an IL-5 antagonist, an IL-6 or IL-6R antagonist, an antagonist of IL-8, an IL-9 antagonist, an IL-12/23 antagonist, an IL-22 antagonist, an IL-17 antagonist, an IL-31 antagonist, an IL-33 antagonist, a Thymic Stromal Lymphopoietin Protein (TSLP) antagonist, an oral PDE4 inhibitor, and a different antibody to IL-25.

In a fifth aspect, the invention provides therapeutic methods for treating a disease or disorder associated with IL-25 activity or expression, or at least one symptom associated with the disease or disorder, using an anti-IL-25 antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by targeting IL-25 and/or by inhibiting IL-25-mediated cell signaling.

In certain embodiments, the disease or disorder to be treated with an anti-IL-25 antibody of the invention, or an antigen-binding portion thereof, may be selected from the group consisting of asthma, allergy, allergic rhinitis, allergic airway inflammation, autoimmune diseases, chronic obstructive pulmonary disease (COPD), eosinophilic pneumonia, eosinophilic esophagitis, hypereosinophilic syndrome, graft-versus-host disease, atopic dermatitis (AD), urticaria, including chronic idiopathic urticaria, psoriasis, inflammatory bowel disease (IBD), arthritis, uveitis, cardiovascular disease, pain, multiple sclerosis, lupus, vasculitis, and Eosinophilic Granulomatosis with Polyangiitis ((EGPA), also known as Churg-Strauss Syndrome).

In one embodiment, the asthma that may be treated by an antibody of the invention, or an antigen-binding fragment thereof may be selected from the group consisting of allergic asthma, non-allergic asthma, severe refractory asthma, asthma exacerbations, viral induced asthma, or viral induced asthma exacerbations, steroid resistant asthma, steroid sensitive asthma, eosinophilic asthma or non-eosinophilic asthma and other related disorders characterized by airway inflammation or airway hyperresponsiveness (AHR).

In one embodiment, the COPD that may be treated by an antibody of the invention, or an antigen-binding fragment thereof is associated in part with, or caused by, cigarette smoke, air pollution, occupational chemicals, allergy or airway hyperresponsiveness.

In one embodiment, the AD that may be treated by an antibody of the invention, or an antigen-binding fragment thereof is associated in part with, or caused by epidermal barrier dysfunction, allergy, or radiation exposure.

An allergy that may be treated by an antibody of the invention, or an antigen binding fragment thereof may be due to certain foods, pollen, mold, dust mites, animals, or animal dander.

In one embodiment, the IBD that may be treated by an antibody of the invention, or an antigen-binding fragment thereof may be selected from the group consisting of ulcerative colitis, Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

In one embodiment, the arthritis that may be treated by an antibody of the invention, or an antigen-binding fragment thereof may be selected from the group consisting of osteoarthritis (OA), rheumatoid arthritis and psoriatic arthritis.

Other embodiments will become apparent from a review of the ensuing detailed description.

BRIEF DESCRIPTION OF THE FIGURES

FIG. 1. Cross Competition between Anti-IL-25 Antibodies for Human IL-25.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "interleukin-25", "IL-25," and the like, also known as "IL-17E", refers to the human cytokine (unless designated as being from another species) comprising the amino acid sequence as set forth in amino acid residues 33 through 177 of accession number NP_073626.1. Human IL-25 containing a myc-myc-hexahistidine tag is shown as SEQ ID NO: 273 (with amino acid residues 1-145 being human IL-25 without the signal sequence and amino acid residues 146-173 the myc-myc-hexahistidine tag). Additional IL-25 proteins are described herein, including monkey IL-25 (amino acids 33-176 of accession number XP_001107906.2) containing a myc-myc-hexahistidine tag, which is shown as SEQ ID NO: 274 (with amino acid residues 1-144 being *M. fascicularis* IL-25 and amino acid residues 145-172 the myc-myc-hexahistidine tag); mouse IL-25 (amino acids 17-169 of accession number NP_542767.1) containing a myc-myc-hexahistidine tag, which is shown as SEQ ID NO: 275 (with amino acid residues 1-153 being mouse IL-25 and amino acid residues 154-181 the myc-myc-hexahistidine tag); and rat IL-25 (amino acid residues 17-169 of accession number NP_001178936.1) containing a myc-myc-hexahistidine tag, which is shown as SEQ ID NO: 276 (with amino acid residues 1-153 being rat IL-25 and amino acid residues 154-181 the myc-myc-hexahistidine tag.

All references to proteins, polypeptides and protein fragments herein are intended to refer to the human version of the respective protein, polypeptide or protein fragment unless explicitly specified as being from a non-human species. Thus, the expression "IL-25" means human IL-25 unless specified as being from a non-human species, e.g., "monkey IL-25," "mouse IL-25," "rat IL-25," etc.

As used herein, the expression "anti-IL-25 antibody" includes both monovalent antibodies with a single specificity, as well as bispecific antibodies comprising a first arm that binds IL-25 and a second arm that binds a second (target) antigen, wherein the anti-IL-25 arm comprises any of the HCVR/LCVR or CDR sequences as set forth in Table 1 herein. The expression "anti-IL-25 antibody" also includes antibody-drug conjugates (ADCs) comprising an anti-IL-25 antibody or antigen-binding portion thereof conjugated to a drug or toxin (i.e., cytotoxic agent). The expression "anti-IL-25 antibody" also includes antibody-radionuclide conjugates (ARCs) comprising an anti-IL-25 antibody or antigen-binding portion thereof conjugated to a radionuclide.

The term "anti-IL-25 antibody", as used herein, means any antigen-binding molecule or molecular complex comprising at least one complementarity determining region (CDR) that specifically binds to or interacts with IL-25 or a portion of IL-25. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-25 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full length antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function by blocking or otherwise interfering with the interaction between IL-25 and one or more of its receptor component(s). Alternatively, the antibodies of the invention may inhibit IL-25-mediated signaling through a mechanism that does not involve blocking the IL-25 interaction with its receptor. In yet other embodiments, the antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies of the invention may, in some embodiments, be recombinant and/or non-naturally occurring human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region, which may be desirable, for example, in production, to improve the yield of the desired antibody form.

The term "specifically binds", or "binds specifically to", or the like, means that an antibody or antigen-binding fragment thereof forms a complex with an antigen that is relatively stable under physiologic conditions. Specific binding can be characterized by an equilibrium dissociation constant of at least about 1×10$^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to IL-25. Moreover, multi-specific antibodies that bind to IL-25 protein and one or more additional antigens or a bi-specific that binds to two different regions of IL-25 are nonetheless considered antibodies that "specifically bind", as used herein.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-IL-25 antibodies disclosed herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-IL-25 antibodies comprising variants of any of the HCVR, LCVR, and/or CDR amino acid sequences disclosed herein having one or more conservative substitutions. For example, the present invention includes anti-IL-25 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-IL-25 antibodies with pH-dependent binding characteristics. For example, an anti-IL-25 antibody of the present invention may exhibit reduced binding to IL-25 at acidic pH as compared to neutral pH. Alternatively, anti-IL-25 antibodies of the invention may exhibit enhanced binding to IL-25 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-25 at acidic pH as compared to neutral pH" is expressed in terms of a ratio of the $K_D$ value of the antibody binding to IL-25 at acidic pH to the $K_D$ value of the antibody binding to IL-25 at neutral pH (or vice versa). For example, an antibody or antigen-binding fragment thereof may be regarded as exhibiting "reduced binding to IL-25 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Anti-IL-25 Antibodies Comprising Fc Variants

According to certain embodiments of the present invention, anti-IL-25 antibodies are provided comprising an Fc domain comprising one or more mutations which enhance or diminish antibody binding to the FcRn receptor, e.g., at acidic pH as compared to neutral pH. For example, the present invention includes anti-IL-25 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-IL-25 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

The present invention includes anti-IL-25 antibodies that bind human IL-25 with a $K_D$ of less than about 120 pM as measured by surface plasmon resonance at 25° C. According to certain embodiments, the invention includes anti-IL-25 antibodies that bind human IL-25 with a $K_D$ of less than about 100 pM, less than about 90 pM, less than about 80 pM, less than about 70 pM, less than about 60 pM, less than about 50 pM, less than about 40 pM, less than about 30 pM, less than about 20 pM, less than about 18 pM, less than about 16 pM, less than about 14 pM, or less than about 12 pM.

The present invention includes anti-IL-25 antibodies that bind human IL-25 with a dissociative half life (t½) of greater than about 105 minutes as measured by surface plasmon resonance at 25° C. According to certain embodiments, the invention includes anti-IL-25 antibodies that bind human IL-25 with a t½ of greater than about 105 minutes, greater than about 150 minutes, greater than about 175 minutes, greater than about 200 minutes, greater than about 250 minutes, greater than about 300 minutes, greater than about 350 minutes, greater than about 400 minutes, greater than about 450 minutes, greater than about 500 minutes, greater than about 550 minutes, greater than about 600 minutes, greater than about 700 minutes, greater than about 800 minutes, greater than about 900 minutes, greater than about 1000 minutes, greater than about 1100 minutes, or greater than about 1200 minutes.

The present invention includes anti-IL-25 antibodies that may or may not bind monkey IL-25, or mouse or rat IL-25. As used herein, an antibody "does not bind" a particular antigen (e.g., monkey, mouse or rat IL-25) if the antibody, when tested in an antigen binding assay such as surface plasmon resonance exhibits a $K_D$ of greater than about 1000 nM, or does not exhibit any antigen binding, in such an assay. Another assay format that can be used to determine whether an antibody binds or does not bind a particular antigen, according to this aspect of the invention, is ELISA.

The present invention includes anti-IL-25 antibodies that block human IL-25 signaling in cells engineered to express an IL-25 receptor (IL-17RA/IL-17RB) with an $IC_{50}$ of less than about 2.0 nM. For example, as shown in Example 6 herein, HEK293 cells were engineered to stably express human IL-17RA (amino acids 1 through 866 of accession number NP_055154.3) and IL-17RB (amino acids 1 through 502 of accession number NP_061195.2). The cell line can also include a reporter element that allows for the detection of IL-25-mediated signaling through the IL-17RA/IL-17RB receptor (e.g., a luciferase reporter or other detectable reporter that is induced by IL-25 binding to its receptor). Using an assay format described in Example 6, or a substantially similar assay format, an $IC_{50}$ value can be calculated as the concentration of antibody required to reduce IL-25-mediated signaling to 50% of the maximal signal observed in the absence of antibody. Thus, according to certain embodiments, the invention includes anti-IL-25 antibodies that block human IL-25 signaling in cells engineered to express an IL-25 receptor (IL-17RA/IL-17RB) with an $IC_{50}$ of less than about 720 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, or less than about 5 pM, as measured using the assay format described in Example 6 herein or a substantially similar assay.

The present invention includes anti-IL-25 antibodies that block human IL-25 signaling in human peripheral blood mononuclear cells (PBMCs) with an $IC_{50}$ of less than about 16 nM. For example, as shown in Example 7 herein, isolated PBMCs were incubated with IL-25 and various amounts of anti-IL-25 antibodies, and the level of IL-5 produced by the cells was detected to indicate the extent of IL-25-mediated signaling. Using the assay format described in Example 7, or a substantially similar assay format, an $IC_{50}$ value can be calculated as the concentration of antibody required to reduce IL-25-mediated signaling to 50% of the maximal signal observed in the absence of antibody. Thus, according to certain embodiments, the invention includes anti-IL-25 antibodies that block human IL-25 signaling in PBMCs with an $IC_{50}$ of less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured using the assay format described in Example 7 herein or a substantially similar assay. In one embodiment, the IL-25 antibodies of the invention block human IL-25 signaling in human PBMCs with an $IC_{50}$ ranging from about 30 pM to about 150 pM.

A binding characteristic of an antibody of the invention (e.g., any of the binding characteristics mentioned herein above), when disclosed in term of being "measured by surface plasmon resonance" means that the relevant binding characteristic pertaining to the interaction between the antibody and the antigen are measured using a surface plasmon resonance instrument (e.g., a Biacore® instrument, GE Healthcare) using standard Biacore assay conditions as illustrated in Example 2 herein, or substantially similar assay format. In certain embodiments, the binding parameters are measured at 25° C., while in other embodiments, the binding parameters are measured at 37° C.

The present invention includes anti-IL-25 antibodies that reduce circulating IgE levels and/or IgE levels found in the lungs of a mammal that overexpresses IL-25, as shown in the model described in Example 8. Also described herein in Example 8 are anti-IL-25 antibodies that reduce goblet cell metaplasia in a mammal that overexpresses IL-25.

The present invention includes antibodies or antigen-binding fragments thereof that specifically bind IL-25, comprising an HCVR and/or an LCVR comprising an amino acid sequence selected from any of the HCVR and/or LCVR amino acid sequences listed in Table 1.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of an IL-25 protein. Alternatively, the epitope may consist of a plurality of non-contiguous amino acids (or amino acid sequences) of IL-25. In some embodiments, the epitope is located on or near a surface of IL-25 that interacts with an IL-25 receptor. In other embodiments, the epitope is located on or near a surface of IL-25 that does not interact with an IL-25 receptor, e.g., at a location on the surface of IL-25 at which an antibody, when bound to such an epitope, does not interfere with the interaction between IL-25 and its receptor.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention includes anti-IL-25 antibodies that bind to the same epitope as any of the specific exemplary antibodies described herein (e.g. antibodies comprising any of the amino acid sequences as set forth in Table 1 herein). Likewise, the present invention also includes anti-IL-25 antibodies that compete for binding to IL-25 with any of the specific exemplary antibodies described herein (e.g. antibodies comprising any of the amino acid sequences as set forth in Table 1 herein).

One can easily determine whether an antibody binds to the same epitope as, or competes for binding with, a reference anti-IL-25 antibody by using routine methods known in the art and exemplified herein. For example, to determine if a test antibody binds to the same epitope as a reference anti-IL-25 antibody of the invention, the reference antibody is allowed to bind to an IL-25 protein. Next, the ability of a test antibody to bind to the IL-25 molecule is assessed. If the test antibody is able to bind to IL-25 following saturation binding with the reference anti-IL-25 antibody, it can be concluded that the test antibody binds to a different epitope than the reference anti-IL-25 antibody. On the other hand, if the test antibody is not able to bind to the IL-25 molecule following saturation binding with the reference anti-IL-25 antibody, then the test antibody may bind to the same epitope as the epitope bound by the reference anti-IL-25 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-IL-25 antibody, the above-described binding methodology is performed in two orientations: In a first orientation, the reference antibody is allowed to bind to an IL-25 protein under saturating conditions followed by assessment of binding of the test antibody to the IL-25 molecule. In a second orientation, the test antibody is allowed to bind to an IL-25 molecule under saturating conditions followed by assessment of binding of the reference antibody to the IL-25 molecule. If, in both orientations, only the first (saturating) antibody is capable of binding to the IL-25 molecule, then it is concluded that the test antibody and the reference antibody compete for binding to IL-25 (see, e.g., the assay format described in Example 4 herein, in which IL-25 protein is captured onto sensor tips and the IL-25-coated sensor tips are treated with a reference antibody [mAb-1] and a test anti-IL-25 antibody [mAb-2] sequentially and in both binding orders). As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-IL-25 antibodies of the present invention can be fully human but non-naturally occurring, antibodies. Methods for generating monoclonal antibodies, including fully human monoclonal antibodies are known in the art. Any such known methods can be used in the context of the present invention to make human antibodies that specifically bind to human IL-25.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to an allergen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

As described in the experimental section below, the high affinity chimeric antibodies, which are isolated having a human variable region and a mouse constant region, are characterized and selected for desirable characteristics, including affinity, selectivity, epitope, etc. The mouse constant regions are then replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase.

Bioequivalents

The anti-IL-25 antibodies and antibody fragments of the present invention encompass proteins having amino acid sequences that vary from those of the described antibodies but that retain the ability to bind human IL-25. Such variant antibodies and antibody fragments comprise one or more additions, deletions, or substitutions of amino acids when compared to parent sequence, but exhibit biological activity that is essentially equivalent to that of the described antibodies. Likewise, the anti-IL-25 antibody-encoding DNA sequences of the present invention encompass sequences that comprise one or more additions, deletions, or substitutions of nucleotides when compared to the disclosed sequence, but that encode an anti-IL-25 antibody or antibody fragment that is essentially bioequivalent to an anti- IL-25 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-IL-25 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-IL-25 antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-IL-25 antibodies that bind to human IL-25 but not to IL-25 from other species. The present invention also includes anti-IL-25 antibodies that bind to human IL-25 and to IL-25 from one or more non-human species. For example, the anti-IL-25 antibodies of the invention may bind to human IL-25 and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee IL-25. According to certain exemplary embodiments of the present invention, anti-IL-25 antibodies are provided which specifically bind human IL-25 and cynomolgus monkey (e.g., *Macaca fascicularis*) IL-25. Other anti-IL-25 antibodies of the invention bind human IL-25 but do not bind, or bind only weakly, to cynomolgus monkey IL-25.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-IL-25 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human IL-25, and the other arm of the immunoglobulin is specific for a second antigen. The IL-25-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-IL-25 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-IL-25 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to, the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-IL-25 antibody. The therapeutic composition can comprise any of the anti-IL-25 antibodies or antigen-binding fragments thereof disclosed herein, and a pharmaceutically acceptable carrier or diluent.

The antibodies of the invention are useful, inter alia, for the treatment, prevention and/or amelioration of any disease or disorder associated with or mediated by IL-25 expression or activity, or treatable by blocking the interaction between IL-25 and an IL-25 receptor, or otherwise inhibiting IL-25 activity and/or signaling.

The present invention includes methods of treating or preventing asthma by administering to a patient in need of such treatment an anti-IL-25 antibody or antigen-binding fragment thereof as disclosed elsewhere herein. As used herein, the term "asthma" includes, but is not limited to, allergic asthma, non-allergic asthma, severe refractory asthma, asthma exacerbations, viral induced asthma, or viral induced asthma exacerbations, steroid resistant asthma, steroid sensitive asthma, eosinophilic asthma or non-eosinophilic asthma, etc, and other related disorders characterized by airway inflammation or airway hyperresponsiveness (AHR). The term is also meant to include viral induced asthma exacerbation.

The present invention includes methods of treating or preventing chronic obstructive pulmonary disease (COPD) by administering to a patient in need of such treatment an anti-IL-25 antibody or antigen-binding fragment thereof as disclosed elsewhere herein. As used herein, the term "COPD" includes, but is not limited to, diseases and disorders characterized by a reduction in expiratory flow and slow forced emptying of the lungs that does not change markedly over several months. The methods according to this aspect of the present invention can be used to treat, e.g., COPD associated with or caused by cigarette smoking (e.g., long-term cigarette smoking), air pollution (e.g., sulfur dioxide, second-hand smoke, etc.), occupational chemicals (e.g., cadmium), allergy or AHR.

The present invention also includes methods of treating or preventing inflammatory bowel disease (IBD) by administering to a patient in need of such treatment an anti-IL-25 antibody or antigen-binding fragment thereof as disclosed elsewhere herein. As used herein, the term "IBD" includes, but is not limited to, ulcerative colitis, Crohn's disease, collagenous colitis, lymphocytic colitis, ischemic colitis, diversion colitis, Behcet's syndrome, infective colitis, indeterminate colitis, and other related disorders characterized by inflammation of the mucosal layer of the large intestine or colon.

The present invention also includes methods of treating or preventing atopic dermatitis (AD) by administering to a patient in need of such treatment an anti-IL-25 antibody or antigen-binding fragment thereof as disclosed elsewhere herein. As used herein, the term "AD" includes, but is not limited to, inflammatory skin diseases characterized by intense pruritus (e.g., severe itch) and by scaly and dry eczematous lesions. The term "AD" includes AD caused by or associated with epidermal barrier dysfunction, allergy (e.g., allergy to certain foods, pollen, mold, dust mite, animals, etc.), radiation exposure, and/or asthma. The methods according to this aspect of the present invention can be used to treat, e.g., mild, moderate, moderate-to-severe, and severe forms of AD.

The present invention also includes methods of treating or preventing diseases and disorders such as Eosinophilic Granulomatosis with Polyangiitis or EGPA (also known as Churg-Strauss Syndrome), allergy, allergic rhinitis, allergic airway inflammation, food hypersensitivity, urticaria (including chronic idiopathic urticaria) eosinophilic pneumonia, eosinophilic esophagitis, hypereosinophilic syndrome, idiopathic pulmonary fibrosis, hypersensitivity pneumonitis, rheumatoid arthritis, vasculitis, uveitis, cancer, and graft-versus-host-disease, by administering to a patient in need of such treatment an anti-IL-25 antibody or antigen-binding fragment thereof as disclosed elsewhere herein.

The present invention also provides methods for treating other inflammatory disorders, cardiovascular disease, central nervous system disease, pain, arthritis (e.g., rheumatoid arthritis, osteoarthritis, psoriatic arthritis, etc.), giant cell arteritis, vasculitis, general vascular disorders, Henoch-Schonlein purpura, multiple sclerosis, lupus, and sjogren's syndrome.

In the context of the methods of treatment described herein, the anti-IL-25 antibody may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-IL-25 antibodies described herein in combination with one or more additional therapeutically active components, and methods of treatment comprising administering such combinations to subjects in need thereof.

The anti-IL-25 antibodies of the present invention may be co-formulated with and/or administered in combination with one or more additional therapeutically active component(s) selected from the group consisting of, e.g., an IL-4 or IL-4R antagonist, for example, an anti-IL-4, or an anti-IL-4R antibody, an IL-13 antagonist, such as, for example, an anti-IL-13 or an anti-IL-13R antibody, an IL-6 or an IL-6R antagonist, such as, for example, an anti-IL-6 or anti-IL-6R antibody (See for example U.S. Pat. No. 7,582,298), an anti-IL-1 antagonist, e.g. rilonacept, a TNF antagonist, e.g. etanercept (ENBREL™), an IgE antagonist, and an IL-5, IL-8, IL-9, IL-17, IL-17Ra, IL-22, TSLP, and IL-33 antagonist.

In the context of treating asthma and related conditions, the additional therapeutically active component may be selected from the group consisting of: long-acting beta2-agonists (LABA, e.g., salmeterol or formoterol), inhaled corticosteroids (ICS, e.g., fluticasone or budesonide), a combination comprising a LABA+an ICS (e.g., fluticasone+salmeterol [e.g., ADVAIR® (GlaxoSmithKline)]; or budesonide+formoterol [e.g., SYMBICORT® (AstraZeneca)]), a systemic corticosteroid (e.g., oral or intravenous), methylxanthine, nedocromil sodium, cromolyn sodium, an antagonist (e.g. an antibody) to any one or more of the following cytokines and/or their receptors: IL-4, IL-5, IL-8, IL-9, IL-13, IL-17, IL-33, TSLP and combinations thereof.

In the context of treating atopic dermatitis and related conditions, the additional therapeutically active component may be selected from the group consisting of: topical corticosteroids (TCS, e.g., hydrocortisone, betamethasone valerate, betamethasone dipropionate, diflucortolone valerate, hydrocortisone-17-butyrate, mometasone furoate, methylprednisolone aceponate, clobetasol propionate, halcinonide, clobetasone butyrate, and triamcinolone acetonide), tacrolimus, pimecrolimus, cyclosporine, azathioprine, methotrexate, cromolyn sodium, proteinase inhibitors, an antagonist (e.g. an antibody) to any one or more of the following cytokines and/or their receptors: IL-4, IL-5, IL-13, IL-17, IL-33, TSLP and combinations thereof. According to certain embodiments of this aspect of the invention, the anti-IL-25 antibody is administered to a subject in conjunction with a non-pharmaceutical therapy such as ultraviolet (UV) light therapy.

In the context of treating chronic obstructive pulmonary disease (COPD), the additional therapeutically active component may be selected from a beta2 agonist, an anticholinergic agent, an IL-5 antibody (e.g. mepolizumab), or an IL-13 antibody (e.g. lebrukuzimab). For example, agents that may be used in combination with the antibodies of the invention to treat COPD may include any one or more of the following: indacaterol (a beta2 agonist), glycopyrronium (a muscarinic agent), tiotropium (an anticholinergic), aclidinium (an antimuscarinic agent), umeclidinium bromide (an anticholinergic), or vilanterol (a long acting beta2 agonist). Other agents that may be used in combination with an antibody of the invention to treat COPD include a phosphodiesterase inhibitor (e.g. theophylline, roflumilast, cilomilast), an endogenous opioid, or a beta-adrenergic antagonist (beta blockers).

In the context of treating vasculitis, in particular, Churg-Strauss Syndrome (CSS), the additional therapeutically active component may be selected from a steroid, corticosteroid and an immunosuppressant (e.g. cyclophosphamide).

In the context of treating allergies, the anti-IL-25 antibodies of the invention may be used in conjunction with any palliative therapy used to treat an allergic response, or may be used with standard immunotherapy (SIT) to treat the allergic condition, or may be used to ameliorate at least one symptom associated with the allergic response. For example, the additional therapeutically active component may be selected from an antihistamine, a steroid, a corticosteroid, a decongestant, a leukotriene inhibitor, and a mast cell inhibitor. Other agents that may be used in conjunction with an anti-IL-25 antibody of the invention to treat an allergy may be an antagonist to any one or more of the following cytokines and/or their receptors: IL-1, IL-4, IL-5, IL-8. IL-9, IL-13, IL-17, TSLP, IL-33, or a TNF antagonist.

The anti-IL-25 antibodies of the invention may also be administered and/or co-formulated in combination with antivirals, antibiotics, analgesics, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-IL-25 antibody of the present invention; (for purposes of the present disclosure, such administration regimens are considered the administration of an anti-IL-25 antibody "in combination with" an additional therapeutically active component). The present invention includes pharmaceutical compositions in which an anti-IL-25 antibody of the present invention is co-formulated with one or more of the additional therapeutically active component(s) as described elsewhere herein.

Administration Regimens

According to certain embodiments of the present invention, multiple doses of an anti-IL-25 antibody (or a pharmaceutical composition comprising a combination of an anti-IL-25 antibody and any of the additional therapeutically active agents mentioned herein) may be administered to a subject over a defined time course. The methods according to this aspect of the invention comprise sequentially administering to a subject multiple doses of an anti-IL-25 antibody of the invention. As used herein, "sequentially administering" means that each dose of anti-IL-25 antibody is administered to the subject at a different point in time, e.g., on different days separated by a predetermined interval (e.g., hours, days, weeks or months). The present invention includes methods which comprise sequentially administering to the patient a single initial dose of an anti-IL-25 antibody, followed by one or more secondary doses of the anti-IL-25 antibody, and optionally followed by one or more tertiary doses of the anti-IL-25 antibody.

The terms "initial dose," "secondary doses," and "tertiary doses," refer to the temporal sequence of administration of the anti-IL-25 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-IL-25 antibody, but generally may differ from one another in terms of frequency of administration. In certain embodiments, however, the amount of anti-IL-25 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-IL-25 antibody, which is administered to a patient prior to the administration of the very next dose in the sequence with no intervening doses.

The methods according to this aspect of the invention may comprise administering to a patient any number of secondary and/or tertiary doses of an anti-IL-25 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-IL-25 antibodies of the present invention may also be used to detect and/or measure IL-25, or IL-25-expressing cells in a sample, e.g., for diagnostic purposes. For example, an anti-IL-25 antibody, or fragment thereof, may be used to diagnose a condition or disease characterized by aberrant expression (e.g., over-expression, under-expression, lack of expression, etc.) of IL-25. Exemplary diagnostic assays for IL-25 may comprise, e.g., contacting a sample, obtained from a patient, with an anti-IL-25 antibody of the invention, wherein the anti-IL-25 antibody is labeled with a detectable label or reporter molecule. Alternatively, an unlabeled anti-IL-25 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure IL-25 in a sample include enzyme-linked immunosorbent assay (ELISA), radioimmunoassay (RIA), and fluorescence-activated cell sorting (FACS).

Samples that can be used in IL-25 diagnostic assays according to the present invention include any tissue or fluid sample obtainable from a patient which contains detectable quantities of IL-25 protein, or fragments thereof, under normal or pathological conditions. Generally, levels of IL-25 in a particular sample obtained from a healthy patient (e.g., a patient not afflicted with a disease or condition associated with abnormal IL-25 levels or activity) will be measured to initially establish a baseline, or standard, level of IL-25. This baseline level of IL-25 can then be compared against the levels of IL-25 measured in samples obtained from individuals suspected of having a IL-25 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-IL-25 Antibodies

Anti-IL-25 antibodies were obtained by immunizing a VELOCIMMUNE® mouse (i.e., an engineered mouse comprising DNA encoding human immunoglobulin heavy and kappa light chain variable regions) with recombinant human IL-25 (R & D Systems, Catalog No. 1258). The antibody immune response was monitored by an IL-25-specific immunoassay. When a desired immune response was achieved splenocytes were harvested and fused with mouse myeloma cells to preserve their viability and form hybridoma cell lines. The hybridoma cell lines were screened and selected to identify cell lines that produce IL-25-specific antibodies. Using this technique several anti-IL-25 chimeric antibodies (i.e., antibodies possessing human variable domains and mouse constant domains) were obtained. In addition, several fully human anti-IL-25 antibodies were isolated directly from antigen-positive B cells without fusion to myeloma cells, as described in US 2007/0280945A1.

Certain biological properties of the exemplary anti-IL-25 antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-IL-25 antibodies of the invention. The corresponding nucleic acid sequence identifiers are set forth in Table 2.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| H1M11009N | 2 | 4 | 6 | 8 | 10 | 12 | 14 | 16 |
| H2M10690N | 18 | 20 | 22 | 24 | 26 | 28 | 30 | 32 |
| H2M11008N | 34 | 36 | 38 | 40 | 42 | 44 | 46 | 48 |
| H4H10861P | 50 | 52 | 54 | 56 | 58 | 60 | 62 | 64 |
| H4H10862P | 66 | 68 | 70 | 72 | 74 | 76 | 78 | 80 |
| H4H10863P | 82 | 84 | 86 | 88 | 90 | 92 | 94 | 96 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H10864P | 98 | 100 | 102 | 104 | 106 | 108 | 110 | 112 |
| H4H10871P | 114 | 116 | 118 | 120 | 122 | 124 | 126 | 128 |
| H4H10876P | 130 | 132 | 134 | 136 | 138 | 140 | 142 | 144 |
| H4H10883P | 146 | 148 | 150 | 152 | 154 | 156 | 158 | 160 |
| H4H10897P | 162 | 164 | 166 | 168 | 170 | 172 | 174 | 176 |
| H4H10900P | 178 | 180 | 182 | 184 | 186 | 188 | 190 | 192 |
| H4H10901P | 194 | 196 | 198 | 200 | 202 | 204 | 206 | 208 |
| H4H10903P | 210 | 212 | 214 | 216 | 218 | 220 | 222 | 224 |
| H4H10905P | 226 | 228 | 230 | 232 | 234 | 236 | 238 | 240 |
| H4H10906P | 242 | 244 | 246 | 248 | 250 | 252 | 254 | 256 |
| H4H10907P | 258 | 260 | 262 | 264 | 266 | 268 | 270 | 272 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M11009N | 1 | 3 | 5 | 7 | 9 | 11 | 13 | 15 |
| H2M10690N | 17 | 19 | 21 | 23 | 25 | 27 | 29 | 31 |
| H2M11008N | 33 | 35 | 37 | 39 | 41 | 43 | 45 | 47 |
| H4H10861P | 49 | 51 | 53 | 55 | 57 | 59 | 61 | 63 |
| H4H10862P | 65 | 67 | 69 | 71 | 73 | 75 | 77 | 79 |
| H4H10863P | 81 | 83 | 85 | 87 | 89 | 91 | 93 | 95 |
| H4H10864P | 97 | 99 | 101 | 103 | 105 | 107 | 109 | 111 |
| H4H10871P | 113 | 115 | 117 | 119 | 121 | 123 | 125 | 127 |
| H4H10876P | 129 | 131 | 133 | 135 | 137 | 139 | 141 | 143 |
| H4H10883P | 145 | 147 | 149 | 151 | 153 | 155 | 157 | 159 |
| H4H10897P | 161 | 163 | 165 | 167 | 169 | 171 | 173 | 175 |
| H4H10900P | 177 | 179 | 181 | 183 | 185 | 187 | 189 | 191 |
| H4H10901P | 193 | 195 | 197 | 199 | 201 | 203 | 205 | 207 |
| H4H10903P | 209 | 211 | 213 | 215 | 217 | 219 | 221 | 223 |
| H4H10905P | 225 | 227 | 229 | 231 | 233 | 235 | 237 | 239 |
| H4H10906P | 241 | 243 | 245 | 247 | 249 | 251 | 253 | 255 |
| H4H10907P | 257 | 259 | 261 | 263 | 265 | 267 | 269 | 271 |

Antibodies are typically referred to herein according to the following nomenclature: Fc prefix (e.g. "H1M," "H2M," "H4H," etc.), followed by a numerical identifier (e.g. "11009," "10690," "10861," etc.), followed by a "P" or "N" suffix, as shown in Tables 1 and 2. Thus, according to this nomenclature, an antibody may be referred to herein as, e.g., "H1M11009N," "H2M10690N," "H4H10861P," etc. The H1M, H2M and H4H prefixes on the antibody designations used herein indicate the particular Fc region isotype of the antibody. For example, an "H1M" antibody has a mouse IgG1 Fc, an "H2M" antibody has a mouse IgG2 Fc, and an "H4H" antibody has a human IgG4 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Comparator Antibody Used in the Following Examples

A comparator anti-IL25 antibody was included in the following experiments for comparative purposes. In particular, "Comparator I" is an anti-IL-25 antibody with heavy and light chain variable domains having the amino acid sequences of the corresponding domains of "RH2.5_R71V," as set forth in U.S. Pat. No. 8,658,169.

Example 3. Surface Plasmon Resonance Derived Binding Affinities and Kinetic Constants of Human Monoclonal Anti-IL-25 Antibodies Equilibrium dissociation constants ($K_D$ values) for IL-25 binding to purified anti-IL-25 antibodies were determined using a real-time surface plasmon resonance biosensor assay on a Biacore 4000 instrument (GE Healthcare). The Biacore sensor surface was derivatized by amine coupling with either a polyclonal rabbit anti-mouse antibody (GE Healthcare, #BR-1008-38) or with a monoclonal mouse anti-human Fc antibody (GE Healthcare, #BR-1008-39) to capture anti-IL-25 antibodies expressed with different constant regions. All Biacore binding studies were performed in HBST running buffer (0.01M HEPES pH 7.4, 0.15M NaCl, 3 mM EDTA, 0.05% v/v Surfactant P20). All the IL-25 reagents were expressed with a C-terminal myc-myc-hexa-histidine tag (referred to herein as "IL-25-MMH"). Different concentrations of human IL-25-MMH (SEQ ID NO:273), monkey IL-25-MMH (SEQ ID NO:274), mouse IL-25-MMH (SEQ ID NO:275 and rat IL-25-MMH (SEQ ID NO:276), prepared in HBST running buffer (ranging from 100 nM to 3.7 nM, 3-fold dilutions), were injected over the anti-IL-25 antibody captured surface at a flow rate of 304/min. Association of all the IL-25-MMH reagents to each of the captured monoclonal antibodies was monitored for 4 minutes and their dissociation in HBST running buffer was monitored for 10 minutes. All the binding kinetics experiments were performed at either 25° C. or 37° C. as indicated in the Tables below. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as: $K_D$ (M)=$k_d$/$k_a$ and t1/2 (min)=(ln 2/(60*$k_d$). Binding kinetic parameters for human, monkey, mouse and rat IL-25-MMH binding to anti-IL-25 antibodies at 25° C. and 37° C. are shown in Tables 3 through 10. ("NB" denotes no binding observed under the experimental conditions tested; "IC" denotes inconclusive binding due to non-specific background binding to anti-mFc surface).

TABLE 3

Binding Kinetics Parameters of Anti-IL-25 Monoclonal Antibodies Binding to Human IL-25 at 25° C.

| Antibody | Amount of Antibody Captured (RU) | 100 nM Human IL-25-MMH Bound (RU) | $k_a$ (1/Ms) | $k_d$ (1/s) | $K_D$ (M) | t½ (min) |
|---|---|---|---|---|---|---|
| H4H10900P | 79 ± 0.44 | 43 | 1.74E+06 | 2.75E−05 | 1.58E−11 | 421 |
| H4H10864P | 136 ± 0.55 | 75 | 2.68E+06 | 4.51E−05 | 1.68E−11 | 256 |
| H4H10901P | 109 ± 0.61 | 62 | 2.28E+06 | 5.79E−05 | 2.54E−11 | 199 |
| H4H10861P | 83 ± 0.33 | 47 | 2.01E+06 | 2.34E−05 | 1.16E−11 | 493 |
| H4H10862P | 104 ± 0.61 | 56 | 1.88E+06 | 6.49E−05 | 3.44E−11 | 178 |
| H4H10883P | 99 ± 0.37 | 56 | 7.06E+05 | 1.00E−05 | 1.42E−11 | 1155 |
| H4H10903P | 96 ± 0.45 | 54 | 8.97E+05 | 1.73E−05 | 1.92E−11 | 670 |
| H4H10907P | 104 ± 0.26 | 40 | 7.36E+05 | 6.50E−05 | 8.83E−11 | 178 |
| H4H10871P | 94 ± 0.37 | 38 | 7.49E+05 | 6.38E−05 | 8.51E−11 | 181 |
| H4H10897P | 100 ± 2.61 | 39 | 6.23E+05 | 7.87E−05 | 1.26E−10 | 147 |
| H4H10876P | 127 ± 0.47 | 45 | 3.86E+05 | 4.78E−05 | 1.24E−10 | 242 |
| H4H10905P | 136 ± 0.48 | 49 | 4.78E+05 | 1.09E−04 | 2.28E−10 | 106 |
| H4H10863P | 96 ± 0.81 | 34 | 2.60E+05 | 7.25E−05 | 2.79E−10 | 159 |
| H2aM11008N | 111 ± 0.75 | 48 | 4.82E+05 | 2.10E−04 | 4.35E−10 | 55 |
| H4H10906P | 106 ± 0.30 | 61 | 1.64E+06 | 4.32E−05 | 2.64E−11 | 268 |
| H1M11009N | 96 ± 2.13 | 30 | 2.42E+05 | 3.04E−03 | 1.25E−08 | 4 |
| H2aM10690N | 159 ± 1.43 | 32 | 8.02E+04 | 2.90E−03 | 3.62E−08 | 4 |
| Comparator 1 | 241 ± 0.62 | 79 | 9.27E+05 | 1.12E−04 | 1.20E−10 | 103 |

TABLE 4

Binding Kinetics Parameters of Anti-IL-25 Monoclonal Antibodies Binding to Human IL-25 at 37° C.

| Antibody | Amount of Antibody Captured (RU) | 100 nM Human IL-25-MMH Bound (RU) | $k_a$ (1/Ms) | $k_d$ (1/s) | $K_D$ (M) | t½ (min) |
|---|---|---|---|---|---|---|
| H4H10900P | 92 ± 2.04 | 51 | 2.83E+06 | 9.91E−05 | 3.50E−11 | 117 |
| H4H10864P | 166 ± 2.68 | 94 | 3.73E+06 | 1.96E−04 | 5.26E−11 | 59 |
| H4H10901P | 121 ± 2.5 | 65 | 3.19E+06 | 2.08E−04 | 6.51E−11 | 56 |
| H4H10861P | 110 ± 2.49 | 63 | 2.91E+06 | 7.80E−05 | 2.68E−11 | 148 |
| H4H10862P | 134 ± 2.03 | 72 | 2.39E+06 | 2.10E−04 | 8.79E−11 | 55 |
| H4H10883P | 131 ± 3.8 | 74 | 1.58E+06 | 4.80E−05 | 3.04E−11 | 241 |
| H4H10903P | 111 ± 1.81 | 65 | 1.53E+06 | 7.75E−05 | 5.08E−11 | 149 |
| H4H10907P | 119 ± 1.72 | 47 | 1.19E+06 | 4.45E−05 | 3.75E−11 | 259 |
| H4H10871P | 126 ± 2.41 | 49 | 1.15E+06 | 3.18E−05 | 2.76E−11 | 363 |
| H4H10897P | 132 ± 2.4 | 48 | 1.04E+06 | 2.26E−04 | 2.18E−10 | 51 |
| H4H10876P | 170 ± 3.02 | 60 | 6.28E+05 | 5.93E−05 | 9.44E−11 | 195 |
| H4H10905P | 161 ± 2.46 | 55 | 8.09E+05 | 1.20E−04 | 1.49E−10 | 96 |
| H4H10863P | 130 ± 2.14 | 46 | 6.06E+05 | 7.78E−05 | 1.28E−10 | 149 |
| H2aM11008N | 130 ± 1.16 | 60 | 7.34E+05 | 7.93E−04 | 1.08E−09 | 15 |
| H4H10906P | 124 ± 2.05 | 72 | 2.90E+06 | 1.54E−04 | 5.29E−11 | 75 |
| H1M11009N | 103 ± 0.84 | 30 | 3.93E+05 | 8.29E−03 | 2.11E−08 | 1.4 |
| H2aM10690N | 196 ± 1.28 | 39 | 1.37E+05 | 8.44E−03 | 6.14E−08 | 1.4 |
| Comparator 1 | 301 ± 8.01 | 99 | 1.36E+06 | 1.82E−04 | 1.34E−10 | 64 |

TABLE 5

Binding Kinetics Parameters of Anti-IL-25 Monoclonal Antibodies Binding to Monkey IL-25 at 25° C.

| Antibody | Amount of Antibody Captured (RU) | 100 nM Monkey IL-25-MMH Bound (RU) | $k_a$ (1/Ms) | $k_d$ (1/s) | $K_D$ (M) | $t^{1/2}$ (min) |
|---|---|---|---|---|---|---|
| H4H10900P | 78 ± 0.23 | 45 | 2.94E+06 | 1.18E−05 | 4.02E−12 | 980 |
| H4H10864P | 135 ± 0.85 | 78 | 3.68E+06 | 4.70E−05 | 1.28E−11 | 246 |
| H4H10901P | 108 ± 0.21 | 64 | 2.63E+06 | 3.06E−05 | 1.16E−11 | 377 |
| H4H10861P | 83 ± 0.18 | 48 | 3.26E+06 | 1.48E−05 | 4.54E−12 | 779 |
| H4H10862P | 104 ± 0.69 | 58 | 2.00E+06 | 5.10E−05 | 2.55E−11 | 226 |
| H4H10883P | 99 ± 0.30 | 58 | 1.04E+06 | 1.00E−05 | 9.65E−12 | 1155 |
| H4H10903P | 96 ± 0.27 | 57 | 1.15E+06 | 1.00E−05 | 8.71E−12 | 1155 |
| H4H10907P | 104 ± 0.34 | 43 | 1.39E+06 | 6.74E−05 | 4.85E−11 | 171 |
| H4H10871P | 94 ± 0.28 | 42 | 6.28E+05 | 6.06E−05 | 9.65E−11 | 191 |
| H4H10897P | 101 ± 0.47 | 42 | 1.13E+06 | 8.43E−05 | 7.49E−11 | 137 |
| H4H10876P | 126 ± 0.38 | 51 | 3.29E+05 | 7.18E−05 | 2.18E−10 | 161 |
| H4H10905P | 136 ± 0.45 | 54 | 4.17E+05 | 7.77E−05 | 1.86E−10 | 149 |
| H4H10863P | 96 ± 0.36 | 39 | 3.43E+05 | 6.83E−05 | 1.99E−10 | 169 |
| H2aM11008N | 109 ± 1.04 | 64 | IC* | IC* | IC* | IC* |
| H4H10906P | 106 ± 0.42 | 61 | 2.09E+06 | 2.95E−05 | 1.41E−11 | 391 |
| H1M11009N | 93 ± 0.38 | 17 | IC* | IC* | IC* | IC* |
| H2aM10690N | 156 ± 0.64 | 46 | IC* | IC* | IC* | IC* |
| Comparator 1 | 267 ± 0.76 | 100 | 8.60E+05 | 7.52E−05 | 8.80E−11 | 154 |

*IC = denotes inconclusive binding due to non-specific background binding to anti-mFc surface

TABLE 6

Binding Kinetics Parameters of Anti-IL-25 Monoclonal Antibodies Binding to Monkey IL-25 at 37° C.

| Antibody | Amount of Antibody Captured (RU) | 100 nM Monkey IL-25-MMH Bound (RU) | $k_a$ (1/Ms) | $k_d$ (1/s) | $K_D$ (M) | $t^{1/2}$ (min) |
|---|---|---|---|---|---|---|
| H4H10900P | 86 ± 1.48 | 50 | 3.07E+06 | 7.49E−05 | 2.44E−11 | 154 |
| H4H10864P | 157 ± 2.66 | 94 | 4.35E+06 | 1.90E−04 | 4.36E−11 | 61 |
| H4H10901P | 114 ± 1.68 | 64 | 3.55E+06 | 1.65E−04 | 4.64E−11 | 70 |
| H4H10861P | 103 ± 1.86 | 61 | 3.03E+06 | 7.14E−05 | 2.36E−11 | 162 |
| H4H10862P | 127 ± 2.3 | 70 | 2.93E+06 | 1.72E−04 | 5.89E−11 | 67 |
| H4H10883P | 122 ± 2.21 | 72 | 1.75E+06 | 4.18E−05 | 2.39E−11 | 276 |
| H4H10903P | 105 ± 1.52 | 66 | 1.76E+06 | 6.59E−05 | 3.74E−11 | 175 |
| H4H10907P | 112 ± 1.68 | 50 | 1.51E+06 | 1.01E−04 | 6.71E−11 | 114 |
| H4H10871P | 118 ± 2.28 | 54 | 1.35E+06 | 7.40E−05 | 5.46E−11 | 156 |
| H4H10897P | 124 ± 1.98 | 49 | 1.22E+06 | 2.31E−04 | 1.89E−10 | 50 |
| H4H10876P | 162 ± 2.24 | 64 | 5.24E+05 | 5.45E−05 | 1.04E−10 | 212 |
| H4H10905P | 154 ± 1.5 | 59 | 6.68E+05 | 9.01E−05 | 1.35E−10 | 128 |
| H4H10863P | 122 ± 2.26 | 51 | 1.18E+06 | 8.07E−05 | 6.85E−11 | 143 |
| H2aM11008N | 127 ± 1 | 80 | IC* | IC* | IC* | IC* |
| H4H10906P | 118 ± 1.41 | 73 | 3.01E+06 | 1.30E−04 | 4.31E−11 | 89 |
| H1M11009N | 101 ± 0.94 | 23 | IC* | IC* | IC* | IC* |
| H2aM10690N | 193 ± 0.78 | 49 | IC* | IC* | I1C* | IC* |
| Comparator 1 | 335 ± 7.64 | 124 | 1.32E+06 | 6.24E−05 | 4.73E−11 | 185 |

*IC = denotes inconclusive binding due to non-specific background binding to anti-mFc surface

TABLE 7

Binding Kinetics Parameters of Anti-IL-25 Monoclonal Antibodies Binding to Mouse IL-25 at 25° C.

| Antibody | Amount of Antibody Captured (RU) | 100 nM Mouse IL-25-MMH Bound (RU) | $k_a$ (1/Ms) | $k_d$ (1/s) | $K_D$ (M) | $t^{1/2}$ (min) |
|---|---|---|---|---|---|---|
| H4H10900P | 78 ± 0.48 | 0 | NB* | NB* | NB* | NB* |
| H4H10864P | 135 ± 0.14 | −1 | NB* | NB* | NB* | NB* |
| H4H10901P | 108 ± 0.33 | 1 | NB* | NB* | NB* | NB* |
| H4H10861P | 82 ± 0.08 | 0 | NB* | NB* | NB* | NB* |
| H4H10862P | 104 ± 0.08 | 0 | NB* | NB* | NB* | NB* |
| H4H10883P | 99 ± 0.17 | 0 | NB* | NB* | NB* | NB* |
| H4H10903P | 95 ± 0.16 | 0 | NB* | NB* | NB* | NB* |
| H4H10907P | 104 ± 0.15 | 10 | 1.96E+05 | 1.15E−02 | 5.87E−08 | 1.0 |
| H4H10871P | 94 ± 0.04 | 30 | 1.21E+05 | 1.11E−04 | 9.18E−10 | 104 |
| H4H10897P | 101 ± 0.06 | 20 | 1.48E+05 | 1.04E−03 | 7.05E−09 | 11 |

TABLE 7-continued

Binding Kinetics Parameters of Anti-IL-25 Monoclonal Antibodies Binding to Mouse IL-25 at 25° C.

| Antibody | Amount of Antibody Captured (RU) | 100 nM Mouse IL-25-MMH Bound (RU) | $k_a$ (1/Ms) | $k_d$ (1/s) | $K_D$ (M) | $t\frac{1}{2}$ (min) |
|---|---|---|---|---|---|---|
| H4H10876P | 125 ± 0.10 | 40 | 1.74E+05 | 9.89E−05 | 5.70E−10 | 117 |
| H4H10905P | 135 ± 0.23 | 43 | 1.24E+05 | 1.45E−04 | 1.17E−09 | 80 |
| H4H10863P | 95 ± 0.10 | 22 | 5.57E+04 | 1.49E−04 | 2.67E−09 | 78 |
| H2aM11008N | 108 ± 0.33 | −1 | NB* | NB* | NB* | NB* |
| H4H10906P | 106 ± 0.50 | 1 | NB* | NB* | NB* | NB* |
| H1M11009N | 92 ± 0.25 | 0 | NB* | NB* | NB* | NB* |
| H2aM10690N | 156 ± 0.23 | 17 | 3.88E+04 | 3.19E−03 | 8.23E−08 | 4 |
| Comparator 1 | 271 ± 0.69 | 88 | 5.71E+05 | 1.17E−04 | 2.05E−10 | 99 |

*NB = denotes no binding observed under the experimental conditions tested

TABLE 8

Binding Kinetics Parameters of Anti-IL-25 Monoclonal Antibodies Binding to Mouse IL-25 at 37° C.

| Antibody | Amount of Antibody Captured (RU) | 100 nM Mouse IL-25-MMH Bound (RU) | $k_a$ (1/Ms) | $k_d$ (1/s) | $K_D$ (M) | $t\frac{1}{2}$ (min) |
|---|---|---|---|---|---|---|
| H4H10900P | 84 ± 0.49 | 2 | NB* | NB* | NB* | NB* |
| H4H10864P | 154 ± 0.42 | 1 | NB* | NB* | NB* | NB* |
| H4H10901P | 111 ± 0.4 | 2 | NB* | NB* | NB* | NB* |
| H4H10861P | 99 ± 0.69 | 2 | NB* | NB* | NB* | NB* |
| H4H10862P | 123 ± 0.13 | 2 | NB* | NB* | NB* | NB* |
| H4H10883P | 117 ± 0.47 | 1 | NB* | NB* | NB* | NB* |
| H4H10903P | 102 ± 0.47 | 1 | NB* | NB* | NB* | NB* |
| H4H10907P | 109 ± 0.02 | 8 | 2.75E+05 | 3.76E−02 | 1.37E−07 | 0.3 |
| H4H10871P | 114 ± 0.88 | 41 | 3.22E+05 | 8.29E−05 | 2.58E−10 | 139 |
| H4H10897P | 121 ± 0.47 | 17 | 1.77E+05 | 6.41E−03 | 3.62E−08 | 1.8 |
| H4H10876P | 157 ± 0.58 | 51 | 3.69E+05 | 8.97E−05 | 2.43E−10 | 129 |
| H4H10905P | 151 ± 0.14 | 47 | 4.03E+05 | 1.78E−04 | 4.41E−10 | 65 |
| H4H10863P | 118 ± 1.04 | 37 | 1.34E+05 | 1.53E−04 | 1.14E−09 | 76 |
| H2aM11008N | 126 ± 0.89 | 2 | NB* | NB* | NB* | NB* |
| H4H10906P | 114 ± 1.18 | 2 | NB* | NB* | NB* | NB* |
| H1M11009N | 100 ± 0.2 | 2 | NB* | NB* | NB* | NB* |
| H2aM10690N | 192 ± 0.85 | 27 | 9.53E+04 | 7.78E−03 | 8.17E−08 | 1.5 |
| Comparator 1 | 332 ± 8.16 | 111 | 1.01E+06 | 8.16E−05 | 8.08E−11 | 142 |

*NB = denotes no binding observed under the experimental conditions tested

TABLE 9

Binding Kinetics Parameters of Anti-IL-25 Monoclonal Antibodies Binding to Rat IL-25 at 25° C.

| Antibody | Amount of Antibody Captured (RU) | 100 nM Rat IL-25-MMH Bound (RU) | $k_a$ (1/Ms) | $k_d$ (1/s) | $K_D$ (M) | $t\frac{1}{2}$ (min) |
|---|---|---|---|---|---|---|
| H4H10900P | 78 ± 0.06 | 0 | NB* | NB* | NB* | NB* |
| H4H10864P | 135 ± 0.50 | −1 | NB* | NB* | NB* | NB* |
| H4H10901P | 108 ± 0.15 | 0 | NB* | NB* | NB* | NB* |
| H4H10861P | 82 ± 0.34 | 0 | NB* | NB* | NB* | NB* |
| H4H10862P | 103 ± 0.46 | 1 | NB* | NB* | NB* | NB* |
| H4H10883P | 99 ± 0.30 | 0 | NB* | NB* | NB* | NB* |
| H4H10903P | 95 ± 0.43 | 1 | NB* | NB* | NB* | NB* |
| H4H10907P | 103 ± 0.4 | 10 | 2.20E+05 | 1.47E−02 | 6.69E−08 | 0.8 |
| H4H10871P | 94 ± 0.18 | 37 | 5.48E+05 | 7.23E−05 | 1.32E−10 | 160 |
| H4H10897P | 100 ± 0.24 | 23 | 3.33E+05 | 8.07E−04 | 2.42E−09 | 14 |
| H4H10876P | 125 ± 0.32 | 45 | 2.59E+05 | 8.81E−05 | 3.41E−10 | 131 |
| H4H10905P | 135 ± 0.24 | 45 | 1.67E+05 | 1.35E−04 | 8.10E−10 | 85 |
| H4H10863P | 95 ± 0.40 | 34 | 1.53E+05 | 1.64E−04 | 1.07E−09 | 70 |
| H2aM11008N | 107 ± 0.23 | 0 | NB* | NB* | NB* | NB* |
| H4H10906P | 106 ± 0.38 | 2 | NB* | NB* | NB* | NB* |
| H1M11009N | 92 ± 0.26 | −1 | NB* | NB* | NB* | NB* |
| H2aM10690N | 155 ± 0.26 | 18 | 9.18E+04 | 9.50E−03 | 1.03E−07 | 1.2 |
| Comparator 1 | 266 ± 0.53 | 91 | 9.27E+05 | 9.55E−05 | 1.03E−10 | 121 |

*NB = denotes no binding observed under the experimental conditions tested

TABLE 10

Binding Kinetics Parameters of Anti-IL-25 Monoclonal Antibodies Binding to Rat IL-25 at 37° C.

| Antibody | Amount of Antibody Captured (RU) | 100 nM Rat IL-25-MMH Bound (RU) | $k_a$ (1/Ms) | $k_d$ (1/s) | $K_D$ (M) | $t^{1/2}$ (min) |
|---|---|---|---|---|---|---|
| H4H10900P | 82 ± 0.55 | 2 | NB* | NB* | NB* | NB* |
| H4H10864P | 153 ± 0.52 | 1 | NB* | NB* | NB* | NB* |
| H4H10901P | 110 ± 0.53 | 1 | NB* | NB* | NB* | NB* |
| H4H10861P | 97 ± 0.71 | 2 | NB* | NB* | NB* | NB* |
| H4H10862P | 121 ± 1.02 | 1 | NB* | NB* | NB* | NB* |
| H4H10883P | 116 ± 0.77 | 0 | NB* | NB* | NB* | NB* |
| H4H10903P | 100 ± 0.77 | 2 | NB* | NB* | NB* | NB* |
| H4H10907P | 107 ± 0.78 | 8 | 2.38E+05 | 2.04E−02 | 8.54E−08 | 0.6 |
| H4H10871P | 112 ± 0.54 | 45 | 9.37E+05 | 5.64E−05 | 6.02E−11 | 205 |
| H4H10897P | 118 ± 0.75 | 22 | 2.45E+05 | 6.01E−03 | 2.46E−08 | 1.9 |
| H4H10876P | 156 ± 1.22 | 53 | 4.50E+05 | 1.07E−04 | 2.38E−10 | 108 |
| H4H10905P | 148 ± 1.25 | 49 | 4.81E+05 | 1.81E−04 | 3.77E−10 | 64 |
| H4H10863P | 116 ± 0.75 | 41 | 4.74E+05 | 3.41E−04 | 7.20E−10 | 34 |
| H2aM11008N | 125 ± 0.2 | 3 | NB* | NB* | NB* | NB* |
| H4H10906P | 113 ± 0.73 | 3 | NB* | NB* | NB* | NB* |
| H1M11009N | 99 ± 0.5 | 3 | NB* | NB* | NB* | NB* |
| H2aM10690N | 191 ± 0.58 | 20 | 1.68E+05 | 1.93E−02 | 1.15E−07 | 0.6 |
| Comparator 1 | 325 ± 8.52 | 109 | 1.59E+06 | 1.02E−04 | 6.42E−11 | 113 |

*NB = denotes no binding observed under the experimental conditions tested

At 25° C., the anti-IL-25 antibodies of the invention bound to human IL-25 with $K_D$ values ranging from 11.6 pM to 36.2 nM, while Comparator 1 bound human IL-25 with a $K_D$ value of 120 pM (Table 3). At 37° C., the anti-IL-25 antibodies of the invention bound to human IL-25 with $K_D$ values ranging from 26.8 pM to 61.4 nM, while Comparator 1 bound human IL-25 with a $K_D$ value of 134 pM (Table 4). At 25° C., 14 out of the 17 anti-IL-25 antibodies of the invention bound to monkey IL-25 with $K_D$ values ranging from 4.02 pM to 218 pM, while Comparator 1 bound monkey IL-25 with a $K_D$ value of 88.0 pM (Table 5). At 37° C., 14 out of the 17 anti-IL-25 antibodies of the invention bound to monkey IL-25 with $K_D$ values ranging from 23.6 pM to 189 pM, while Comparator 1 bound monkey IL-25 with a $K_D$ value of 47.3 pM (Table 6). Three antibodies of the invention did not demonstrate conclusive binding to monkey IL-25 at either 25° C. or 37° C. At 25° C., 7 out of the 17 anti-IL-25 antibodies of the invention bound to mouse IL-25 with $K_D$ values ranging from 570 pM to 82.3 nM, while Comparator 1 bound mouse IL-25-MMH with a $K_D$ value of 205 pM (Table 7). At 37° C., 7 out of the 17 anti-IL-25 antibodies of the invention bound to mouse IL-25 with $K_D$ values ranging from 243 pM to 137 nM, while Comparator 1 bound mouse IL-25-MMH with a $K_D$ value of 80.8 pM (Table 8). Ten antibodies of the invention did not demonstrate binding to mouse IL-25 at either 25° C. or 37° C. At 25° C., 7 out of the 17 anti-IL-25 antibodies of the invention bound to rat IL-25 with $K_D$ values ranging from 132 pM to 103 nM, while Comparator 1 bound rat IL-25 with a $K_D$ value of 103 pM (Table 9). At 37° C., 7 out of the 17 anti-IL-25 antibodies of the invention bound to rat IL-25 with $K_D$ values ranging from 60.2 pM to 115 nM, while Comparator 1 bound rat IL-25 with a $K_D$ value of 64.2 pM (Table 10). Ten antibodies of the invention did not demonstrate binding to rat IL-25 at either 25° C. or 37° C.

Example 4. Anti-IL-25 Antibody Cross-Competition

Binding competition between anti-IL-25 monoclonal antibodies was determined using a real time, label-free bio-layer interferometry assay on an Octet QK384 biosensor (Pall ForteBio Corp.).

The entire experiment was performed at 25° C. in HBST kinetics buffer (0.01 M HEPES pH7.4, 0.15M NaCl, 3 mM EDTA, 0.05% v/v Surfactant P20, 0.1 mg/ml BSA) with the plate shaking at the speed of 1000 rpm. To assess whether 2 antibodies were able to compete with one another for binding to their respective epitopes on the recombinant human IL-25 expressed with a C-terminal myc-myc-hexa-histidine tag (hIL-25-MMH; SEQ ID NO:273), about −0.5 to 0.7 nm of hIL-25-MMH was first captured onto anti-Penta-His antibody coated Octet biosensors (Fortebio Inc, #18-5079) by submerging the biosensors for 5 minutes into wells containing a 4 μg/mL solution of hIL-25-MMH. The antigen-captured biosensors were then saturated with the first anti-IL-25 monoclonal antibody (referred to herein as mAb-1) by dipping into wells containing 50 μg/mL solution of mAb-1 for 5 minutes. The biosensors were then subsequently dipped into wells containing a 50 μg/mL solution of a second anti-IL-25 monoclonal antibody (referred to herein as mAb-2). The biosensors were washed in HBST kinetics buffer in between every step of the experiment. The real-time binding response was monitored during the course of the experiment and the binding response at the end of every step was recorded. The response of mAb-2 binding to hIL-25-MMH pre-complexed with mAb-1 was compared and competitive/non-competitive behavior of different anti-IL-25 monoclonal antibodies was determined. In several instances, anti-IL-25 antibodies were unable to completely saturate the captured hIL-25-MMH surface, causing a certain amount of binding signal to be observed during self-competition. Therefore, the cross-competition matrix was generated by subtracting the self-competition signal from the specific mAb-2 binding and any binding signal less than 0 nm was recorded as 0 nm. Results are summarized in FIG. 1. The key to the mAb identifiers and the antibodies to which they correspond and the binding responses that were observed for hIL-25-MMH binding to the anti-Penta-His sensor and for mAb-1 binding to the captured hIL-25-mmh are shown in Table 11.

TABLE 11

Antibody Identifiers Corresponding to the Antibodies Tested in the Cross-Competition Assay Depicted in FIG. 1

| mAb Identifier shown in FIG. 1 | Corresponding Antibody | hIL-25-MMH Captured (nm) | 50 ug/mL mAb-1 Binding (nm) |
|---|---|---|---|
| 1 | H4H10883P | 0.58 ± 0.02 | 0.7 ± 0.04 |
| 2 | H4H10900P | 0.55 ± 0.03 | 0.68 ± 0.04 |
| 3 | H4H10901P | 0.53 ± 0.03 | 0.67 ± 0.04 |
| 4 | H4H10903P | 0.8 ± 0.03 | 1.03 ± 0.03 |
| 5 | H4H10861P | 0.67 ± 0.02 | 0.88 ± 0.03 |
| 6 | H4H10862P | 0.66 ± 0.02 | 0.83 ± 0.03 |
| 7 | H2aM11008N | 0.71 ± 0.02 | 0.81 ± 0.03 |
| 8 | H4H10864P | 0.67 ± 0.02 | 0.84 ± 0.04 |
| 9 | H4H10906P | 0.71 ± 0.03 | 0.88 ± 0.03 |
| 10 | H4H10897P | 0.57 ± 0.02 | 1.12 ± 0.06 |
| 11 | H4H10907P | 0.73 ± 0.03 | 1.74 ± 0.06 |
| 12 | H1M11009N | 0.69 ± 0.02 | 1.42 ± 0.05 |
| 13 | H2aM10690N | 0.79 ± 0.02 | 1.38 ± 0.04 |
| 14 | H4H10863P | 0.71 ± 0.03 | 1.13 ± 0.04 |
| 15 | H4H10871P | 0.65 ± 0.02 | 1.12 ± 0.04 |
| 16 | H4H10876P | 0.62 ± 0.02 | 1.07 ± 0.05 |
| 17 | H4H10905P | 0.77 ± 0.03 | 1.59 ± 0.05 |
| 18 | Comparator 1 | 0.69 ± 0.02 | 1.49 ± 0.07 |

In FIG. 1, light grey boxes with black font represent self-competition. Antibodies competing in both directions, independent of the order of binding are represented with black boxes and white font. No competition between antibodies suggestive of distinct binding epitopes is represented as white boxes with black font. Dark grey boxes with white font represent binding responses of isotype control antibodies and buffer alone.

This example shows that several of the antibodies of the invention cross-compete with one or more other antibodies of the invention for binding to IL-25; while certain antibodies of the invention (e.g., H1M11009N [12]) show little or no cross-competition with other antibodies tested).

Example 5. Anti-IL-25 Antibodies Block IL-25 Binding to IL-17RB

The ability of anti-IL-25 antibodies to block human IL-25 binding to one of its natural receptors, human IL-17RB, was measured in a competition sandwich ELISA.

The extracellular domain of human IL-17RB protein, expressed with a C-terminal human Fc tag (hIL17RB-hFc; R&D Systems, #1207-BR), was coated at 2 µg/mL on a 96-well microtiter plate in a PBS buffer overnight at 4° C. Nonspecific binding sites were subsequently blocked using a 0.5% (w/v) solution of BSA in PBS. A constant concentration of 2 nM of human IL-25 expressed with a C-terminal myc-myc-hexahistidine tag (hIL-25-MMH; SEQ ID NO:273) was added to serial dilutions of antibodies so that the final concentrations of antibodies ranged from 0 to 200 nM. The antibody/hIL-25-MMH mixtures were incubated for 1 hour at room temperature (RT) before they were transferred to microtiter plates coated with hIL-17RB-hFc. After incubating for 1 hour at RT, the wells were then washed, and plate-bound hIL-25-MMH was detected with a horse-radish peroxidase conjugated anti-myc polyclonal antibody (Novus Biologicals, #NB600-341). Samples were developed with a TMB solution to produce a colorimetric reaction and then quenched with 1M sulfuric acid before measuring absorbance at 450 nm on a Victor X5 plate reader. Data analysis was performed using a sigmoidal dose-response model within Prism™ software (Graph Pad). The calculated $IC_{50}$ value, defined as the concentration of antibody required to block 50% of hIL-25-MMH binding to hIL-17RB-hFc, was used as an indicator of a blocking potency. The absorbance measured for the constant concentration of hIL-25-MMH alone is defined as 0% blocking and the absorbance measured for no added hIL-25-MMH is defined as 100% blocking. Percent blockade was calculated as the ratio of the reduction in signal observed in the presence of antibody relative to the difference between the signal with hIL-25-MMH alone and background (signal from HRP-conjugated secondary antibody alone) subtracted from 100% blocking as defined previously. The absorbance values of the wells containing the highest concentration for each antibody were used to determine the percent maximum blockade. $IC_{50}$ values and maximum percent blockade for each antibody tested are shown in Table 12.

TABLE 12

Antibody Blockade of IL-25 Binding to IL-17RB

| Antibody | Blocking 2 nM hIL-25-MMH binding to hIL-17RB-hFc, $IC_{50}$, (M) | % Maximum blocking of 200 nM antibody blocking 2 nM of hIL-25-MMH binding to hIL-17RB-hFc |
|---|---|---|
| H4H10900P | 2.0E−10(*) | 90 |
| H4H10864P | 2.6E−10(*) | 88 |
| H4H10901P | 2.3E−10(*) | 91 |
| H4H10861P | 2.0E−10(*) | 92 |
| H4H10862P | 2.4E−10(*) | 89 |
| H4H10883P | 2.0E−10(*) | 93 |
| H4H10903P | 2.4E−10(*) | 91 |
| H4H10907P | 5.5E−10(*) | 87 |
| H4H10871P | 7.1E−10(*) | 92 |
| H4H10897P | 3.2E−10(*) | 94 |
| H4H10876P | 6.5E−10(*) | 89 |
| H4H10905P | 5.3E−10(*) | 86 |
| H4H10863P | 9.2E−10(*) | 87 |
| H2aM11008N | 4.3E−10(*) | 98 |
| H1M11009N | Non-blocker | 20 |
| H4H10906P | 1.4E−10(*) | 89 |
| H2aM10690N | 3.1E−08 | 70 |
| Comparator 1 | 2.5E−10(*) | 90 |
| hIgG4 isotype control | Non-blocker | −31 |
| mIgG2a isotype control | Non-blocker | −45 |

(*)Below theoretical bottom of the assay calculated as 1.0 nM for this assay, where dimeric hIL-25MMH in solution was fixed at a concentration of 2 nM.

Antibodies that had no effect on the signal of the hIL-25-MMH constant or showed a decrease in binding signal of 25% or less were defined as non-blockers. The theoretical assay bottom is 0.5 nM indicating that lower calculated $IC_{50}$ values may not represent quantitative protein-antibody site binding. For this reason, antibodies with calculated $IC_{50}$ values lower than 0.5 nM are reported as <5.0E−10 M in Table 12.

As shown in Table 12, sixteen of the 17 anti-IL-25 antibodies tested blocked 2 nM of hIL-25-MMH from binding to hIL-17RB-hFc with $IC_{50}$ values ranging from less than 0.5 nM to 31 nM and percent maximum blockade ranging from 70% to 98%. Comparator 1 blocked 90% of the binding of 2 nM hIL-25-MMH from binding to hIL-17RB-hFc with an $IC_{50}$ value of less than 0.5 nM. One antibody, H1M11009N, was identified as a non-blocker under these assay conditions.

Example 6. Anti-IL-25 Antibodies Block IL-25-Mediated Signaling in Cell Lines Engineered to Express IL-17RA and IL-17RB A bioassay was developed to detect IL-25-mediated cell signaling and to measure the extent to which anti-IL-25 antibodies of the invention block IL-25 signaling in vitro.

For this assay HEK293 cell lines were generated to stably express human IL-17RA (amino acids 1 through 866 of accession number NP_055154.3), IL-17RB (amino acids 1 through 502 of accession number NP_061195.2), and Act1 (amino acids 1 through 564 of accession number NP_001157753.1), along with a luciferase reporter [NFκB response element (5×)-luciferase-IRES-GFP]. The resulting stable cell line, referred to as HEK293/NFκB-luc/hIL17RA/hIL17RB/hAct1, was isolated and maintained in 10% DMEM containing 10% FBS, NEAA, pencillin/streptomycin, 500 μg/mL G418, 100 μg/mL hygromycin B, and 1 μg/mL puromycin.

Cells were seeded into 96-well assay plates at 10,000 cells/well in OPTIMEM supplemented with 0.1% FBS and then incubated at 37° C. in 5% $CO_2$ overnight. The next day, to determine the dose response of IL-25, either human IL-25 expressed with a C-terminal myc-myc hexahistidine tag (hIL-25-MMH; SEQ ID NO:273), cynomolgus monkey IL-25 expressed with a C-terminal myc-myc hexahistidine tag (MfIL-25-MMH; SEQ ID NO:274) or mouse IL-25 expressed with a C-terminal myc-myc hexahistidine tag (mIL-25-MMH; SEQ ID NO:275 were serially diluted at 1:3 (from 3 nM to 0.0001 nM) and added to cells. A control containing dilution buffer but no IL-25 was also added to one sample of cells. To measure inhibition, antibodies were serially diluted and added to the cells followed by addition of constant concentrations of IL-25 (5 pM for both hIL-25-MMH, 12 pM for MfIL-25-MMH and 10 pM for mIL-25-MMH). The dilution series of the antibodies before adding to cells was at 1:3 starting at 100 nM and ranging down to 0.002 nM plus a control sample containing buffer alone without antibody. Luciferase activity was measured after 5.5 hours of incubation at 37° C. in 5% $CO_2$ followed by the addition of ONE-GLO® reagent (Promega, #E6051) using a Victor X (Perkin Elmer) plate reader. The results were analyzed using nonlinear regression (4-parameter logistics) with Prism 5 software (Graph Pad) to obtain $EC_{50}$ and $IC_{50}$ values. Results are shown in Table 13.

TABLE 13

Inhibition of IL-25-Mediated Signaling

| | IL25 Species | | |
|---|---|---|---|
| | Human | Monkey | Mouse |
| | $EC_{50}$ [M] | | |
| | 2.9E−12 | 1.6E−11 | 1.9E−11 8.4E−12 |
| | Constant IL25 used in assay | | |
| | 5 pM | 12 pM | 10 pM |
| Antibodies | $IC_{50}$ [M] | $IC_{50}$ [M] | $IC_{50}$ [M] $IC_{50}$ [M] |
| H2aM10690N | Blocks at high concentration | | |
| H4H10861P | 6.3E−11 | 3.7E−11 | |
| H4H10862P | 8.4E−11 | 3.3E−11 | |
| H4H10863P | 6.9E−10 | 3.5E−10 | 4.3E−09 |
| H4H10864P | 3.6E−11 | 2.6E−11 | |
| H4H10871P | 3.2E−10 | 8.8E−11 | 6.7E−10 |
| H4H10876P | 4.6E−10 | 2.1E−10 | 8.8E−10 |
| H4H10883P | 1.4E−10 | 3.9E−11 | |
| H4H10897P | 4.6E−10 | 4.0E−10 | 1.5E−08 |
| H4H10900P | 3.1E−11 | 2.2E−11 | |
| H4H10901P | 5.6E−11 | 3.8E−11 | |
| H4H10903P | 1.4E−10 | 6.0E−11 | |
| H4H10905P | 5.1E−10 | 2.1E−10 | 6.8E−10 |
| H4H10906P | | 2.7E−11 | 4.7E−11 |
| H4H10907P | 2.2E−10 | 1.4E−10 | NB |
| H2aM11008N | 1.8E−09 | | |

TABLE 13-continued

Inhibition of IL-25-Mediated Signaling

| | IL25 Species | | |
|---|---|---|---|
| | Human | Monkey | Mouse |
| | $EC_{50}$ [M] | | |
| | 2.9E−12 | 1.6E−11 | 1.9E−11 8.4E−12 |
| | Constant IL25 used in assay | | |
| | 5 pM | | 12 pM 10 pM |
| Antibodies | $IC_{50}$ [M] | $IC_{50}$ [M] | $IC_{50}$ [M] $IC_{50}$ [M] |
| H1M11009N | Blocks at high concentration | | |
| Comparator 1 | 7.2E−10 | 2.2E−10 | 3.8E−10 6.1E−10 |
| Isotype control 1 | NB | | |
| Isotype control 2 | NB | NB | NB NB |

NB = non-blocker

As shown in Table 13, hIL-25-MMH activated with $EC_{50}$ values of 2.9 pM and 16 pM in two separate assay days; mfIL-25-MMH activated with an $EC_{50}$ value of 19 pM; and mIL-25-MMH activated with an $EC_{50}$ value of 8.4 pM.

With regard to blocking, 15 of the 17 antibodies of the invention completely blocked the stimulation of the HEK293/NFκB-luc/hIL17RA/hIL17RB/hAct1 cells by 5 pM hIL-25-MMH with $IC_{50}$ values ranging from 27 pM to 1.8 nM, while Comparator 1 completely blocked with $IC_{50}$ values of 720 pM and 220 pM in two separate assay days. Two antibodies tested, H2aM10690N and H1M11009N, partially inhibited 5 pM hIL-25-MMH at high antibody concentrations. All 14 antibodies of the invention tested completely blocked the stimulation of the HEK293/NFκB-luc/hIL17RA/hIL17RB/hAct1 cells by 12 pM MfIL-25-MMH with $IC_{50}$ values ranging from 22 pM to 400 pM, while Comparator 1 completely blocked with an $IC_{50}$ value of 380 pM. Five of 6 antibodies of the invention tested completely blocked the stimulation of the HEK293/NFκB-luc/hIL17RA/hIL17RB/hAct1 cells by 10 pM mIL-25-MMH with $IC_{50}$ values ranging from 670 pM to 15 nM, while Comparator 1 completely blocked with an $IC_{50}$ value of 610 pM. Isotype control antibodies were also tested and displayed no inhibition in any of the assays.

Example 7. Anti-IL-25 Antibodies Block IL-25-Mediated Signaling in a Primary Cell-Based Assay The blocking ability of anti-IL-25 antibodies of the invention was further assessed using a primary cell based assay using peripheral blood mononuclear cells (PBMCs) (see Rickel et al., *The Journal of Immunology*, 2008, vol. 181 (6) pp. 4299-4310).

PBMCs were purified from fresh whole blood from two different donors by density gradient centrifugation. Briefly, K2 EDTA whole blood was diluted two-fold in RPMI 1640, carefully layered over Ficoll-Paque (GE Healthcare, #17-1440-03) and centrifuged for 20 minutes. The interphase layer containing the PBMCs was aspirated, transferred to a new tube and washed twice with PBS. The isolated PBMCs were plated in 75 $cm^2$ flasks at a final concentration of $2×10^6$ cells/mL in RPMI 1640 supplemented with 10% FBS, 2 mM L-glutamine, 100 U/mL penicillin and 100 ng/mL of recombinant thymic stromal lymphoprotein (TSLP; R&D Systems, #1398-TS/CF). After 24 hours, cells were harvested, washed in RPMI 1640, and plated in round-bottom 96-wells plates at a final concentration of $3\times10^5$ cells/mL in RPMI 1640 supplemented with 10% FBS, 2 mM L-glutamine, 100 U/mL penicillin, and 100 µg/mL streptomycin. Cells were then incubated with 50 ng/mL of TSLP, 10 ng/mL of human IL-2 (IL-2; R&D Systems, #202-IL/CF), 1 nM of human IL-25 expressed with a C-terminal myc-myc-hexahistidine tag (hIL-25-MMH; SEQ ID:273) and serial dilutions of antibodies from 200 nM to 48.8 pM at a final volume was 200 µL per well. Each sample was tested in triplicate. When antibodies were present, they were added to the cells after 30 minutes of pre-incubation with IL-25.

The cells were then incubated for 72 hours at 37° C. in a humidified incubator with 5% $CO_2$. IL-5 levels in the culture supernatant were subsequently measured using a commercially available ELISA (R&D Systems, #DY205). For the ELISA, 96-well flat-bottom plates were coated with the capture antibody, according to the manufacturer's instructions. After washing and blocking, 100 µL of undiluted culture supernatant was added to the plates and incubated for 2 hour. Subsequent washes and detection were done following the manufacturer's instructions. Results are summarized in Tables 14 and 15.

TABLE 14 hIL-25-MMH induction of IL-5 release from human PBMC.

| [hIL-25-MMH] (M) | IL-5 released from Donor 727058-059 (ng/mL) | | IL-5 released from Donor 727060 (ng/mL) | |
|---|---|---|---|---|
| | Mean | Standard deviation | Mean | Standard deviation |
| 1E−09 | 0.071 | 0.021 | 0.599 | 0.088 |
| 0 | 0.014 | 0.007 | 0.083 | 0.022 |

TABLE 15

Blockade of hIL-25-MMH induced IL-5 release from human PBMC by anti-IL-25 antibodies

| Antibody | $IC_{50}$ values of antibodies for blocking IL-5 release from Donor #727058-059 (M) | $IC_{50}$ values of antibodies for blocking IL-5 release from Donor #727060 (M) |
|---|---|---|
| H4H10900P | 3.921E−11 | 5.781e−010 |
| H4H10864P | 1.149E−09 | 6.771e−010 |
| H4H10871P | 1.178E−10 | 6.363e−010 |
| H4H10876P | 1.720E−10 | 1.296e−010 |
| Comparator 1 | 5.685E−09 | 1.590e−008 |

As shown in Table 14, human IL-25-MMH at 1 nM, in the presence of TSLP and IL-2, induced the release of 0.071 ng/mL of IL-5 from human total PBMC obtained from donor #727058-059 and 0.599 ng/mL of IL-5 from human total PBMC obtained from donor #727060.

As shown in Table 15, all 4 anti-IL-25 antibodies of the invention tested blocked the release of IL-5 from human PBMC induced by 1 nM of hIL-25-MMH, with $IC_{50}$ values ranging from 39.2 pM to 1.149 nM for donor #727058-059, and with $IC_{50}$ values ranging from 129.6 pM to 677.1 pM for donor #727060. Comparator 1 blocked release of IL-5 with an $IC_{50}$ value of 5.685 nM for donor #727058-059 and an $IC_{50}$ value of 15.9 nM for donor #727060.

This Example confirms that anti-IL-25 antibodies of the invention are able to potently block IL-25 signaling in cells to a greater extent than a comparator anti-IL-25 antibody.

Example 8. IL-25 Hydrodynamic Delivery of DNA (HDD)-Induced Lung Eosinophilia, Goblet Cells Metaplasia and Elevated Serum IgE to Study In Vivo Efficacy of Candidate mAbs Human IL-25 was overexpressed in wild type (WT) mice by hydrodynamic delivery of DNA (HDD). For the HDD experiment, WT mice were injected with either 25 pg of a plasmid expressing full length human IL-25 (See NM_022789.3; hIL-25 and also SEQ ID NO: 277 (DNA) and SEQ ID NO: 278 (Protein)) or with 25 pg of the same plasmid devoid of coding sequence (empty vector). A subset of the mice injected with hIL-25 plasmid were injected subcutaneously with either an IL-25 antibody, or a matching dose of an isotype control antibody three days prior to the HDD injection, on the day of the HDD injection and then on day 2 and 4 post-HDD injection. Mice were sacrificed 7 days after the HDD injection, and blood and lungs were collected. Serum IgE levels were quantified by ELISA; lung eosinophilia was assessed by isolation of cells infiltrating the lungs after collagenase treatment and flow cytometry; and goblet cells metaplasia was assessed by quantification of periodic acid Schiff (PAS) stained lung sections.

Experimental dosing and treatment protocol for groups of mice are shown in Tables 16A and 16B.

TABLE 16A

Study 1

| Group | Mice | n | Construct | Antibody | mAb dose |
|---|---|---|---|---|---|
| 1 | WT | 3 | Empty vector | None | |
| 2 | WT | 5 | hIL-25 | Isotype control | 25 mg/kg |
| 3 | WT | 5 | hIL-25 | Anti-IL-25 H4H10871P | 25 mg/kg |
| 4 | WT | 5 | hIL-25 | Anti-IL-25 H4H10900P | 25 mg/kg |

TABLE 16B

Study 2

| Group | Mice | n | Construct | Antibody | mAb dose |
|---|---|---|---|---|---|
| 1 | WT | 5 | Empty vector | None | |
| 2 | WT | 4 | hIL-25 | None | |
| 3 | WT | 5 | hIL-25 | Anti-IL-25 H4H10871P | 5 mg/kg |
| 4 | WT | 5 | hIL-25 | Anti-IL-25 H4H10871P | 25 mg/kg |

Measurement of Circulating IgE Levels

Blood samples were collected from each mouse via terminal cardiac puncture using a $27G^{1/2}$ 1 ml TB syringe (BD, #309306) and the collected blood was placed into a BD Microtainer® serum separator tube (BD, #365956). After centrifugation, the serum was collected and was subsequently transferred to new tubes.

To determine the total IgE concentration in the serum samples, a sandwich ELISA OPTEIA kit (BD, #555248) was used according to the manufacturer's instructions along with BD OPTEIA Reagent set B (BD, #550534). Briefly, serum samples were diluted in reagent diluent and plated onto 96-well plates coated with an anti-IgE capture antibody. Purified mouse IgE, supplied by the manufacturer, was used as a reference standard. After washing, plate-bound total IgE was detected using a biotinylated anti-mouse IgE antibody followed by addition of a streptavidin—Horse radish peroxidase conjugate. The chromagen 3,3',5,5'-tetramethylbenzidine was subsequently added to produce a colorimetric reaction and then neutralized with 1M sulfuric acid before measuring absorbance at 450 nm on a Molecular Devices SpectraMax M5 plate reader. Data analysis was performed using Prism™ software (GraphPad). The mean amounts of circulating IgE for each experimental group are expressed in ng/mL±standard deviation (SD), as shown in Table 18 and 19.

Lung Harvest for Pulmonary Cell Infiltrate Analysis

After exsanguination, the caudal lobe of the right lung from each mouse was removed, chopped into cubes that were approximately 2 to 3 mm in size, and placed into a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025), which was incubated in a 37° C. water bath for 20 minutes and vortexed every 5 minutes. The reaction was stopped by adding ethylenediaminetetraacetic acid (Gibco, #15575) at a final concentration of 10 mM. Each lung was subsequently dissociated using a gentle MACS Dissociator® (Miltenyi Biotec, #130-095-937) and then filtered through a 70 μm filter and centrifuged. The resulting lung pellet was resuspended in 1 mL of 1× red blood cell lysing buffer (Sigma, #R7757) to remove red blood cells. After incubation for 3 minutes at room temperature, 3 mL of 1×DMEM was added to deactivate the red blood cell lysing buffer. The cell suspensions were then centrifuged, and the resulting cell pellets were resuspended in 5 mL of MACS buffer (autoMACS Running Buffer; Miltenyi Biotec, #130-091-221). The resuspended samples were filtered through a 70 μm filter and 1×10$^6$ cells per well were plated in a 96-well V-bottom plate. Cells were then centrifuged and the pellets were washed in 1×PBS. After a second centrifugation, the cell pellets were resuspended in 100 μL of LIVE/DEAD® Fixable Aqua Dead Cell Stain (Life Technologies, #L34957) diluted at 1:1000 in 1×PBS to determine cell viability and incubated for 20 minutes at room temperature while protected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4° C. The cells were washed once and then incubated in the appropriate antibody mixture (described in Table 17) diluted in MACS buffer for 30 minutes at 4° C. while protected from light. After antibody incubation, the cells were washed twice in MACS buffer, resuspended in BD cytofix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of eosinophils by flow cytometry.

Eosinophils were defined as Live, CD45$^+$, GR1$^-$, CD11c$^{lo}$, SiglecF$^{hi}$. Data are expressed as frequency of eosinophils within the immune cells population (% of CD45+ cells±SD) as shown in Table 20 and 21.

TABLE 17

Antibodies Used for Flow Cytometry Analysis

| Antibody | Fluorochrome | Manufacturer | Catalog Number | Final dilution |
|---|---|---|---|---|
| CD11c | APC | BD Biosciences | 550261 | 1/100 |
| CD45 | PerCP Cy5.5 | eBiosciences | 45-0454-82 | 1/800 |
| F4/80 | Pacific Blue | eBiosciences | 48-4801-82 | 1/200 |

TABLE 17-continued

Antibodies Used for Flow Cytometry Analysis

| Antibody | Fluorochrome | Manufacturer | Catalog Number | Final dilution |
|---|---|---|---|---|
| Siglec-F | PE | BD Biosciences | 552126 | 1/100 |
| Ly6G (Gr-1) | APC-eFluor780 | eBiosciences | 47-5931-82 | 1/200 |

Luna Harvest for Goblet Cells Metaplasia Analysis

After exsanguination, the left lung from each mouse was removed and placed into tubes containing 5 mL of a solution of 4% (w/v) paraformaldehyde (Boston Bioproducts, #BM-155) in 1× phosphate buffered saline and stored at room temperature for at least 24 hours. Lung samples were then blotted dry and transferred to tubes containing 70% Ethanol. The samples were sent to Histoserv, Inc (Germantown, Md.) for paraffin embedding, sectioning and periodic acid Schiff (PAS) staining.

Pictures of the PAS stained lung sections were taken using a Zeiss Axio Imager A2 microscope (40× objective). Cells positively staining for PAS were identified as goblet cells and counted within a 1 to 2 mm long section of the epithelium of the main bronchi. Goblet cell counts were expressed relative to the total number of cells within the analyzed section of the epithelium. Data expressed as frequency of goblet cells±SD are shown in Table 22.

TABLE 18

Circulating levels of total mouse IgE from Study 1

| Group | Mice | Construct | Antibody | mAb dose | Mean circulating IgE levels (ng/mL ± SD) |
|---|---|---|---|---|---|
| 1 | WT | Empty vector | None | | 311 ± 200 |
| 2 | WT | hIL-25 | Isotype control | 25 mg/kg | 3417 ± 1627 |
| 3 | WT | hIL-25 | H4H10871P | 25 mg/kg | 333 ± 125 |
| 4 | WT | hIL-25 | H4H10900P | 25 mg/kg | 1240 ± 2233 |

TABLE 19

Circulating levels of total mouse IgE from Study 2

| Group | Mice | Construct | Antibody | mAb dose | Mean circulating IgE levels (ng/mL ± SD) |
|---|---|---|---|---|---|
| 1 | WT | Empty vector | None | | 93 ± 71 |
| 2 | WT | hIL-25 | None | | 1186 ± 1370 ** |
| 3 | WT | hIL-25 | H4H10871P | 5 mg/kg | 190 ± 99 |
| 4 | WT | hIL-25 | H4H10871P | 25 mg/kg | 118 ± 26 |

Statistical significance compared to Empty vector group determined by Kruskal-Wallis test with Dunn's multiple comparison post-test is indicated (** $p < 0.001$).

TABLE 20

Frequency of lung eosinophils from Study 1

| Group | Mice | Construct | Antibody | mAb dose | Mean frequency of eosinophils (% of CD45+ cells ± SD) |
|---|---|---|---|---|---|
| 1 | WT | Empty vector | None | | 1.47 ± 0.16 |
| 2 | WT | hIL-25 | Isotype control | 25 mg/kg | 17.20 ± 2.39 |

TABLE 20-continued

Frequency of lung eosinophils from Study 1

| Group | Mice | Construct | Antibody | mAb dose | Mean frequency of eosinophils (% of CD45+ cells ± SD) |
|---|---|---|---|---|---|
| 3 | WT | hIL-25 | H4H10871P | 25 mg/kg | 1.03 ± 0.16 ** |
| 4 | WT | hIL-25 | H4H10900P | 25 mg/kg | 1.36 ± 0.19 |

Statistical significance compared to Isotype control determined by Kruskal-Wallis test with Dunn's multiple comparison post-test is indicated
(** p < 0.001).

TABLE 21

Frequency of lung eosinophils from Study 2

| Group | Mice | Construct | Antibody | mAb dose | Mean frequency of eosinophils (% of CD45+ cells ± SD) |
|---|---|---|---|---|---|
| 1 | WT | Empty vector | None | | 6.35 ± 1.46 |
| 2 | WT | hIL-25 | None | | 32.29 ± 18.35 |
| 3 | WT | hIL-25 | H4H10871P | 5 mg/kg | 4.46 ± 1.66 * |
| 4 | WT | hIL-25 | H4H10871P | 25 mg/kg | 5.23 ± 2.13 |

Statistical significance compared to hIL-25 determined by Kruskal-Wallis test with Dunn's multiple comparison post-test is indicated
(* p < 0.01).

TABLE 22

Goblet cells metaplasia from Study 2

| Group | Mice | Construct | Antibody | mAb dose | Mean frequency of goblet cells (% total cells in epithelium ± SD) |
|---|---|---|---|---|---|
| 1 | WT | Empty vector | None | | 1.15 ± 1.67 |
| 2 | WT | hIL-25 | None | | 59.63 ± 39.74 |
| 3 | WT | hIL-25 | H4H10871P | 5 mg/kg | 1.71 ± 1.93 |
| 4 | WT | hIL-25 | H4H10871P | 25 mg/kg | 6.90 ± 11.55 |

Wild type mice overexpressing human IL-25 by HDD demonstrated increased levels of circulating IgE (3417±1627 ng/mL for study 1 and 1186±1370 ng/mL for study 2) as compared to wild type mice given empty vector by HDD (311±200 ng/mL for study 1 and 1186±1370 ng/mL for study 2). The levels of circulating IgE were reduced in each study when mice overexpressing human IL-25 by HDD were treated with IL-25 antibodies, as shown in Table 18 and 19. Wild type mice overexpressing human IL-25 by HDD demonstrated a trend towards increased frequency of lung eosinophils (17.20±2.39% for study 1 and 32.29±18.35% for study 2) as compare to wild type mice given empty vector by HDD (1.47±0.16% for study 1 and 6.35±1.46% for study 2). The frequency of lung eosinophils was reduced in each study when mice overexpressing human IL-25 by HDD were treated with IL-25 antibodies, as shown in Table 20 and 21. Wild type mice overexpressing human IL-25 by HDD demonstrated a trend towards increased goblet cell metaplasia (59.63±39.74 for study 2) as compare to wild type mice given empty vector by HDD (1.15±1.67 for study 2). The frequency of goblet cell metaplasia was reduced in study 2 when mice overexpressing human IL-25 by HDD were treated with IL-25 antibodies, as shown in Table 22.

Example 9. Chronic House Dust Mite Allergen (HDM)-Induced Lung Inflammation in WT and IL-25 KO Mice To determine the role of IL-25 in a relevant in vivo model, a chronic house dust mite allergen (HDM)-induced lung inflammation study was conducted in both wild type mice (WT) and in mice that were homozygous for the deletion of mouse IL-25 (IL-25 KO mice).

IL-25 KO and WT mice were intranasally administered either 50 μg of house dust mite extract (HDM; Greer, #XPB70D3A2.5) diluted in 20 μL of 1× phosphate buffered saline (PBS) or 20 μL of 1×PBS for 5 days per week for 12 weeks. All mice were sacrificed on the first day of the thirteenth week of the study and their lungs were harvested. Experimental dosing and treatment protocol for groups of mice are shown in Table 23.

TABLE 23

Experimental dosing and treatment protocol for groups of mice

| Group | Mice | n | Intranasal challenge | Length of intranasal challenge |
|---|---|---|---|---|
| 1 | WT | 3 | 1X PBS (Saline) | 12 weeks |
| 2 | WT | 4 | 50 μg HDM in 20 μL 1X PBS | 12 weeks |
| 3 | IL-25 KO | 4 | 1X PBS (Saline) | 12 weeks |
| 4 | IL-25 KO | 5 | 50 μg HDM in 20 μL 1X PBS | 12 weeks |

Lung Harvest for Pulmonary Cell Infiltrate Analysis

After exsanguination, the caudal lobe of the right lung from each mouse was removed, chopped into cubes that were approximately 2 to 3 mm in size, and placed into a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025), which was incubated in a 37° C. water bath for 20 minutes and inverted every 5 minutes. The reaction was stopped by adding ethylenediaminetetraacetic acid (Gibco, #15575) at a final concentration of 10 mM. Each lung was subsequently dissociated using a gentleMACS Dissociator® (Miltenyi Biotec, #130-095-937) and then filtered through a 70 μm filter and centrifuged. The resulting lung pellet was resuspended in 1 mL of 1× red blood cell lysing buffer (Sigma, #R7757) to remove red blood cells. After incubation for 3 minutes at room temperature, 3 mL of MACS buffer (autoMACS Running Buffer; Miltenyi Biotec, #130-091-221) was added to deactivate the red blood cell lysing buffer. The cell suspensions were then centrifuged, and the resulting cell pellets were resuspended in 5 mL of MACS buffer. The resuspended samples were filtered through a 70 μm filter and 1×10$^6$ cells per well were plated in a 96-well V-bottom plate. Cells were then centrifuged and the pellets were washed in 1×PBS. After a second centrifugation, the cell pellets were resuspended in 100 μL of LIVE/DEAD® Fixable Aqua Dead Cell Stain (Life Technologies, #L34957) diluted at 1:1000 in 1×PBS to determine cell viability and incubated for 20 minutes at room temperature while protected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4° C. The cells were washed once and then incubated in the appropriate antibody mixture (described in Table 24) diluted in MACS buffer for 30 minutes at 4° C. while protected from light. After antibody incubation, the cells were washed twice in MACS buffer, resuspended in BD cytofix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of neutrophils and lymphocytes by flow cytometry.

Neutrophils were defined as live, $CD45^+$, $F4/80^-$, $Ly6G^+$, $Ly6C^{Int}$. Data for neutrophils are expressed as a frequency of live cells analyzed (frequency of live, ±SD) as shown in Table 25. CD4 and CD8 T cells were defined as live, $SSC^{Lo}$, $FSC^{Lo}$, $CD45^+$, $CD19^-$, $CD3^+$, $CD8^-$, $CD4^+$ and Live, $SSC^{Lo}$, $FSC^{Lo}$, $CD45^+$, $CD19^-$, $CD3^+$, $CD8^+$, $CD4^-$ respectively. Data for CD4 and CD8 T cells are expressed as the frequency of CD4 T cells relative to the frequency of CD8 T cells (CD4/CD8 ratio, ±SD) as shown in Table 25. Activated CD4 T cells were defined as cells that were live, $CD45^+$, $SSC^{Lo}$, $FSC^{Lo}$, $CD3^+$, $CD19^-$, $CD4^+$, $CD8^-$, and $CD69^+$. Activated CD8 T cells were defined as cells that were live, $CD45^+$, $SSC^{Lo}$, $FSC^{Lo}$, $CD3^+$, $CD19^-$, $CD4^+$, $CD8^-$, and CD69±. Data for activated cells were expressed as frequency of activated cells ($CD69^+$) within the parent population (frequency of CD4 or CD8 T cells, ±SD) as shown in Table 25.

TABLE 24

Antibodies Used for Flow Cytometry Analysis

| Antibody | Fluorochrome | Manufacturer | Catalog Number | Final dilution |
|---|---|---|---|---|
| CD11c | APC | BD Biosciences | 550261 | 1/100 |
| CD45 | PerCP Cy5.5 | eBiosciences | 45-0454-82 | 1/800 |
| F4/80 | Pacific Blue | eBiosciences | 48-4801-82 | 1/200 |
| Siglec-F | PE | BD Biosciences | 552126 | 1/100 |
| Ly6G (Gr-1) | APC-eFluor780 | eBiosciences | 47-5931-82 | 1/200 |
| CD3 | PE-Cy7 | BD Biosciences | 552774 | 1/200 |
| CD19 | eFluor 450 | eBiosciences | 48-0193-82 | 1/200 |
| CD4 | APC-H7 | BD Biosciences | 560181 | 1/200 |
| CD8 | APC | eBiosciences | 17-0081-82 | 1/200 |
| CD69 | PE | eBiosciences | 12-0691-82 | 1/200 |

Lung Harvest for Cytokine Analysis:

After exsanguination, the cranial and middle lobes of the right lung from each mouse were removed and placed into tubes containing a solution of tissue protein extraction reagent (1×T-PER reagent; Pierce, #78510) supplemented with 1× Halt Protease inhibitor cocktail (Pierce, #78430). All further steps were performed on ice. The volume of T-PER Reagent (containing the protease inhibitor cocktail) was adjusted for each sample to match a 1:7.5 (w/v) tissue to T-PER ratio. Lung samples were manually homogenized in the tubes, using disposable pestles (Argos Technologies, cat P9950-901). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 µL of diluted extract samples were plated into 96 well plates in duplicates and mixed with 200 µL of 1× Dye Reagent (Biorad, #500-0006). Serial dilutions of bovine serum albumin (Sigma, #A7979), starting at 700 µg/mL in 1×T-Per reagent were used as a standard to determine the exact protein concentration of the extracts. After a 5-minute incubation at room temperature, absorbance at 595 nm was measured on a Molecular Devices SpectraMax M5 plate reader. Data analysis to determine total protein content was performed using GraphPad Prism™ software.

Cytokine concentrations in the lung protein extracts were measured using a Proinflammatory Panel 1 (mouse) multiplex immunoassay kit (MesoScale Discovery, #K15048D), according to the manufacturer's instructions. Briefly, 50 µL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) Tween-20, followed by the addition of 25 µL of Detection Antibody Solution diluted in Diluent 45. After another 2-hour incubation at room temperature while shaking, the plate was washed 3 times, and 150 µL of 2× Read Buffer was added to each well. Electrochemiluminescence was immediately read on a MSD Spector® instrument. Data analysis was performed using GraphPad Prism™ software.

Each cytokine concentration in lung total protein extracts measured was normalized to the total protein content of the extracts measured by the Bradford assay, and expressed as pg of cytokine per mg of total lung proteins (pg/mg lung protein, ±SD) as shown in Table 26.

TABLE 25

Frequency of pulmonary cell infiltrate as determined by flow cytometry

| Experimental Group | Mean Frequency of Neutrophils (% of Live cells, ±SD) | Mean CD4/CD8 ratio (±SD) | Mean Frequency of activated CD4+ T cells (% of CD4 T cells, ±SD) | Mean Frequency of activated CD8+ T cells (% of CD8 T cells, ±SD) |
|---|---|---|---|---|
| WT Saline | 6.57 ± 1.27 ** | 1.00 ± 0.07 ** | 10.74 ± 0.75 *** | 3.01 ± 1.24 ** |
| WT HDM | 13.53 ± 2.63 | 3.89 ± 1.63 | 57.10 ± 4.03 | 26.18 ± 13.16 |
| IL-25 KO Saline | 5.98 ± 0.26 ** | 1.33 ± 0.21 ** | 10.16 ± 2.14 *** | 5.51 ± 6.00 ** |
| IL-25 KO HDM | 6.89 ± 2.68 ** | 2.02 ± 0.48 * | 38.65 ± 11.06 ** | 6.37 ± 3.10 ** |

Statistical significance compared to WT HDM group determined by 2 Way ANOVA with Tukey's multiple comparison post-test is indicated (** $p < 0.001$;

*** $p < 0.0001$).

TABLE 26

Cytokines concentration in lung protein extracts.

| Experimental Group | Mean [IL-1β] in lung protein extracts (pg/mg lung protein) ±SD | Mean [TNFα] in lung protein extracts (pg/mg lung protein) ±SD |
|---|---|---|
| WT Saline | 0.24 ± 0.11 ** | 0.76 ± 0.22 *** |
| WT HDM | 138.70 ± 70.17 | 11.42 ± 2.60 |
| IL-25 KO Saline | 0.49 ± 0.42 *** | 0.78 ± 0.14 *** |
| IL-25 KO HDM | 21.69 ± 17.90 ** | 5.01 ± 2.94 ** |

Statistical significance compared to WT HDM group determined by 2 Way ANOVA with Tukey's multiple comparison post-test is indicated
(** $p < 0.001$;
*** $p < 0.0001$).

As shown in Table 25, long-term or chronic exposure to HDM in WT mice induced a significant increase in lung neutrophilia as compared to WT mice exposed to PBS alone. Chronic HDM challenge in WT mice also induced a shift in the balance of CD4 and CD8 T cells in the lungs, as well as an increase in the frequency of activated CD4 and CD8 T cells. The increase in lung neutrophilia and these other features of lung cellular inflammation induced by chronic HDM challenge, were significantly reduced in IL-25 KO mice as compared to WT mice.

Long-term exposure to HDM induced a significant increase in the levels of pro-inflammatory cytokines such as IL-1β and TNFα in the lungs of WT mice as compare to WT mice exposed to PBS alone. In contrast, chronic exposure of IL-25 KO mice to HDM did not significantly increase the lung levels of these two cytokines as shown in Table 26.

In summary, chronic exposure to HDM induces features of lung inflammation in WT mice that are absent in the lungs of IL-25 KO mice receiving the same challenge.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated nucleic acid molecule comprising a nucleic acid sequence encoding an antibody or antigen-binding fragment thereof that specifically binds to human interleukin-25 (IL-25), wherein the antibody or antigen-binding fragment thereof comprises a set of six complementarity determining regions (HCDR1, HCDR2, HCDR3, LCDR1, LCDR2, and LCDR3) contained within a heavy chain variable region (HCVR)/light chain variable region (LCVR) amino acid sequence pair as set forth in SEQ ID NOs: 114/122.

2. The isolated nucleic acid molecule of claim 1, wherein the nucleic acid molecule encodes an antibody or antigen-binding fragment thereof that comprises an HCDR1 comprising the amino acid sequence of SEQ ID NO:116, an HCDR2 comprising the amino acid sequence of SEQ ID NO:118, an HCDR3 comprising the amino acid sequence of SEQ ID NO:120, an LCDR1 comprising the amino acid sequence of SEQ ID NO:124, an LCDR2 comprising the amino acid sequence of SEQ ID NO:126, and an LCDR3 comprising the amino acid sequence of SEQ ID NO:128.

3. The isolated nucleic acid molecule of claim 1, wherein the antibody or antigen-binding fragment thereof comprises the HCVR and LCVR sequences of an amino acid sequence pair as set forth in SEQ ID NOs: 114/122.

4. The isolated nucleic acid molecule of claim 1, wherein the nucleic acid sequence encoding the HCVR has at least 90% sequence identity to the nucleic acid sequence set forth in SEQ ID NO: 113, and the nucleic acid sequence encoding the LCVR has at least 90% sequence identity to the nucleic acid sequence set forth in SEQ ID NO: 121.

5. The isolated nucleic acid molecule of claim 1, wherein the nucleic acid sequence encoding the HCVR has at least 95% sequence identity to the nucleic acid sequence set forth in SEQ ID NO: 113, and the nucleic acid sequence encoding the LCVR has at least 95% sequence identity to the nucleic acid sequence set forth in SEQ ID NO: 121.

6. The isolated nucleic acid molecule of claim 1, wherein the nucleic acid sequence encoding the HCVR comprises the nucleic acid sequence of SEQ ID NO: 113, and the nucleic acid sequence encoding the LCVR comprises the nucleic acid sequence of SEQ ID NO: 121.

7. A composition comprising a first nucleic acid molecule and a second nucleic acid molecule, wherein:
the first nucleic acid molecule comprises a nucleic acid sequence encoding an HCVR of an antibody or antigen-binding fragment thereof that specifically binds to human IL-25, wherein the HCVR comprises an HCDR1 comprising the amino acid sequence of SEQ ID NO:116, an HCDR2 comprising the amino acid sequence of SEQ ID NO:118, and an HCDR3 comprising the amino acid sequence of SEQ ID NO:120; and
the second nucleic acid molecule comprises a nucleic acid sequence encoding an LCVR of an antibody or antigen-binding fragment thereof that specifically binds to human IL-25, wherein the LCVR comprises an LCDR1 comprising the amino acid sequence of SEQ ID NO:124, an LCDR2 comprising the amino acid sequence of SEQ ID NO:126, and an LCDR3 comprising the amino acid sequence of SEQ ID NO:128.

8. The composition of claim 7, wherein the HCVR comprises the amino acid sequence of SEQ ID NO: 114, and the LCVR comprises the amino acid sequence of SEQ ID NO: 122.

9. The composition of claim 7, wherein the first nucleic acid molecule comprises the nucleic acid sequence of SEQ ID NO: 113, and the second nucleic acid molecule comprises the nucleic acid sequence of SEQ ID NO: 121.

10. An expression vector comprising the nucleic acid molecule of claim 1.

11. An isolated host cell comprising the expression vector of claim 10.

12. A method of producing an anti-IL-25 antibody or antigen-binding fragment thereof, comprising the steps of culturing the host cell of claim 11 under conditions permitting production of the antibody or antigen-binding fragment thereof, and recovering the antibody or antigen-binding fragment thereof so produced.

* * * * *